US008735132B2

(12) United States Patent
Santos et al.

(10) Patent No.: US 8,735,132 B2
(45) Date of Patent: May 27, 2014

(54) MUTATIONS AND GENETIC TARGETS FOR ENHANCED L-TYROSINE PRODUCTION

(75) Inventors: Christine Santos, Richmond, CA (US); Gregory Stephanopoulos, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 136 days.

(21) Appl. No.: 13/101,579

(22) Filed: May 5, 2011

(65) Prior Publication Data
US 2011/0300588 A1 Dec. 8, 2011

Related U.S. Application Data

(60) Provisional application No. 61/332,560, filed on May 7, 2010.

(51) Int. Cl.
*C12N 1/20* (2006.01)
*C12P 13/04* (2006.01)
*C12P 13/22* (2006.01)
*C12R 1/19* (2006.01)
*C12P 13/00* (2006.01)
*C12R 1/01* (2006.01)

(52) U.S. Cl.
CPC ............... *C12R 1/19* (2013.01); *C12P 13/004* (2013.01); *C12N 1/20* (2013.01); *C12R 1/01* (2013.01); *C12P 13/225* (2013.01)
USPC ................. 435/252.1; 435/252.8; 435/106; 435/108

(58) Field of Classification Search
None
See application file for complete search history.

(56) References Cited

U.S. PATENT DOCUMENTS

2012/0034661 A1    2/2012   Stephanopoulos et al.

FOREIGN PATENT DOCUMENTS

WO    WO 2009/025761 A2    2/2009
WO    WO 2009/061429 A2    5/2009
WO    WO 2011/140342 A1    11/2011

OTHER PUBLICATIONS

Bacteria taxonomy search results, Retrieved from the Internet < http://www.ncbi.nlm.nih.gov/Taxonomy/Browser/wwwtax.cgi?mode=Info&id=2&lvl=3&lin=f&keep=1&srchmode=1&unlock>, Retrieved on May 1, 2013.*
Branden et al., "Introduction to Protein Structure Second Edition", Garland Publishing Inc., New York, 1999, p. 247.*
Witkowski et al., Biochemistry, 38, 11643-11650, 1999.*
Seffernick et al. (J. Bacteriol. 183(8):2405-2410, 2001).*
Alper et al., Global transcription machinery engineering: a new approach for improving cellular phenotype. Metab Eng. May 2007;9(3):258-67. Epub Jan. 8, 2007.

Alper et al., Tuning genetic control through promoter engineering. Proc Natl Acad Sci U S A. Sep. 6, 2005;102(36):12678-83. Epub Aug. 25, 2005.
Bro et al., Improvement of galactose uptake in *Saccharomyces cerevisiae* through overexpression of phosphoglucomutase: example of transcript analysis as a tool in inverse metabolic engineering. Appl Environ Microbiol. Nov. 2005;71(11):6465-72.
Browning et al., The regulation of bacterial transcription initiation. Nat Rev Microbiol. Jan. 2004;2(1):57-65.
Chang et al., Gene expression profiling of *Escherichia coli* growth transitions: an expanded stringent response model. Mol Microbiol. Jul. 2002;45(2):289-306.
Dangi et al., Versatility of the carboxy-terminal domain of the alpha subunit of RNA polymerase in transcriptional activation: use of the DNA contact site as a protein contact site for MarA. Mol Microbiol. Oct. 2004;54(1):45-59.
Datsenko et al., One-step inactivation of chromosomal genes in *Escherichia coli* K-12 using PCR products. Proc Natl Acad Sci U S A. Jun. 6, 2000;97(12):6640-5.
Durfee et al., Transcription profiling of the stringent response in *Escherichia coli*. J Bacteriol. Feb. 2008;190(3):1084-96. Epub Nov. 26, 2007.
Fukui et al., Production of l-tryptophan, l-tyrosine and their analogues by use of immobilized tryptophanase and immobilized beta-tyrosinase. European Journal of Applied Microbiology. 1975;1(1):25-39.
Gaal et al., DNA-binding determinants of the alpha subunit of RNA polymerase: novel DNA-binding domain architecture. Genes Dev. Jan. 1, 1996;10(1):16-26.
Gajiwala et al., HDEA, a periplasmic protein that supports acid resistance in pathogenic enteric bacteria. J Mol Biol. Jan. 21, 2000;295(3):605-12.
Garibyan et al., Use of the rpoB gene to determine the specificity of base substitution mutations on the *Escherichia coli* chromosome. DNA Repair (Amst) May 13, 2003;2(5):593-608.
Gruber et al., Multiple sigma subunits and the partitioning of bacterial transcription space. Annu Rev Microbiol. 2003;57:441-66. First published online as Rev in Adv Jun. 4, 2003.
Ikeda et al., A genome-based approach to create a minimally mutated *Corynebacterium glutamicum* strain for efficient L-lysine production. J Ind Microbiol Biotechnol. Jul. 2006;33(7):610-5. Epub Feb. 28, 2006.
Imaizumi et al., The effect of intracellular ppGpp levels on glutamate and lysine overproduction in *Escherichia coli*. J Biotechnol. Sep. 18, 2006;125(3):328-37. Epub Apr. 18, 2006.
Ishihama, Functional modulation of *Escherichia coli* RNA polymerase. Annu Rev Microbiol. 2000;54:499-518.
Jishage et al., Regulation of sigma factor competition by the alarmone ppGpp. Genes Dev. May 15, 2002;16(10):1260-70.
Kern et al., *Escherichia coli* HdeB is an acid stress chaperone. J Bacteriol. Jan. 2007;189(2):603-10. Epub Nov. 3, 2006.
Klein-Marcuschamer et al., Assessing the potential of mutational strategies to elicit new phenotypes in industrial strains. Proc Natl Acad Sci U S A. Feb. 19, 2008; 105(7): 2319-2324. Epub Feb. 5, 2008.
Klein-Marcuschamer et al., Mutagenesis of the bacterial RNA polymerase alpha subunit for improvement of complex phenotypes. Appl Environ Microbiol. May 2009;75(9):2705-11. Epub Feb. 27, 2009.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to identification of mutations and genetic targets for enhanced L-tyrosine production, and bacterial strains capable of L-tyrosine production.

14 Claims, 16 Drawing Sheets

(56) References Cited

OTHER PUBLICATIONS

Leonard et al., Engineering central metabolic pathways for high-level flavonoid production in *Escherichia coli*. Appl Environ Microbiol. Jun. 2007;73(12):3877-86. Epub Apr. 27, 2007.

Leonard et al., Strain improvement of recombinant *Escherichia coli* for efficient production of plant flavonoids. Mol Pharm. Mar.-Apr. 2008;5(2):257-65. Epub Mar. 12, 2008.

Li et al., Alpha-helical, but not beta-sheet, propensity of proline is determined by peptide environment. Proc Natl Acad Sci U S A. Jun. 25, 1996;93(13):6676-81.

Lutke-Eversloh et al., A semi-quantitative high-throughput screening method for microbial L-tyrosine production in microtiter plates. J Ind Microbiol Biotechnol. Dec. 2007;34(12):807-11. Epub Oct. 10, 2007.

Lutke-Eversloh et al., Combinatorial pathway analysis for improved L-tyrosine production in *Escherichia coli*: identification of enzymatic bottlenecks by systematic gene overexpression. Metab Eng. Mar. 2008;10(2):69-77. Epub Dec. 7, 2007.

Lutke-Eversloh et al., L-tyrosine production by deregulated strains of *Escherichia coli*. Appl Microbiol Biotechnol. May 2007;75(1):103-10. Epub Jan. 13, 2007.

Ma et al., Characterization of EvgAS-YdeO-GadE branched regulatory circuit governing glutamate-dependent acid resistance in *Escherichia coli*. J Bacteriol. Nov. 2004;186(21):7378-89.

Ma et al., GadE (YhiE) activates glutamate decarboxylase-dependent acid resistance in *Escherichia coli* K-12. Mol Microbiol. Sep. 2003;49(5):1309-20.

Magnusson et al., ppGpp: a global regulator in *Escherichia coli*. Trends Microbiol. May 2005;13(5):236-42. Epub Mar. 28, 2005.

Malki et al., Solubilization of protein aggregates by the acid stress chaperones HdeA and HdeB. J Biol Chem. May 16, 2008;283(20):13679-87.

Masuda et al., Regulatory network of acid resistance genes in *Escherichia coli*. Mol Microbiol. May 2003;48(3):699-712.

Mei et al., A cysteine-histidine-aspartate catalytic triad is involved in glutamine amide transfer function in purF-type glutamine amidotransferases. J Biol Chem. Oct. 5, 1989;264(28):16613-9.

Mei et al., Amino-terminal deletions define a glutamine amide transfer domain in glutamine phosphoribosylpyrophosphate amidotransferase and other PurF-type amidotransferases. J Bacteriol. Jun. 1990;172(6):3512-4.

Murakami et al., Transcription factor recognition surface on the RNA polymerase alpha subunit is involved in contact with the DNA enhancer element. EMBO J. Aug. 15, 1996;15(16):4358-67.

Neidhardt et al., Culture medium for enterobacteria. J Bacteriol. Sep. 1974;119(3):736-47.

Nishino et al., Global analysis of genes regulated by EvgA of the two-component regulatory system in *Escherichia coli*. J Bacteriol. Apr. 2003;185(8):2667-72.

Nishino et al., Overexpression of the response regulator evgA of the two-component signal transduction system modulates multidrug resistance conferred by multidrug resistance transporters. J. Bacteriol. Feb. 2001;183(4):1455-8.

O'Donoghue et al., On the structure of hisH: protein structure prediction in the context of structural and functional genomics. J Struct Biol. May-Jun. 2001;134(2-3):257-68. Epub Aug. 3, 2001.

Olson et al., Production of tyrosine from sucrose or glucose achieved by rapid genetic changes to phenylalanine-producing *Escherichia coli* strains. Appl Microbiol Biotechnol. Apr. 2007;74(5):1031-40. Epub Jan. 11, 2007.

Patnaik et al., L-tyrosine production by recombinant *Escherichia coli*: fermentation optimization and recovery. Biotechnol Bioeng. Mar. 1, 2008;99(4):741-52.

Paul et al., DksA potentiates direct activation of amino acid promoters by ppGpp. Proc Natl Acad Sci U S A. May 31, 2005;102(22):7823-8. Epub May 17, 2005.

Potrykus et al., (p)ppGpp: still magical? Annu Rev Microbiol. 2008;62:35-51. First published online as Rev in Adv May 2, 2008.

Qi et al., Functional expression of prokaryotic and eukaryotic genes in *Escherichia coli* for conversion of glucose to p-hydroxystyrene. Metab Eng. May 2007;9(3):268-76. Epub Feb. 22, 2007.

Riesenberg et al., High cell density cultivation of *Escherichia coli* at controlled specific growth rate. J Biotechnol. Aug. 1991;20(1):17-27.

Rolfes et al., Regulation of *Escherichia coli* purF. Mutations that define the promoter, operator, and purine repressor gene. J Biol Chem. Dec. 25, 1988;263(36):19649-52.

Ross et al., A third recognition element in bacterial promoters: DNA binding by the alpha subunit of RNA polymerase. Science. Nov. 26, 1993;262(5138):1407-13.

Santos et al., Melanin-based high-throughput screen for L-tyrosine production in *Escherichia coli*. Appl Environ Microbiol. Feb. 2008;74(4):1190-7. Epub Dec. 21, 2007.

Santos et al., Optimization of a heterologous pathway for the production of flavonoids from glucose. Metab Eng. Jul. 2011;13(4):392-400. doi: 10.1016/j.ymben.2011.02.002. Epub Feb. 12, 2011

Santos, Combinatorial search strategies for the metabolic engineering of microorganisms. Thesis. Massachusetts Institute of Technology, Dept. of Chemical Engineering. Jun. 30, 2010. 253 pages.

Sariaslani, Development of a combined biological and chemical process for production of industrial aromatics from renewable resources. Annu Rev Microbiol. 2007;61:51-69. First published as Rev in Adv Apr. 24, 2007.

Sarubbi et al., Basal ppGpp level adjustment shown by new spoT mutants affect steady state growth rates and rrnA ribosomal promoter regulation in *Escherichia coli*. Mol Gen Genet. Aug. 1988;213(2-3):214-22.

Schumacher et al., Crystal structure of LacI member, PurR, bound to DNA: minor groove binding by alpha helices. Science. Nov. 4, 1994;266(5186):763-70.

Sharma et al., Differential mechanisms of binding of anti-sigma factors *Escherichia coli* Rsd and bacteriophage T4 AsiA to *E. coli* RNA polymerase lead to diverse physiological consequences. J Bacteriol. May 2008;190(10):3434-43. Epub Mar. 21, 2008.

Sharma et al., Study of the interaction between bacteriophage T4 asiA and *Escherichia coli* sigma(70), using the yeast two-hybrid system: neutralization of asiA toxicity to *E. coli* cells by coexpression of a truncated sigma(70) fragment. J Bacteriol. Sep. 1999;181(18):5855-9.

Srivatsan et al., Control of bacterial transcription, translation and replication by (p)ppGpp. Curr Opin Microbiol. Apr. 2008;11(2):100-5. Epub Mar. 24, 2008.

Stephens et al., Guanosine 5'-diphosphate 3'-diphosphate (ppGpp): positive effector for histidine operon transcription and general signal for amino-acid deficiency. Proc Natl Acad Sci U S A. Nov. 1975;72(11):4389-93.

Traxler et al., The global, ppGpp-mediated stringent response to amino acid starvation in *Escherichia coli*. Mol Microbiol. Jun. 2008;68(5):1128-48. Epub Apr. 22, 2008.

Tusher et al., Significance analysis of microarrays applied to the ionizing radiation response. Proc Natl Acad Sci U S A. Apr. 24, 2001;98(9):5116-21. Epub Apr. 17, 2001.

UNIPROT Submission; Accession No. B3AQU7; Eppinger et al.; Jul. 22, 2008. 1 page.

UNIPROT Submission; Accession No. C9QQM2; Lucas et al.; Nov. 24, 2009. 1 page.

Vannelli et al., Production of p-hydroxycinnamic acid from glucose in *Saccharomyces cerevisiae* and *Escherichia coli* by expression of heterologous genes from plants and fungi. Metab Eng. Mar. 2007;9(2):142-51. Epub Nov. 15, 2006.

Wahlbom et al., Molecular analysis of a *Saccharomyces cerevisiae* mutant with improved ability to utilize xylose shows enhanced expression of proteins involved in transport, initial xylose metabolism, and the pentose phosphate pathway. Appl Environ Microbiol. Feb. 2003;69(2):740-6.

Young et al., Enzymic and nonenzymic transformations of chorismic acid and related cyclohexadienes. Biochim Biophys Acta. Oct. 7, 1969;192(1):62-72.

Zamir et al., Co-accumulation of prephenate, L-arogenate, and spiro-arogenate in a mutant of *Neurospora*. J Biol Chem. May 25, 1983;258(10):6492-6.

* cited by examiner

MUTATIONS AND GENETIC TARGETS FOR ENHANCED L-TYROSINE PRODUCTION

GOVERNMENT INTEREST

This invention was made with government support under Grant Nos. DGE0202745 and DGE0645960 awarded by the National Science Foundation, and under Grant No. DE-FC36-07GO17058 awarded by the Department of Energy. The government has certain rights in this invention.

RELATED APPLICATION

This application claims the benefit under 35 U.S.C. §119(e) of U.S. Provisional Application Ser. No. 61/332,560, filed on May 7, 2010, the entire contents of which is incorporated by reference herein in its entirety.

FIELD OF THE INVENTION

The invention relates to identification of mutations and genetic targets for enhanced L-tyrosine production, and bacterial strains capable of L-tyrosine production.

BACKGROUND OF THE INVENTION

Traditional metabolic engineering has often focused on the rational design of metabolic pathways, relying on extensive a priori knowledge of cellular mechanisms in order to redirect metabolite flow, revise metabolic regulation, or introduce new pathways to achieve a particular phenotype. In recent years, however, considerable advances in molecular biology and the growing availability of annotated genome sequences have made combinatorial methods of metabolic engineering an increasingly attractive approach for strain improvement.

L-tyrosine remains a valuable target compound for microbial production. L-tyrosine serves as a dietary supplement and a valuable precursor for a myriad of polymers, adhesives and coatings, pharmaceuticals, biocosmetics, and flavonoid products, and as such, there has been significant industrial interest in developing fermentation based processes for its synthesis (Leonard, Lim et al. 2007; Qi, Vannelli et al. 2007; Sariaslani 2007; Vannelli, Wei Qi et al. 2007; Leonard, Van et al. 2008).

SUMMARY OF THE INVENTION

There is a need to construct novel strains to be used for L-tyrosine production, and more specifically, identify mutations and genetic targets that could facilitate enhanced L-tyrosine production in bacteria such as *Escherichia coli*. Here, we describe the use of global transcription machinery engineering (gTME) (Alper and Stephanopoulos 2007) to identify mutants capable of high levels of L-tyrosine synthesis. Specific mutants were isolated which exhibited high L-tyrosine titers and high yield of L-tyrosine from glucose. A detailed characterization of these three strains by both transcriptional analysis and whole genome sequencing revealed that the overexpression of specific pathway regulators and the introduction of genetic mutations in chromosomal genes could successfully impart this L-tyrosine overproduction phenotype. This information was also used for the construction of a completely genetically defined organism capable of producing high levels of L-tyrosine.

According to certain aspects of the invention, bacterial cells are provided having improved L-tyrosine production relative to a parental strain, wherein the bacterial cell comprises (a) (1) one or more mutations in a sigma factor gene or a gene encoding an alpha subunit of RNA polymerase, and/or
(2) increased expression, relative to a parental strain, of one or more of evgA, relA, gadA, gadB, gadC, gadE, hdeA, hdeB, hdeD, and/or slp; and
(b) one or more mutations in hisH and/or purF.

In some embodiments, the sigma factor gene or the gene encoding an alpha subunit of RNA polymerase is a rpoA gene or a rpoD gene. In some embodiments, the one or more mutations in the sigma factor gene or the gene encoding an alpha subunit of RNA polymerase comprises one or more mutations that results in a helical destabilization or deletion of the C-terminal domain of the α-subunit of RNA polymerase (αCTD). In some embodiments, the one or more mutations in the sigma factor gene or the gene encoding an alpha subunit of RNA polymerase comprises one or more mutations of the nucleotide sequence of rpoA encoding amino acid residues V257 and/or L281. In some embodiments, the one or more mutations of the nucleotide sequence of rpoA encoding amino acid residue V257 encodes V257F or V257R. In some embodiments, the one or more mutations of the nucleotide sequence of rpoA encoding amino acid residue L281 encodes L281P. In some embodiments, the one or more mutations in the sigma factor gene or the gene encoding an alpha subunit of RNA polymerase comprises truncation of the nucleotide sequence of rpoD. In some embodiments, the truncation of the nucleotide sequence of rpoD results in a nucleotide sequence that encodes Region 4 and the end of Region 3 of RpoD protein. In some embodiments, the truncation is a deletion of the first 1512 base pairs of *E. coli* K12 rpoD or 756 amino acids of *E. coli* K12 RpoD protein. In each of the specific mutations referred to herein, the residues referred to correspond to residues within the full-length wild-type *E. coli* K12 gene or protein. However, the invention embraces equivalent mutations at equivalent positions in homologous genes or proteins other than the full-length wild-type *E. coli* K12 gene or protein, as will be appreciated by the person of ordinary skill in the art.

In some embodiments, the bacterial cell comprises increased expression, relative to a parental strain, of one or more of evgA, relA, gadA, gadB, gadC, gadE, hdeA, hdeB, hdeD, and/or slp, preferably evgA and/or relA. In some embodiments, the expression, relative to a parental strain, of one or more of evgA, relA, gadA, gadB, gadC, gadE, hdeA, hdeB, hdeD, and/or slp is increased by expression from a recombinant plasmid.

In some embodiments, the mutation in hisH comprises one or more mutations of the nucleotide sequence of hisH encoding amino acid residue L82. In some embodiments, the one or more mutations of the nucleotide sequence of hisH encoding amino acid residue L82 encodes L82R. In some embodiments, the mutation in purF comprises one or more mutations of the nucleotide sequence of purF encoding amino acid residue V5. In some embodiments, the one or more mutations of the nucleotide sequence of purF encoding amino acid residue V5 encodes V5G. In some embodiments, the mutation in purF comprises a T→C nucleotide substitution 17 base pairs upstream of the purF gene.

In some embodiments, the parental strain is an *E. coli* strain, optionally an *E. coli* K12 strain. In some embodiments, the *E. coli* K12 strain is *E. coli* K12 ΔpheΔtyrR pCL1920:: tyrA$^{fbr}$aroG$^{fbr}$ (P1) or *E. coli* K12 ΔpheA tyrR::tyrA$^{fbr}$ aroG$^{fbr}$ lacZ::tyrA$^{fbr}$aroG$^{fbr}$ (P2). In some embodiments, the strain is a completely genetically defined strain, preferably the rpoA14$^R$ strain.

In some embodiments, upon culturing the cell produces at least about 800 milligrams/liter L-tyrosine in the culture medium.

According to certain aspects of the invention, methods for producing L-tyrosine are provided. The methods include culturing the cells described herein to produce the L-tyrosine. In some embodiments, the methods further include recovering the L-tyrosine from the culture medium or the cells. In some embodiments, the culture has a carbon source and the carbon source is glucose or a glucose polymer.

In some embodiments, the cell produces at least 800 milligrams/liter L-tyrosine. In some embodiments, the cell produces at least 0.280 grams L-tyrosine/liter/hour. In some embodiments, the cell produces a yield of L-tyrosine on glucose of at least 0.16 grams L-tyrosine/gram glucose.

According to certain aspects of the invention, methods are provided for producing L-tyrosine. The methods include genetically modifying a bacterial cell to recombinantly express:
  (a) (1) one or more mutations in a sigma factor gene or a gene encoding an alpha subunit of RNA polymerase, and/or
    (2) increased expression, relative to a parental strain, of one or more of evgA, relA, gadA, gadB, gadC, gadE, hdeA, hdeB, hdeD, and/or slp; and
  (b) one or more mutations in hisH and/or purF, culturing a population of said cells, and
  optionally collecting L-tyrosine from the culture medium or the population of cells.

In some embodiments, the sigma factor gene or the gene encoding an alpha subunit of RNA polymerase is a rpoA gene or a rpoD gene. In some embodiments, the one or more mutations in the sigma factor gene or the gene encoding an alpha subunit of RNA polymerase comprises one or more mutations that results in a helical destabilization or deletion of the C-terminal domain of the α-subunit of RNA polymerase (αCTD). In some embodiments, the one or more mutations in the sigma factor gene or the gene encoding an alpha subunit of RNA polymerase comprises one or more mutations of the nucleotide sequence of rpoA encoding amino acid residues V257 and/or L281. In some embodiments, the one or more mutations of the nucleotide sequence of rpoA encoding amino acid residue V257 encodes V257F or V257R. In some embodiments, the one or more mutations of the nucleotide sequence of rpoA encoding amino acid residue L281 encodes L281P. In some embodiments, the one or more mutations in the sigma factor gene or the gene encoding an alpha subunit of RNA polymerase comprises truncation of the nucleotide sequence of rpoD. In some embodiments, the truncation of the nucleotide sequence of rpoD results in a nucleotide sequence that encodes Region 4 and the end of Region 3 of RpoD protein. In some embodiments, the truncation is a deletion of the first 1512 base pairs of $E.$ $coli$ K12 rpoD or 756 amino acids of $E.$ $coli$ K12 RpoD protein.

In some embodiments, the bacterial cell comprises increased expression, relative to a parental strain, of one or more of evgA, relA, gadA, gadB, gadC, gadE, hdeA, hdeB, hdeD, and/or slp, preferably evgA and/or relA. In some embodiments, the expression, relative to a parental strain, of one or more of evgA, relA, gadA, gadB, gadC, gadE, hdeA, hdeB, hdeD, and/or slp is increased by expression from a recombinant plasmid.

In some embodiments, the mutation in hisH comprises one or more mutations of the nucleotide sequence of hisH encoding amino acid residue L82. In some embodiments, the one or more mutations of the nucleotide sequence of hisH encoding amino acid residue L82 encodes L82R. In some embodiments, the mutation in purF comprises one or more mutations of the nucleotide sequence of purF encoding amino acid residue V5. In some embodiments, the one or more mutations of the nucleotide sequence of purF encoding amino acid residue V5 encodes VSG. In some embodiments, the mutation in purF comprises a T→C nucleotide substitution 17 base pairs upstream of the purF gene.

In some embodiments, the cell is a strain previously engineered for high endogenous L-tyrosine synthesis.

In some embodiments, the bacterial cell is an $E.$ $coli$ cell, optionally an $E.$ $coli$ K12 strain. In some embodiments, the $E.$ $coli$ K12 strain is $E.$ $coli$ K12 ΔpheAΔtyrR pCL1920::tyrA$^{fbr}$aroG$^{fbr}$ (P1) or $E.$ $coli$ K12 ΔpheA tyrR::tyrA$^{fbr}$aroG$^{fbr}$ lacZ::tyrA$^{fbr}$aroG$^{fbr}$ (P2).

In some embodiments, the culture has a carbon source and the carbon source is glucose or a glucose polymer.

In some embodiments, the cells produce at least about 800 milligrams/liter of L-tyrosine in the culture medium. In some embodiments, the cells produce at least about 0.280 grams L-tyrosine/liter/hour. In some embodiments, the cells produce a yield of L-tyrosine on glucose of at least about 0.16 grams L-tyrosine/gram glucose.

According to certain aspects of the invention, isolated nucleic acid molecules are provided that encode a rpoA gene product comprising one or more mutations of the nucleotide sequence of $E.$ $coli$ K12 rpoA encoding a mutation of valine at amino acid residue 257 (V257) to arginine (V257R), or equivalent amino acid in other rpoA genes of $E.$ $coli$ or of other bacterial strains.

According to certain aspects of the invention, isolated nucleic acid molecules are provided that encode a rpoD gene product comprising truncation of the nucleotide sequence of $E.$ $coli$ K12 rpoD that results in a nucleotide sequence that encodes Region 4 and the end of Region 3 of RpoD protein, or equivalent region of RpoD in other rpoD genes of $E.$ $coli$ or of other bacterial strains. In some embodiments, the truncation is a deletion of the first 1512 base pairs of $E.$ $coli$ K12 rpoD or 756 amino acids of $E.$ $coli$ K12 RpoD protein, or equivalent base pairs or amino acids in other rpoD genes of $E.$ $coli$ or of other bacterial strains.

According to certain aspects of the invention, isolated nucleic acid molecules are provided that encode a hisH gene product comprising one or more mutations of the nucleotide sequence of $E.$ $coli$ K12 hisH encoding a mutation of leucine at amino acid residue 82 (L82), or equivalent amino acid in other hisH genes of $E.$ $coli$ or of other bacterial strains. In some embodiments, the one or more mutations of the nucleotide sequence of hisH encoding amino acid residue L82 encodes arginine (L82R).

According to certain aspects of the invention, isolated nucleic acid molecules are provided that encode a purF gene product comprising one or more mutations of the nucleotide sequence of $E.$ $coli$ K12 purF encoding a mutation of valine at amino acid at residue 5 (V5), or equivalent amino acid in other purF genes of $E.$ $coli$ or of other bacterial strains. In some embodiments, the one or more mutations of the nucleotide sequence of purF encoding amino acid residue V5 encodes glycine (V5G).

According to certain aspects of the invention, recombinant expression vectors are provided that include the isolated nucleic acid molecules described herein.

According to certain aspects of the invention, isolated polypeptides are provided that are encoded by the isolated nucleic acid molecules described herein, or the recombinant expression vectors described herein.

According to certain aspects of the invention, bacterial cells are provided that include the nucleic acid molecules described herein, or the recombinant expression vectors described herein. In some embodiments, the cell is an *E. coli* cell.

According to certain aspects of the invention, methods for the production of L-tyrosine are provided. The methods include culturing the bacterial cells described herein under conditions that permit production of L-tyrosine. In some embodiments, the methods further include recovering the L-tyrosine from the culture medium or the cell.

These and other aspects of the invention are described further below.

DETAILED DESCRIPTION OF THE INVENTION

Figure 1:
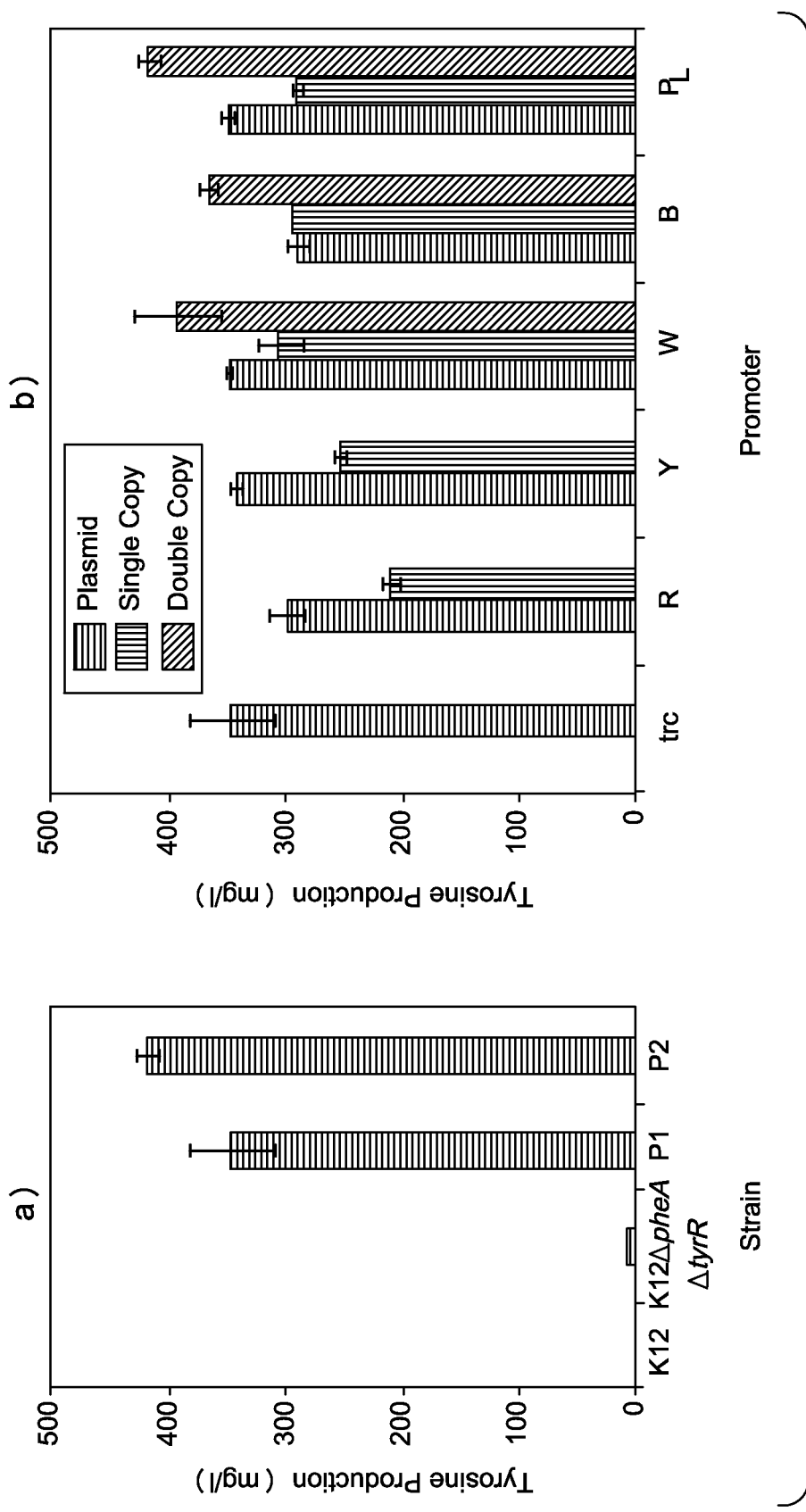
FIG. 1. L-tyrosine production of rationally engineered strains after 24 hr. a) L-tyrosine production of wild-type *E. coli* K12, a double deletion mutant (*E. coli* K12 ΔpheA ΔtyrR), and two parental strains (P1, plasmid-based parental and P2, chromosomal-based parental). b) L-tyrosine production of *E. coli* K12 ΔpheA ΔtyrR strains containing plasmid-based overexpression of the tyrA$^{fbr}$-aroG$^{fbr}$ operon (left bar in each grouping), a single integrated copy (middle bar in each grouping of three bars and right bar in each grouping of two bars), or two chromosomal copies (right bar in each grouping or three bars). Plasmid-based copies of tyrA$^{fbr}$aroG$^{fbr}$ under the control of the synthetic constitutive promoters (R, Y, W, B, were provided on pZE-kan$^{FRT}$-tyrA$^{fbr}$aroG$^{thr}$. Plasmid-based trc expression was driven by pCL1920::tyrA$^{fbr}$aroG$^{fbr}$ FIG. 2. Structure and DNA interactions of RNA polymerase. The RNA polymerase holoenzyme Is composed of the following subunits: $\alpha_2\beta\beta'\omega$. The C-terminal domain of the α subunit (αCTD) is capable of influencing promoter specificity through its interactions with upstream promoter (UP) elements and other activator/repressor proteins (not shown). *E. coli*'s seven sigma factors also control transcription through their interactions with the −35 and −10 regions of promoters.

Here, we describe the use of global transcription machinery engineering (gTME) (Alper and Stephanopoulos 2007) to identify mutants capable of high levels of L-tyrosine synthesis. Three specific mutants—rpoD3, rpoA14, and rpoA27—were isolated which exhibited L-tyrosine titers of up to about 900 mg/L (representing a yield of 0.18 g L-tyrosine/g glucose). A detailed characterization of these three strains by both transcriptional analysis and whole genome sequencing revealed that the overexpression of two specific pathway regulators (EvgA for acid resistance, RelA for stringent response) and the introduction of three individual substitutions (L82R in HisH, V5G in PurF, and T→C nucleotide substitution 17 bp upstream of the purF gene) could successfully impart this L-tyrosine overproduction phenotype. As such, they represent important new targets for engineering this property into other strains. Significantly, this information was also used for the construction of a completely genetically defined organism (with no unknown mutations) capable of producing high levels of L-tyrosine.

Strains isolated from this study exhibited a yield on glucose that was more than 150% greater than a classically improved strain (DPD4195) currently being used for the industrial production of L-tyrosine (Olson, Templeton et al. 2007). When excluding glucose consumption for biomass formation, this yield represents 85% of the maximum theoretical. In addition, the identified targets and mutations have not been previously implicated for L-tyrosine production and therefore present new routes for engineering these strains.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Combinations of a mutant genes or gene products can be expressed in a cell to provide increased production of L-tyrosine. In some embodiments, the cell expresses a gene encoding an alpha subunit of RNA polymerase that includes comprises one or more mutations that results in a helical destabilization or deletion of the C-terminal domain of the α-subunit of RNA polymerase (rpoA αCTD). Specific examples include mutations of amino acid residues V257 and/or L281 of RpoA, such as V257F, V257R and L281P. In some embodiments, the cell expresses a gene encoding a sigma factor gene that includes a truncation. Specific examples include truncation of the nucleotide sequence of rpoD that produces a nucleotide sequence that encodes Region 4 and the end of Region 3 of RpoD protein, such as a deletion of the first 1512 base pairs of E. coli K12 rpoD or 756 amino acids of E. coli K12 RpoD protein. In some embodiments, the cell expresses a hisH gene that includes one or more mutations, such as mutations of the nucleotide sequence of hisH encoding amino acid residue L82, more specifically L82R. In some embodiments, the cell expresses a purF gene that includes one or more mutations, such as mutations of the nucleotide sequence of purF encoding amino acid residue V5, more specifically V5G. In some embodiments, the cell expresses a purF gene that includes one or more mutations, such as a mutation in purF that includes a T→C nucleotide substitution 17 base pairs upstream of the purF gene.

In some embodiments, genes or gene products are overexpressed to contribute to the increased production of L-tyrosine. For example, increased expression, relative to a parental strain, of one or more of evgA, relA, gadA, gadB, gadC, gadE, hdeA, hdeB, hdeD, and/or slp contributes to the increased production of L-tyrosine.

As one of ordinary skill in the art would be aware, homologous genes for these enzymes can be obtained from other species and can be identified by homology searches, for example through a protein BLAST search, available at the National Center for Biotechnology Information (NCBI) internet site (www.ncbi.nlm.nih.gov). Genes associated with the invention can be cloned, for example by PCR amplification and/or restriction digestion, from DNA from any source of DNA which contains the given gene. In some embodiments, a gene associated with the invention is synthetic. Any means of obtaining a gene encoding for an enzyme associated with the invention is compatible with the instant invention.

Aspects of the invention include strategies to optimize production of L-tyrosine from a cell. Optimized production of L-tyrosine refers to producing a higher amount of L-tyrosine following pursuit of an optimization strategy than would be achieved in the absence of such a strategy. Optimization of production of L-tyrosine can involve modifying a gene encoding for an enzyme before it is recombinantly expressed in a cell. In some embodiments, such a modification involves codon optimization for expression in a bacterial cell. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene encoding for an enzyme before it is recombinantly expressed in a cell involves making one or more mutations in the gene encoding for the enzyme before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the enzyme, such as a substitution or deletion of one or more amino acids.

In some embodiments, random mutagenesis is used for producing mutations in enzymes. As described in Example 2, improved L-tyrosine production was achieved in part through random mutagenesis of rpoA and rpoD. In addition, saturation mutagenesis of specific amino acid residues was performed by constructing a saturation mutagenesis library to introduced degenerate bases into the codon positions and screening for increased L-tyrosine production as manifested by, e.g., increased L-tyrosine titer or rate of L-tyrosine production. This process led to the identification of a mutant strain, denoted rpoA22-sm, that was found to contain a V257R substitution in its α subunit (RpoA) protein sequence.

It should be appreciated that the choice of mutations and expression levels of gene products will in some instances depend on the desired end product. For example, some mutations or combinations of mutations may be selected because they lead to an overall increase in L-tyrosine production, while other mutations or combinations of mutations may be selected because they lead to an increase rate of production of L-tyrosine or yield from a particular feedstock or carbon source, such as glucose.

In some embodiments, it may be advantageous to use a cell that has been optimized for production of L-tyrosine. The cells described herein can be used as the basis for additional improvements to L-tyrosine production.

Additional changes can include increasing copy numbers of the components of pathways active in L-tyrosine production, such as by additional episomal expression. In some embodiments, screening for mutations in components of the L-tyrosine production, or components of other pathways, that lead to enhanced production of L-tyrosine may be conducted through a random mutagenesis screen, or through screening of known mutations. In some embodiments, shotgun cloning of genomic fragments could be used to identify genomic regions that lead to an increase in production of L-tyrosine, through screening cells or organisms that have these fragments for increased production of L-tyrosine. In some cases one or more mutations may be combined in the same cell or organism.

In some embodiments, production of L-tyrosine in a cell can be increased through manipulation of enzymes that act in the same pathway as the enzymes associated with the invention. For example, in some embodiments it may be advantageous to increase expression of an enzyme or other factor that acts upstream or downstream of a target enzyme such as an enzyme associated with the invention. This could be achieved by over-expressing the upstream or downstream factor using any standard method. An example of this is the overexpression of evgA and/or relA can be performed based on the identification of pathways having altered levels of expression or regulation based on the gTME methods described herein. Further, expression of other gene products in the pathways of evgA and relA, such as gadA, gadB, gadC, gadE, hdeA, hdeB, hdeD, and/or slp, also can be manipulated to increase production of L-tyrosine.

A further strategy for optimization of protein expression is to increase expression levels of one or more genes associated with the invention through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops.

The invention also encompasses isolated polypeptides containing mutations in residues described herein, and isolated nucleic acid molecules encoding such polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

Amino acid residue numbers indicated herein for polypeptides are based on amino acid numbers in the full-length, wild-type *E. coli* K12 polypeptide (or nucleotide sequence). One of ordinary skill in the art would understand, based on protein alignments between an *E. coli* K12 polypeptide (or nucleotide sequence) and a polypeptide (or nucleotide sequence) from other species, how to determine equivalent residues in other species. Isolated polypeptides from species other than *E. coli* K12, with mutations in residues that are equivalent to the *E. coli* K12 residues described above, are also encompassed by the invention.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

The invention encompasses any type of cell that recombinantly expresses genes associated with the invention, including prokaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*.

It should be appreciated that some cells compatible with the invention may express an endogenous copy of one or more of the genes associated with the invention as well as a recombinant copy. In some embodiments, if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of L-tyrosine.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of L-tyrosine, is demonstrated in the Examples using *E. coli*. The novel method for producing L-tyrosine can also be expressed in other bacterial cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal, including MOPS minimal medium, R minimal medium and M9 minimal medium) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of L-tyrosine. In some embodiments the concentration and amount of a supplemental component may be optimized. In some embodiments, how often the media is supplemented with one or more supplemental components, and the amount of time that the media is cultured before harvesting L-tyrosine, is optimized.

In some embodiments the temperature of the culture may be between 25 and 40 degrees. For example it may be 25, 26, 27, 28, 29, 30, 31, 32, 33, 34, 35, 36, 37, 38, 39 or 40 degrees, or any value in between. In certain embodiments the temperature is between 30 and 32 degrees including 30, 31 and 32 and any value in between. As would be understood by one of ordinary skill in the art, the optimal temperature in which to culture a cell for production of L-tyrosine may be influenced by many factors including the type of cell, the growth media and the growth conditions.

Other non-limiting factors that can be varied through routine experimentation in order to optimize production of L-tyrosine include the concentration and amount of feedstock and any supplements provided, how often the media is supplemented, and the amount of time that the media is cultured before harvesting the L-tyrosine. In some embodiments the cells may be cultured for 6, 12, 18, 24, 30, 36, 42, 45, 50, 55, 60, 65, 70, 75, 80, 85, 90, 95, 100, 110, 120, 130, 140, 150, 160 or greater than 160 hours, including all intermediate values. In some embodiments optimal production is achieved after culturing the cells for several days such as 3-4 days. However it should be appreciated that it would be routine experimentation to vary and optimize the above-mentioned parameters and other such similar parameters.

In various embodiments of the invention, it may be desirable to remove one or more plasmids expressing proteins from bacterial strains. For example, plasmids can be cured by culturing selected strain(s) in culture medium that does not contain an antibiotic that is metabolized by a polypeptide encoded by the plasmid (i.e., a selectable marker). This removes the selective pressure for maintaining the plasmid in the selected bacterial strain(s), which facilitates the loss of the plasmid. Colonies of the strain(s) then can be selected and cultured in parallel in media with and without the antibiotic. Colonies that grow only in media without the antibiotic are bacteria that have lost the plasmid expressing the selectable marker. The methods also can include verifying loss of the plasmid by a variety of methods known in the art, such as an inability to amplify the plasmid sequence by polymerase chain reaction (PCR) or a lack of hybridization of nucleic acids from the bacterial strain to one or more probes specific for the plasmid.

It may be advantageous to use bacterial strains that are previously optimized for a predetermined phenotype prior to introducing phenotypic diversity. Thus, in the production of L-tyrosine, rather than starting with a bacterial cell that produces only a small amount of L-tyrosine, one preferentially uses a cell that produces a higher amount of L-tyrosine, more preferably an optimized amount of L-tyrosine. In such cases, introduction of phenotypic diversity, e.g., by gTME, is used to further improve an already-improved phenotype.

The bacterial strains used in the methods can be L-tyrosine production strains. Exemplary L-tyrosine production strains include *Corynebacterium glutamicum* and *Brevibacterium lactofermentum*. As exemplified herein, *E. coli* strains also can be used in the methods of the invention.

The invention also includes bacterial strains and cells identified or produced by any of the methods described herein. The cells are useful for a variety of purposes, including: further strain improvement and industrial production of L-tyrosine.

According to aspects of the invention, high titers of L-tyrosine are produced through the recombinant expression of genes associated with the invention, in a cell. As used herein "high titer" refers to a titer in the milligrams per liter (mg $L^{-1}$) scale or gram per liter (g $L^{-1}$) scale. The titer produced for a given product will be influenced by multiple factors including choice of media. In some embodiments the total L-tyrosine titer is at least 500 mg $L^{-1}$. For example the titer may be at least about 500, 550, 600, 650, 700, 750, 800, 850, 900, 950, 1000, 1050, 1100, 1150, 1200, 1300, 1400, 1500, 1600, 1700, 1800, 1900, 2000 or more than 2000 mg $L^{-1}$ including any intermediate values. Such higher titers include gram per liter (g $L^{-1}$) titers, for example, titers of at least about 2.5, 3.0, 3.5, 4.0, 4.5, 5.0, 5.5, 6.0, 7.0, 8.0, 9.0, 10.0, 11.0, 12.0, 13.0, 14.0, 15.0 or more g $L^{-1}$ including any intermediate values.

According to aspects of the invention, high productivities of L-tyrosine are produced through the recombinant expression of genes associated with the invention, in a cell. As used herein "high productivity" refers to productivity in gram L-tyrosine per liter per hour (g $L^{-1}$ $hr^{-1}$). In some embodiments the total L-tyrosine productivity is at least about 0.10 grams L-tyrosine/liter/hour. For example the productivity may be at least about 0.15, 0.20, 0.25, 0.30, 0.35, 0.40, 0.45, 0.50, 0.55, 0.60, 0.65, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5 L-tyrosine/liter/hour or more including any intermediate values.

According to aspects of the invention, high yields of L-tyrosine are produced through the recombinant expression of genes associated with the invention, in a cell. As used herein "high yield" refers to a yield in the grams L-tyrosine/gram glucose. In some embodiments, the cells of the invention produce a yield of L-tyrosine on glucose of at least 0.16 grams L-tyrosine/gram glucose. For example the yield may be at least about 0.17, 0.18, 0.19, 0.20, 0.21, 0.22, 0.23, 0.24, 0.25, 0.30, 0.35, 0.40, 0.45, 0.50, 0.55, 0.60 g L-tyrosine/g glucose or more including any intermediate values.

The liquid cultures used to grow cells associated with the invention can be housed in any of the culture vessels known and used in the art. In some embodiments large scale production in an aerated reaction vessel such as a stirred tank reactor can be used to produce large quantities of L-tyrosine, which can be recovered from the cell culture.

Another aspect of the invention involves the identification of a novel mutated forms of genes and encoded polypeptides. Such genes and polypeptides include hisH, encoding an imidazole glycerol phosphate synthase subunit, glutamine amidotransferase (functions in histidine biosynthesis) and purF, encoding an amidophosphoribosyl transferase (functions in de novo purine biosynthesis). Specifically, mutation of the nucleotide sequence of hisH in the codon for amino acid residue L82 (*E. coli* K12 hisH), and particularly a L82R mutation, confers on bacterial cells containing the mutation an improved L-tyrosine production phenotype. Likewise, mutation of nucleotide sequence of purF in the codon for amino acid residue V5 (*E. coli* K12 purF), and particularly a V5G mutation, confers on bacterial cells containing the mutation an improved L-tyrosine production phenotype. Finally, a mutation in purF that produces a T→C nucleotide substitution 17 base pairs upstream of the purF gene (*E. coli* K12 purF) confers on bacterial cells containing the mutation an improved L-tyrosine production phenotype. Mutations in hisH and purF genes at analogous positions to those described herein in other bacterial species and strains are expected to have same effects as demonstrated herein.

The novel mutated forms of the hisH and purF genes and encoded polypeptides have been shown to increase L-tyrosine production, particularly in combination with rpoA or rpoD mutants, or in combination with increased expression, relative to a parental strain, of one or more of evgA, relA, gadA, gadB, gadC, gadE, hdeA, hdeB, hdeD, and/or slp. Combining the novel mutated forms of hisH and purF may result in additive or even synergistic effects on L-tyrosine production relative to the effect of one novel mutated form alone.

Vectors including the foregoing nucleic acid molecules also are provided. The vectors can be cloning vectors or expression vectors, as described in more detail elsewhere herein.

Bacterial strains or cells that include the foregoing nucleic acid molecules, polypeptides or vectors (preferably expression vectors) also are provided.

EXAMPLES

Example 1

Rational Engineering of a Parental Strain

Our objective in evaluating combinatorial metabolic engineering techniques is to determine whether such methods can lead to L-tyrosine yields and titers even beyond those realized by exclusively rational constructions. In doing so, we hope to investigate the possibly complementary nature of these orthogonal approaches. To achieve this goal, a clear first step must then be the rational assembly of strains that possess an already elevated capacity for L-tyrosine synthesis. Though already quite competitive in terms of L-tyrosine yields and titers, these strains will then be used as the starting point for evaluating various combinatorial techniques for library generation. There are several successful strategies for boosting L-tyrosine synthesis involving both deregulation of the AAA pathway and enhancement of precursor (PEP, E4P) supplies. In this example, we apply such strategies towards the construction and evaluation of two parental (or starting) strains.
Materials and Methods
Construction of Plasmid-Based Parental Strain E. coli K12 ΔpheA ΔtyrR (T. Lütke-Eversloh and G. Stephanopoulos, unpublished data) was transformed with pCL1920::tyrA$^{fbr}$aroG$^{fbr}$ (Lütke-Eversloh and Stephanopoulos 2007). This strain, which will henceforth be referred to as parental 1 (P1), was used as the starting strain for the creation of transposon mutagenesis libraries.
Cloning of pZE-kan$^{FRT}$-tyrA$^{fbr}$aroG$^{fbr}$ Plasmids Plasmid pCL1920::tyrA$^{fbr}$aroG$^{fbr}$ was used as a template for the amplification of tyrA$^{fbr}$-aroG$^{fbr}$ with Pfu Turbo DNA polymerase (Stratagene) and the following primers: CS114 tyrAfbr sense KpnI (5'-GCT CGG TAC CAT GGT TGC TGA ATT GAC CGC ATT ACG-3'; SEQ ID NO:1) and CS278 aroGfbr anti MluI (5'-CGA CGC GTT TAC CCG CGA CGC GCT TTT ACT G-3'; SEQ ID NO:2). This PCR product was then digested with KpnI and MluI and ligated into five KpnI/MluI digested pZE-gfp plasmids taken from a synthetic constitutive promoter library (Alper, Fischer et al. 2005). The resulting plasmid pZE-tyrA$^{fbr}$aroG$^{fbr}$ consists of five different versions, each corresponding to different promoter strengths (R, Y, W, B, and P$_L$). To construct pZE-kan$^{FRT}$-tyrA$^{fbr}$aroG$^{fbr}$, primers CS279 pKD13 sense SacI (5'-TCC GAG CTC TTG TGT AGG CTG GAG CTG CTT CGA-3'; SEQ ID NO:3) and CS280 pKD13 anti AatII (5'-TCT TAG ACG TCG AAA TTG ATC CGT CGA CCT GCA GTT CGA A-3'; SEQ ID NO:4) were used to amplify an FRT-flanked kanamycin resistance gene (kan) on the plasmid pKD13 (Datsenko and Wanner 2000). After digestion with SacI and AatII, this product was ligated to SacI/AatII digested pZE-tyr A$^{fbr}$aroG$^{fbr}$ and transformed into chemically competent E. coli DH5α cells as described in the protocol. Following transformation, all plasmid constructs were isolated, verified by sequencing, and transformed into E. coli K12 ΔpheA ΔtyrR. All enzymes used in the cloning procedure were purchased from New England Biolabs.
Chromosomal Integration of tyrA$^{fbr}$-aroG$^{fbr}$ Cassette The kan$^{FRT}$-tyrA$^{fbr}$-aroG$^{fbr}$ cassette was integrated into the lacZ locus of E. coli K12 ΔpheA ΔtyrR using a lambda-red recombination based method (Datsenko and Wanner 2000). Briefly, kan$^{FRT}$-tyrA$^{fbr}$-aroG$^{fbr}$ was amplified from pZE-kan$^{FRT}$-tyrA$^{fbr}$aroG$^{fbr}$ with primers CS173 aroG-lacZ anti (5'-TTC CGG CAC CAG AAG CGG TGC CGG AAA GCT GGC TGG AGT GCG ATC TTC CTG AGG CCG ATA CTG TCG TCG TCC CCT TTA CCC GCG ACG C-3'; SEQ ID NO:5) and CS281 pKD13-lacZ sense (5'-CGC GTG CAG CAG ATG GCG ATG GCT GGT TTC CAT CAG TTG CTG TTG ACT GTA GCG GCT GAT GTT GAA CTG GAA GTC GTG TAG GCT GGA GCT GCT TCG A-3'; SEQ ID NO:6) and Platinum Pfx DNA polymerase (Invitrogen). Both primers incorporated 75-77 bp of homology with the ends of the lacZ gene to facilitate integration into the proper locus. Following transformation of the cassette into E. coli K12 ΔpheA ΔtyrR pJM12 (a pKD46 derivative) colonies were verified by colony PCR and sequencing. Excision of FRT-flanked kan was mediated by transformation with FLP recombinase-expressing pCP20 as described in the literature (Datsenko and Wanner 2000). Five versions of E. coli K12 ΔpheA ΔtyrR lacZ::tyrA$^{fbr}$aroG$^{fbr}$ were constructed by this process with each representing different promoter strengths (R, Y, W, B, P$_L$).

To integrate a second tyrA$^{fbr}$-aroG$^{fbr}$ cassette within the tyrR locus, kan$^{FRT}$-tyrA$^{fbr}$-aroG$^{fbr}$ was amplified from pZE-kan$^{FRT}$-tyrA$^{fbr}$aroG$^{fbr}$ (using promoters W, B, and P$_L$ only) with primers CS286 pKD13-tyrR sense (5'-TGC AAT ATC GGG TGC TGA CCG GAT ATC TTT ACG CCG AAG TGC CCG TTT TTC CGT CTT TGT GTC AAT GAT TGT TGA CAG GTG TAG GCT GGA GCT GCT TCG A-3'; SEQ ID NO:7) and CS287 aroG-tyrR anti (5'-TAA TTT AAT ATG CCT GAT GGT GTT GCA CCA TCA GGC ATA TTC GCG CTT ACT CTT CGT TCT TCT TCT GAC TCA GAC CAT TAC CCG CGA CGC GCT TTT ACT G-3'; SEQ ID NO:8). These primers incorporated 77-78 bp of homology with the ends of the tyrR gene to facilitate integration into the proper locus. Following transformation into E. coli K12 ΔpheA ΔtyrR pJM12, verification and excision of kan were performed as described earlier. Integration of a second tyrA$^{fbr}$-aroG$^{fbr}$ cassette into these strains was mediated by P1 transduction (Miller 1992) of lacZ::kan$^{FRT}$-P$_{LtetO-1}$-tyrA$^{fbr}$aroG$^{fbr}$ from the previously constructed strain E. coli K12 ΔpheA ΔtyrR lacZ::kan$^{FRT}_{LtetO-1}$-tyrA$^{fbr}$aroG$^{fbr}$. Selection on kanamycin, verification, and subsequent kan excision resulted in three separate versions of E. coli K12 ΔpheA ΔtyrR lacZ::tyrA$^{fbr}$aroG$^{fbr}$tyrR::tyrA$^{fbr}$aroG$^{fbr}$. All three strains contain a P$_L$ promoter at the lacZ locus and the promoters R, B, or P$_L$ at the tyrR site. The strain E. coli K12 ΔpheA ΔtyrR lacZ::P$_{LtetO-1}$-tyrA$^{fbr}$aroG$^{fbr}$tyrR:: P$_{LtetO-1}$-tyrA$^{fbr}$aroG$^{fbr}$ (which makes use of the highest strength promoter, P$_L$, for both cassettes) will henceforth be referred to as parental strain 2 (P2).
Cultivation Conditions L-tyrosine production experiments were performed at 37° C. with 225 rpm orbital shaking in 50 ml MOPS minimal medium (Teknova) (Neidhardt, Bloch et al. 1974) cultures supplemented with 5 g/l glucose and an additional 4 g/l NH$_4$Cl. All liquid cultivations were conducted in at least triplicates. When appropriate, antibiotics were added in the following concentrations: 50 μg/ml spectinomycin for maintenance of pCL-1920::tyrA$^{fbr}$aroG$^{fbr}$ and 20 μg/ml kanamycin for maintenance of pZE-derived plasmids. Isopropyl-β-D-thiogalactopyranoside (IPTG) (EMD Chemicals) was added at a concentration of 2 mM for the induction of pCL1920::tyrA$^{fbr}$aroG$^{fbr}$. For L-phenylalanine auxotrophs (ΔpheA), L-phenylalanine (Sigma) was supplied at a concentration of 0.35 mM.
Analytical Methods For the quantification of L-tyrosine, cell-free culture supernatants were filtered through 0.2 μm PTFE membrane syringe filters (VWR International) and used for HPLC analysis with a Waters 2690 Separations module connected with a Waters 996 Photodiode Array detector set to a wavelength of 278 nm. The samples were separated on a Waters Resolve C18 column with 0.1% (vol/vol) trifluoroacetic acid (TFA) in water (solvent A) and 0.1% (vol/vol) TFA in acetonitrile (solvent B) as the mobile phase. The following gradient was used at a flow rate of 1 ml/min: 0 min, 95% solvent A+5% solvent B; 8 min, 20% solvent A+80% solvent B; 10 min, 80% solvent A+20% solvent B; 11 min, 95% solvent A+5% solvent Results Previous studies have demonstrated that significant gains in L-tyrosine titer can be achieved from simple AAA pathway deregulation (Lütke-Eversloh and Stephanopoulos 2007). We therefore decided to use these principles to guide the genetic construction of two parental L-tyrosine producers. Specifically, we chose to incorporate three important genetic modifications: 1) deletion of tyrR to circumvent transcriptional regulation, 2) deletion of pheA to eliminate the loss of AAA pathway intermediates to competing reactions, and 3) overexpression of feedback resistant derivatives of DAHP synthase (aroG) and CM/PDH (tyrA) to increase flux through the AAA pathway.

Plasmid-Based Overexpression of tyrA$^{fbr}$ and aroG$^{fbr}$

Our initial approach to strain construction was to supply feedback-resistant versions of aroG and tyrA on a low (~5) copy plasmid. Plasmid-based overexpression can be quite advantageous, not only because of its genetic simplicity, but also because it allows for the introduction of multiple copies of a gene within a cell. This is oftentimes an important consideration, particularly if the expressed gene represents a critical bottleneck in a process or pathway. To this end, we decided to make use of a previously constructed plasmid (pCL1920::tyrA$^{fbr}$aroG$^{fbr}$) which contained tyrA$^{fbr}$ and aroG$^{fbr}$ under the control of an IPTG-inducible trc promoter. Although its functionality was recently demonstrated in an *E. coli* K12 ΔtyrR background (Lütke-Eversloh and Stephanopoulos 2007), we opted to test its utility in a L-phenylalanine auxotroph (*E. coli* K12 ΔpheA ΔtyrR) to eliminate the loss of AAA pathway intermediates (prephenate) for L-phenylalanine production.

As expected, these simple genetic modifications had a significant impact on extracellular accumulation of L-tyrosine in the medium. Although deletion of tyrR and pheA together only brought nominal increases in L-tyro sine titer (from non-detectable levels in wild-type *E. coli* K12 to 6 mg/l in a ΔpheA ΔtyrR background), combining these deletions with the overexpression of feedback-resistant DAHP synthase and CM/PDH resulted in titers as high as 347 mg/l (FIG. 1a). This engineered strain, named parental 1 (P1, *E. coli* K12 ΔpheA ΔtyrR pCL1920::tyrA$^{fbr}$aroG$^{fbr}$), was used as a plasmid-based parental for the generation of random knockout libraries.

Chromosomal Integration of tyrA$^{fbr}$ and aroG$^{fbr}$

Because traceability for combinatorial engineering methods often depends on the use of antibiotic resistance and plasmid-based expression, marker and plasmid origin incompatibilities can sometimes arise between hosts and implements. To circumvent such problems, we decided to construct a second marker- and plasmid-free parental strain by chromosomal integration of a constitutively-expressed tyrA$^{fbr}$-aroG$^{fbr}$ operon into an *E. coli* K12 ΔpheA ΔtyrR background. As an added advantage of this genetic scheme, this strain can be cultivated in media without antibiotics or inducers, thus transforming its fermentation into a simpler and more economical process.

Our first goal in constructing this strain was to transfer transcriptional control of tyrA$^{fbr}$ and aroG$^{fbr}$ from an inducible trc promoter to one capable of constitutive overexpression. Rather than selecting a single bacterial promoter, we decided to utilize a recently constructed synthetic library of constitutive promoters capable of directing a wide range of expression levels (Alper, Fischer et al. 2005). This additional tunable parameter allowed us to explore whether different expression strengths would have a measurable influence on cellular phenotype. The specific promoters tested and their relative strengths are listed in Table 1.1.

TABLE 1.1

Relative strengths of five synthetic constitutive promoters

| Promoter | Average promoter strength metric (0 to 1)$^a$ |
|---|---|
| R | 0.14 |
| Y | 0.31 |
| W | 0.54 |
| B | 0.82 |
| P$_L$ | 0.87 |

$^a$ data provided by C. Fischer

Interestingly, we observed that integration of only a single copy of tyrA$^{fbr}$ and aroG$^{fbr}$ into the lacZ locus led to lower L-tyrosine titers when compared to our inducible, plasmid-based parental, P1 (FIG. 1b). This trend held for all constitutive promoters tested with the weakest promoters, R and Y, exhibiting the lowest titers. To validate the functionality of our constitutively expressed operons, we decided to measure L-tyrosine production in strains bearing plasmid-based constructs (*E. coli* K12 ΔpheA ΔtyrR pZE-kan$^{FRT}$tyrA$^{fbr}$aroG$^{fbr}$). Because appropriately high L-tyrosine levels were seen for all five versions of pZE-kan$^{FRT}$-tyrA$^{fbr}$aroG$^{fbr}$ (corresponding to the five promoters), we hypothesized that the poor performance of the single integration strains may have resulted from differences in gene dosage and copy number (FIG. 1b).

A Second Copy of tyrA$^{fbr}$aroG$^{fbr}$ is Required for Higher L-Tyrosine Titers In an effort to boost L-tyrosine production, we decided to integrate a second copy of tyrA$^{fbr}$-aroG$^{fbr}$ into the tyrR locus of *E. coli* K12 ΔpheA ΔtyrR lacZ::P$_{LtetO-1}$-tyrA$^{fbr}$aroG$^{fbr}$ using the three strongest promoters, W, B, and P$_{LtetO-1}$. Consistent with our previous theory, the presence of a second copy improved final L-tyrosine titers to levels even beyond those seen with P1 (FIG. 1b). Because no clear trends were seen between L-tyrosine production and the promoter strength of the second operon, it is reasonable to assume that DAHP synthase and CM/PDH no longer exist as the major bottlenecks of the AAA pathway. Nevertheless, we opted to select the strain with the strongest promoter (P$_L$) at the tyrR locus as the second parental strain (P2) for these studies. P2 (*E. coli* K12 ΔpheA ΔtyrR lacZ::P$_{LtetO-1}$-tyrA$^{fbr}$aroG$^{fbr}$tyrR::P$_{LetO-1}$-tyrA$^{fbr}$aroG$^{fbr}$), which requires no antibiotic selection and no induction, was used as the starting strain for the generation of all gTME-derived libraries.

The Advantages of L-Phenylalanine Auxotrophy

With the exception of an additional pheA deletion, our plasmid-based parental strain, P1, is a very similar construction to another strain assembled in our lab (*E. coli* K12 ΔtyrR pCL1920::tyrA$^{fbr}$aroG$^{fbr}$ (Lütke-Eversloh and Stephanopoulos 2007). However, titers from P1 are almost three-fold higher than those previously reported for this strain (347 mg/l versus 127 mg/l), demonstrating the importance of eliminating the prephenate-utilizing competing reaction in this particular background. Surprisingly, we see that these gains are lost once DAHP synthase and CM/PDH levels are increased (by promoter replacement to form T1), with L-tyrosine titers reaching 346 mg/l in a L-phenylalanine prototroph. Thus, it seems that high expression of tyrA is sufficient for diverting flux of prephenate away from L-phenylalanine production, even with an intact CM/PDT in place.

Despite this apparent loss of benefit, we decided to continue our work in a L-phenylalanine auxotroph for a number of reasons. First, even small percentages of L-phenylalanine produced at a large industrial scale can be economically unfavorable, not only because of precursor consumption but also due to the added costs of downstream processing and separation. Although reports have shown that L-phenylalanine synthesis can still occur nonenzymatically in auxotrophic strains (Sariaslani 2007; Patnaik, Zolandz et al. 2008), levels would undoubtedly be higher in the presence of an intact pheA. Secondly, L-phenylalanine auxotrophy can be used quite advantageously to control and limit biomass formation. Although L-tyrosine production has long been known to be associated with exponential growth, a strict conflict still exists between biomass formation and product synthesis, as both processes compete for limited supplies of carbon substrates. The ability to control the amount of L-phenylalanine supplemented at the beginning of the culture allows one to select and predetermine a minimum amount of biomass needed to convert the carbon source to product efficiently.

Avoiding Network Rigidity

In designing our parental strains, we chose to focus only on genetic modifications that would deregulate the AAA pathway despite growing evidence of the importance of modulating precursor availability. This strategy was taken to avoid imposing too much rigidity into the metabolic network. Although maximizing the capacity of the main biosynthetic pathway is clearly a necessary first step, modulating precursor production and utilization may work to our disadvantage by forcing a cell into a particular metabolic state. Such stringency may ultimately limit the capabilities of combinatorial approaches for modulating and accessing a wide range of cellular states and phenotypes. Despite these self-imposed limitations, our rationally constructed strains still exhibited competitive titers and yields. The development of these two parental strains therefore puts us in an excellent position to explore combinatorial engineering strategies for their potential to further enhance these desired properties.

Example 2

Global Transcription Machinery Engineering Search

Although greedy search algorithms (sequential target identification) can be used to identify mutations with positive additive effects on cellular phenotype, they are unable to access cellular properties requiring the simultaneous modulation of an entire subset of genes. Fortunately, the recently developed technique of global transcription machinery engineering (gTME) lends itself quite nicely for this purpose.

gTME is a unique tool capable of altering the cellular transcriptome on a global level. Such a task is enabled through the targeted mutagenesis (via error prone PCR) of proteins that are known to influence gene transcription by the RNA polymerase holoenzyme (Alper and Stephanopoulos 2007). In this example, we focus on the mutagenesis of two subunits of the RNA polymerase—rpoD-encoded $\sigma^{70}$ and the rpoA-encoded α subunit—for engineering novel cellular properties.

Structure of RNA Polymerase and Determinants of Specificity

Figure 2:
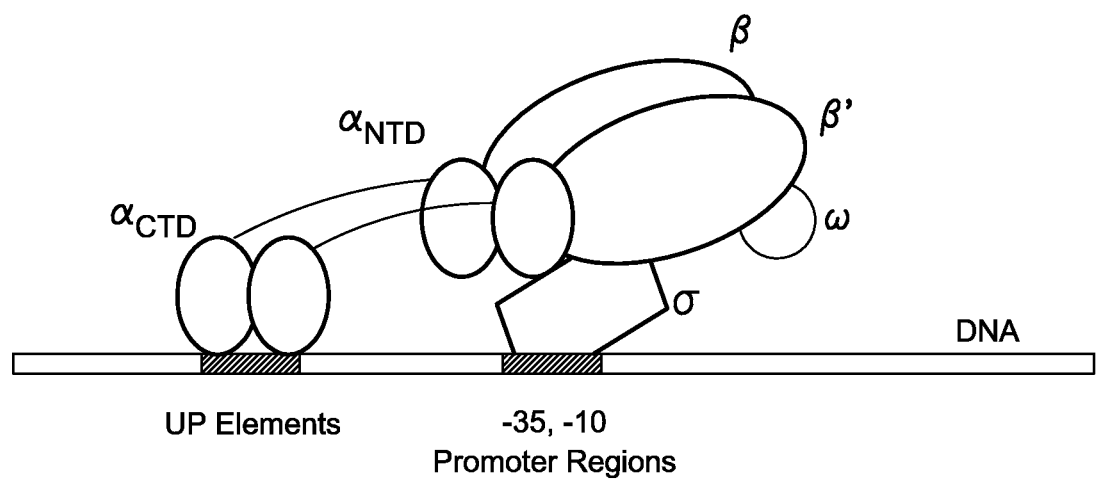

RNA polymerase is a multi-subunit complex that directs and regulates transcription in prokaryotes. The core enzyme, which is comprised of the subunits $\alpha_2\beta\beta'\omega$, is capable of carrying out all stages of transcription except for the process of initiation. This first stage requires binding to one of E. coli's seven sigma factors, each of which is active and preferred during distinct environmental or cellular conditions (FIG. 2) (Browning and Busby 2004). Despite this specificity, however, all sigma factors proceed with the same mechanism: through their interactions with the −35 and −10 sequences, sigma factors bind and preferentially recruit the RNA polymerase holoenzyme to the promoters of a distinct set of genes. It is because of this direct role in promoter recognition and binding that sigma factors were selected as initial targets for transcriptional mutagenesis (Alper and Stephanopoulos 2007; Klein-Marcuschamer and Stephanopoulos 2008). In this example, we build upon this previous work and explore the use of $\sigma^{70}$ (the main housekeeping sigma factor in E. coli) for improving L-tyrosine production in E. coli.

Although sigma factors are often recognized as the primary determinants of promoter specificity, the rpoA-encoded α subunit of RNA polymerase has also been implicated in promoter recognition. In particular, its C-terminal domain (denoted αCTD) has been shown to interact not only with upstream promoter (UP) enhancer elements of the DNA, but also with several activator and repressor proteins (FIG. 2) (Ross, Gosink et al. 1993; Gaal, Ross et al. 1996; Browning and Busby 2004; Dangi, Gronenborn et al. 2004). As an added benefit, because the α subunit is part of the core enzyme, it has the potential to change the RNA polymerase's promoter affinities regardless of which of the seven sigma factors is bound (and hence, under all environmental conditions) (Ishihama 2000; Jishage, Kvint et al. 2002; Browning and Busby 2004). We therefore hypothesized that the α subunit could also be a useful mutagenesis target for engineering L-tyrosine overproduction in our strains.

Materials and Methods

Cultivation Conditions

L-tyrosine production experiments were performed at 37° C. with 225 rpm orbital shaking in 50 ml MOPS minimal medium (Teknova) (Neidhardt, Bloch et al. 1974) cultures supplemented with 5 g/l glucose and an additional 4 g/l NH$_4$Cl. All liquid cultivations were conducted in at least triplicates. When appropriate, antibiotics were added in the following concentrations: 34 μg/ml chloramphenicol for maintenance of pHACM-derived plasmids and 100 μg/ml ampicillin for maintenance of pTrcme/A$^{mut1}$. Isopropyl-β-D-thiogalactopyranoside (IPTG) (EMD Chemicals) was added at a concentration of 1 mM for the induction of pTrcmelA$^{mut1}$. For L-phenylalanine auxotrophs (ΔpheA), L-phenylalanine (Sigma) was supplied at a concentration of 0.35 mM.

Generation and Screening of gTME Libraries rpoA and rpoD plasmid libraries were generated as described previously (Alper and Stephanopoulos 2007; Klein-Marcuschamer, Santos et al. 2009). Briefly, fragment mutagenesis was performed on wild-type rpoA or rpoD using the GenemorphII Random Mutagenesis Kit (Stratagene) to induce low (0-4.5 mutations/kb), medium (4.5-9 mutations/kb), and high (9-16 mutations/kb) frequencies of mutation. Following digestion and ligation, preparations of the resulting pHACM-rpoA/rpoD plasmid libraries were then transformed into parental strain P2 to generate rpoA and rpoD mutant strain libraries. Approximately 7.5×10$^5$ and 3.1×10$^6$ viable colonies (for rpoA and rpoD, respectively) were screened using a melanin-based high-throughput assay for L-tyrosine production (Santos and Stephanopoulos 2008).

A saturation mutagenesis library for pHACM-rpoA14 was constructed using the QuikChange Multi Site-Directed Mutagenesis Kit (Stratagene). Primers were designed according to the manufacturer's specifications with degenerate bases substituted into the codon positions corresponding to V257 and L281. This plasmid library was subsequently transformed into a plasmid-cured rpoA14 strain (generated by four rounds of subculturing in LB medium), and approximately 5000 viable colonies were screened for L-tyrosine production (Santos and Stephanopoulos 2008).

Plasmid Curing and Retransformation

To investigate the individual contributions of plasmid-based and chromosomal-based mutations, isolated mutant strains were subcultured in LB medium to promote loss of its corresponding pHACM-derived plasmid. Following 3 to 4 rounds of reinoculation, strains were streaked out on LB-agar plates and checked for the loss of chloramphenicol resistance. Routine chemical transformation protocols were utilized in the construction of strains containing a combination of wild-type or mutant backgrounds and plasmids.

Mutational Analysis of Strains

Mutation frequency analysis protocols were adapted from a previously published report on the use of rpoB to analyze the specificity of base substitutions in *E. coli* (Garibyan, Huang et al. 2003). Briefly, cells were inoculated at a starting $OD_{600}$ of 0.01 and grown for 48 hr in 5 ml LB cultures. After appropriate dilution, cultures were plated on LB-agar with and without 100 µg/ml rifampicin (Sigma). (Dilution is necessary to recover distinct colonies as opposed to lawn growth, with an approximate target of less than 200 colonies per plate). The number of colony forming units (CFUs) on each plate was quantified after 16-20 hr, and average mutation frequencies were determined by dividing the average number of rifampicin-resistant colonies by the average number of CFUs growing on unselective media (LB). At least ten culture and plate replicates were used in this calculation for each strain tested.

dnaQ$^{mut1}$ is a P1 strain background (plasmid-based tyrA and aroG expression) containing a 16 amino acid truncation on the C-terminal end of its dnaQ gene. Details for its construction are as follows: Strain dnaQ$^{mut1}$ was constructed by amplification of kan from pKD13 (Datsenko and Wanner 2000) with primers CS332 dnaQ trunc sense (5' AGT TAC GCG TTG TTT TTG CGA CAG ATG AAG AGA TTG CAG CTC ATG AAG CCT AAG TGT AGG CTG GAG CTG CTT C-3'; SEQ ID NO:9) and CS334 dnaQ trunc anti (5'-GCA AAA ATC GCC CAA GTC GCT ATT TTT AGC GCC TTT CAC AGG TAT TTA TGA TCC GTC GAC CTG CAG TTC GA-3'; SEQ ID NO:10) for the insertion of a stop codon 51 bp from the end of the dnaQ gene. Chromosomal integration of these PCR cassettes into P1 was performed using a lambda-red recombination based method (Datsenko and Wanner 2000). Colonies were verified by colony PCR and sequencing, and excision of FRT-flanked kan was mediated by transformation with FLP recombinase-expressing pCP20 as described in the literature (Datsenko and Wanner 2000).

Analytical Methods

For the quantification of L-tyrosine, cell-free culture supernatants were filtered through 0.2 µm PTFE membrane syringe filters (VWR International) and used for HPLC analysis with a Waters 2690 Separations module connected with a Waters 996 Photodiode Array detector set to a wavelength of 278 nm. The samples were separated on a Waters Resolve C18 column with 0.1% (vol/vol) trifluoroacetic acid (TFA) in water (solvent A) and 0.1% (vol/vol) TFA in acetonitrile (solvent B) as the mobile phase. The following gradient was used at a flow rate of 1 ml/min: 0 min, 95% solvent A+5% solvent B; 8 min, 20% solvent A+80% solvent B; 10 min, 80% solvent A+20% solvent B; 11 min, 95% solvent A+5% solvent B. Cell densities of cultures for growth rate calculations were determined by measuring their absorbance at 600 nm with an Ultrospec 2100 pro UV/Visible spectrophotometer (Amersham Biosciences).

Results

Identification and Performance of Mutant rpoD3

Figure 3:
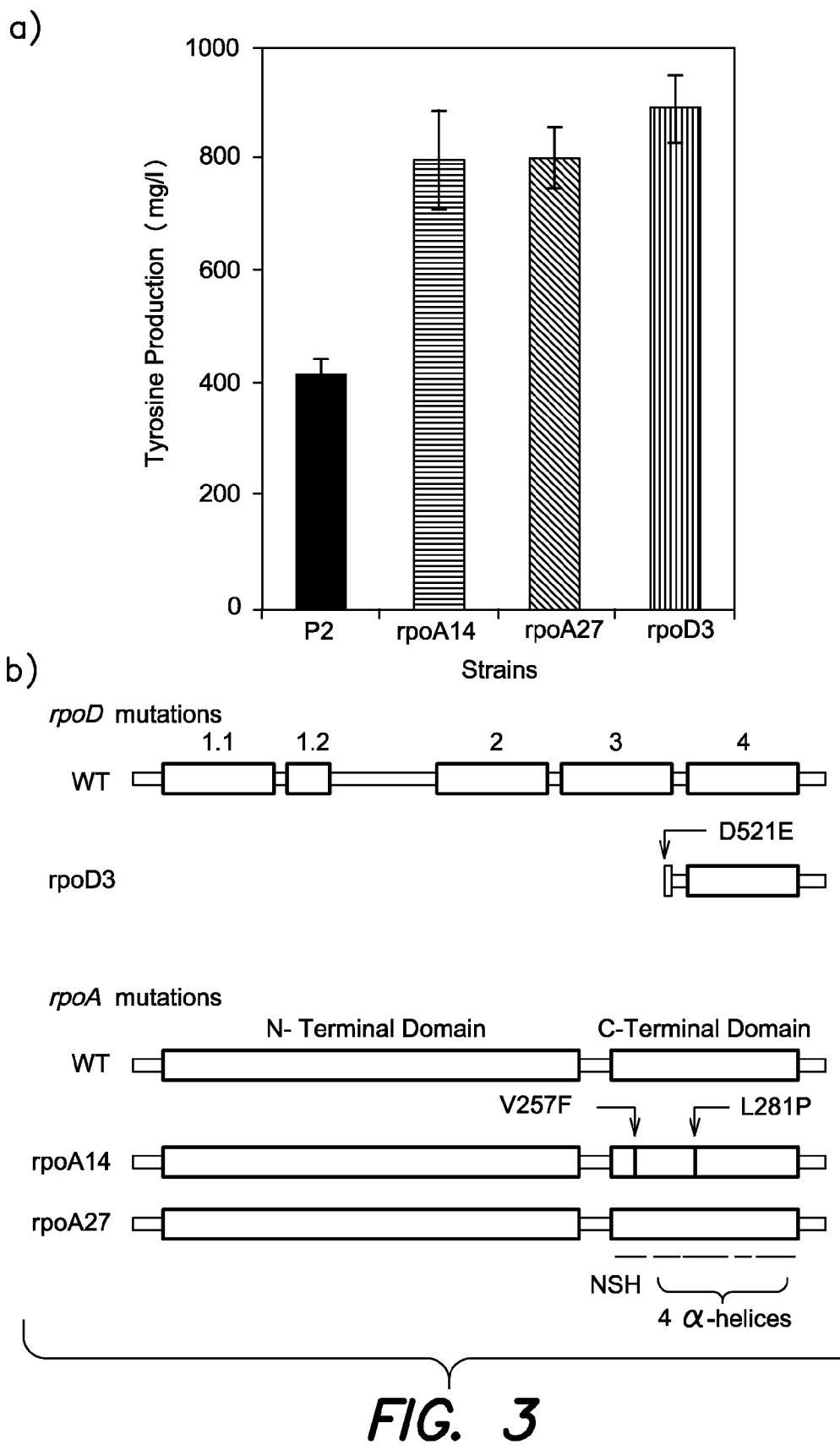
FIG. 3. Properties of mutants isolated from gTME libraries. a) L-tyrosine titers of isolated mutants after 48 hr b) Sequence analysis of plasmid-encoded mutant rpoA and rpoD. Numbers above wild-type rpoD indicate conserved regions of the protein. NSH stands for the "non-standard helix" portion of the α subunit C-terminal domain.
Figure 4:
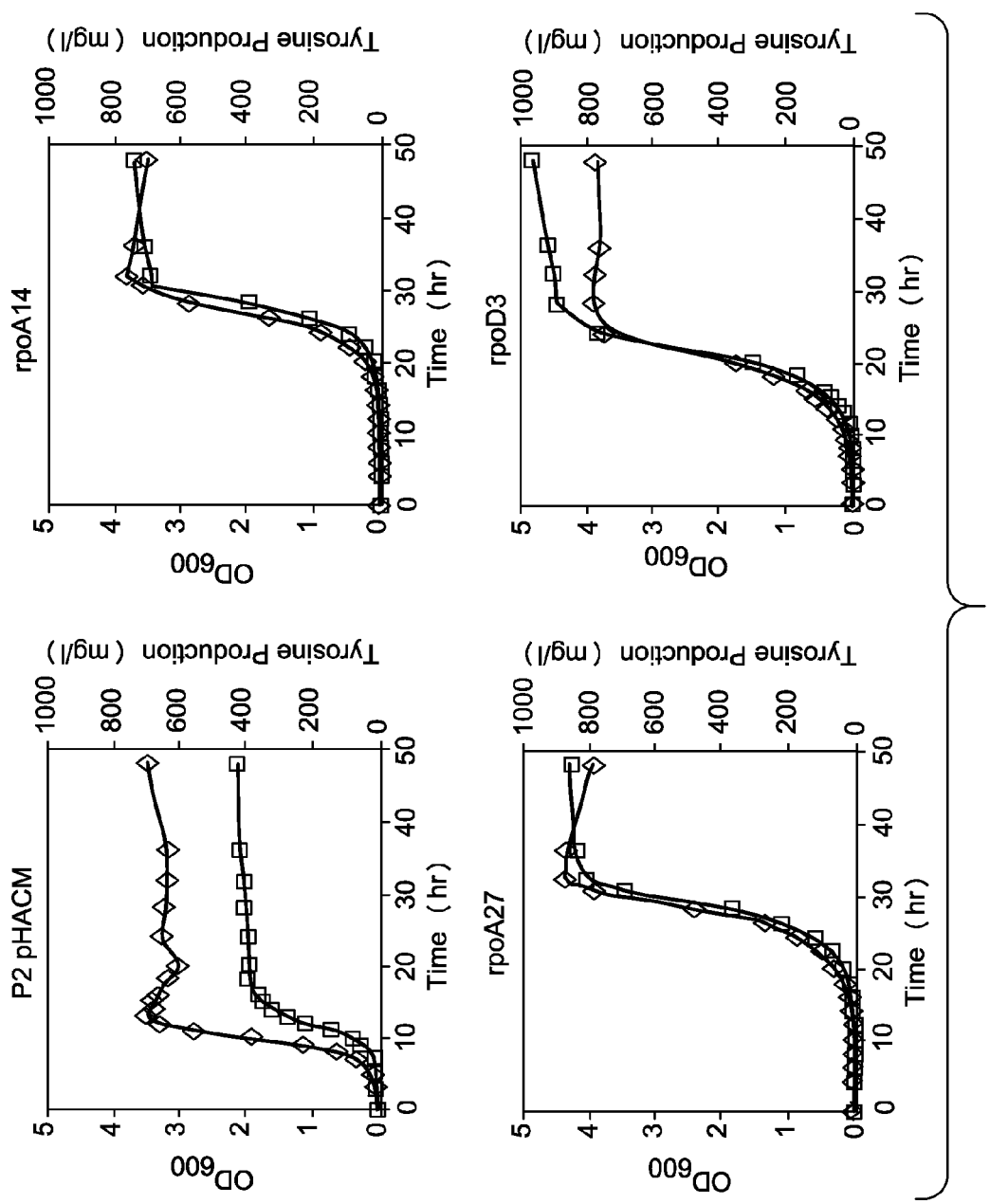
FIG. 4. Representative growth and L-tyrosine production curves for gTME mutants. OD$_{600}$ measurements (diamonds) and L-tyrosine production profiles (squares) for parental P2 with pHACM and three gTME mutants. Specific growth rates for these strains were: 0.617 hr$^{-1}$ (P2 pHACM), 0.296 hr$^{-1}$ (rpoA14), 0.249 hr$^{-1}$ (rpoA27), and 0.290 hr$^{-1}$ (rpoD3).

Because previous studies have demonstrated the effectiveness of modulating $\sigma^{70}$ for eliciting complex phenotypes (Alper and Stephanopoulos 2007; Klein-Marcuschamer and Stephanopoulos 2008), we decided to begin our investigation by creating a library of plasmid-expressed rpoD variants in the background of parental strain P2. Screening of an rpoD mutant library consisting of $3.1 \times 10^6$ viable colonies led to the isolation of a strain possessing significant increases (113%) in L-tyrosine production over P2. This mutant, named rpoD3, exhibited final L-tyrosine titers of 893 mg/l L-tyrosine (FIG. 3). Final concentrations were measured after 48 hr due to the slower growth rate of this strain, although detailed growth and L-tyrosine production curves show that levels remain stable after just 28 hr (FIG. 4)

Sequencing of pHACM-rpoD3 and Structural Analysis of $\sigma^{70}$

The $\sigma^{70}$ protein contains 4 conserved domains (region 1-4), each of which play specific roles in mediating binding to RNA polymerase and to DNA. Interestingly, a sequence analysis of the plasmid-encoded rpoD from mutant rpoD3 revealed a truncated form of this protein consisting of just region 4 and the tail end of region 3 (FIG. 3) Because *E. coli*'s RNA polymerase is a well-studied enzyme, much is actually known about the functional role of $\sigma^{70}$'s fourth conserved domain. Region 4 is made up of four helices which interact with the −35 region of the promoter and additionally contains a major RNA polymerase binding determinant. More recently, this region has also been implicated in the binding of anti-σ factors such as Rsd, which are expressed during stationary phase (Gruber and Gross 2003). As it turns out, anti-σ factors play an important role in regulating the metabolic shift from exponential growth to stationary phase, a function mediated by binding to $\sigma^{70}$ and subsequently blocking its association with the RNA polymerase. It is in this indirect way that anti-σ factors are able to contribute to the preferential use of stationary phase σ factor $\sigma^S$, and, as a result, mediate the transcription of a novel set of genes (Gruber and Gross 2003; Sharma and Chatterji 2008).

Given this information, how then might overexpression of a separate Region 4 domain lead to changes in L-tyrosine production within this mutant strain? One effect may be closely related to its efficient ability to bind Rsd. Truncated sigma factors have previously been shown to possess higher binding affinities to anti-σ factors relative to the full length protein (Sharma, Ravishankar et al. 1999). We hypothesize then that overexpression of a truncated protein could, in essence, titrate high amounts of Rsd from the cytosol, leaving a smaller number of molecules available to bind the chromosomally-expressed and fully functional wild-type form. Fewer Rsd-$\sigma^{70,WT}$ binding events would delay the onset of stationary phase and may ultimately lengthen the exponential growth period during which L-tyrosine is produced. As an alternative hypothesis, the truncated $\sigma^{70}$ may also affect L-tyrosine production through its association with the RNA polymerase core and the subsequent assembly of nonfunctional enzymes. Even a small fraction of unproductive RNA polymerases could ultimately lead to the slower growth rate observed in these cells. This reduced growth may ultimately prove to be beneficial for L-tyrosine production.

Identification and Performance of Mutants rpoA14 and rpoA27

Buoyed by our early success with the use of rpoD mutagenesis, we then turned our attention towards applying the same transcriptional engineering paradigm using a novel genetic target—the RNA polymerase α subunit. In order to properly characterize the potential of this approach, rpoA mutagenesis was evaluated with respect to three different cellular phenotypes—butanol tolerance, hyaluronic acid production, and L-tyrosine production. Specific details regarding the engineering of the first two properties can be found in a recent publication (Klein-Marcuschamer, Santos et al. 2009). In these next few sections, we will discuss the efficacy of an rpoA-mediated transcriptional engineering approach for optimizing the third trait, the overproduction of L-tyrosine. L-tyrosine synthesis in E. coli is a natural platform for which to test this novel method, particularly since transcriptional modifications have already proven to be an effective strategy for eliciting this phenotype.

To begin this investigation, a plasmid-encoded rpoA mutant library was generated by error-prone PCR (Klein-Marcuschamer, Santos et al. 2009) and transformed into parental strain P2. Screening and selection from an initial pool of $7.5 \times 10^5$ mutants led to the identification of two notable strains (denoted rpoA14 and rpoA27) with a 91-93% increase in L-tyrosine titer compared to the parental. Final concentrations of 798 and 806 mg/l L-tyrosine (for rpoA14 and rpoA27, respectively) were reached after 48 hr (FIG. 3), although these high titers and yields were also accompanied with a significantly reduced growth rate (FIG. 4).

Sequence Analysis of pHACM-rpoA14 and pHACM-rpoA27

Sequencing of the mutant plasmid pHACM-rpoA14 revealed the presence of two amino acid substitutions within the αCTD, in close proximity to residues involved with regulatory factor and UP element interactions (Murakami, Fujita et al. 1996). The first change (V257F) occurred in the so-called "non-standard helix", while the other (L281P) was located in one of the four α-helices of the αCTD (FIG. 3) (Gaal, Ross et al. 1996). Because both substitutions reside in secondary structural elements of the protein, it is likely that these mutations have altered the overall αCTD structure and, as a result, its interactions with target proteins and sequences. In particular, the amino acid proline has been shown to lead to α-helix destabilization under certain conditions (Li, Goto et al. 1996). A change in helix conformation could change the relative alignment of amino acids that make contacts with promoters, thus altering the affinity of the RNA polymerase for some of its targets.

Figure 5:
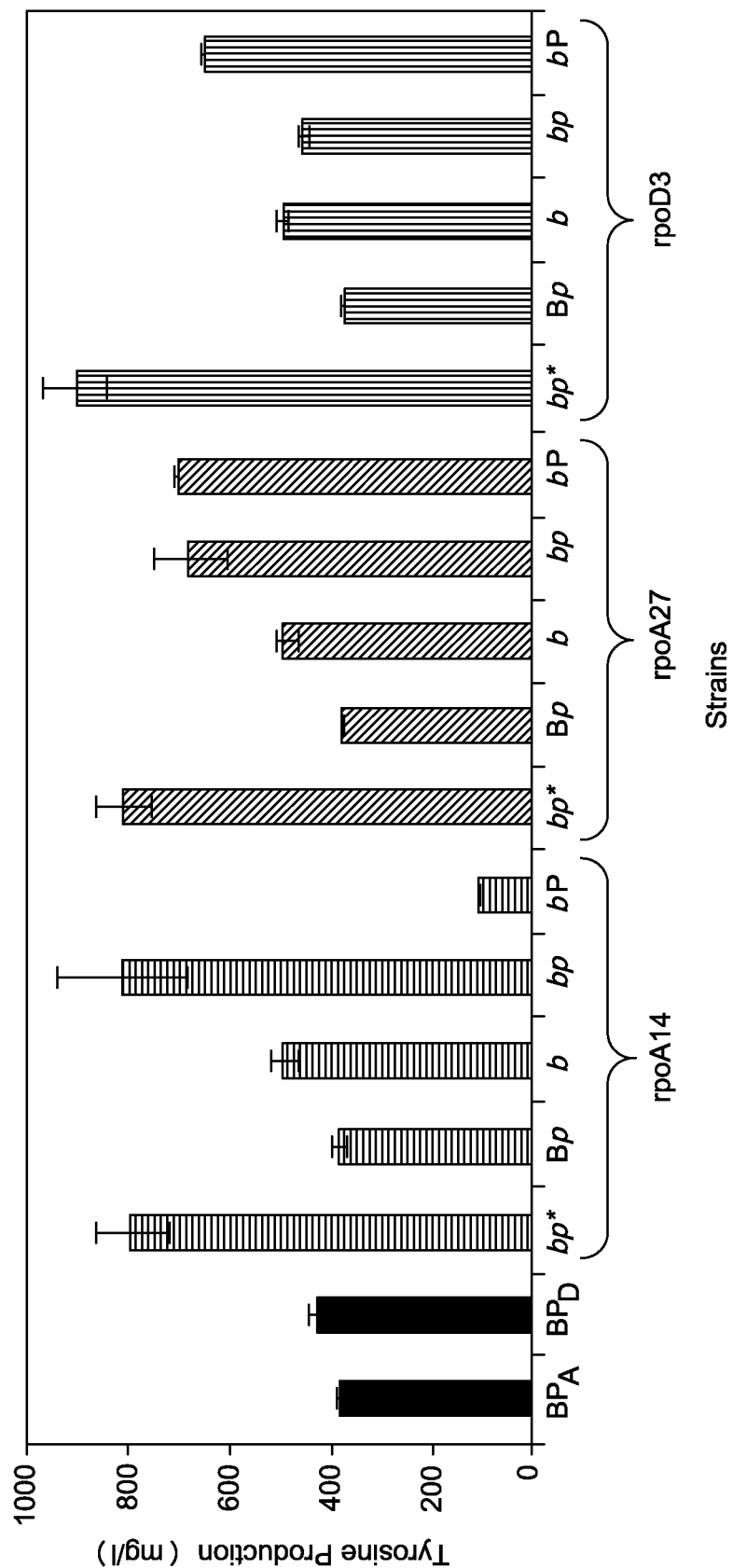
FIG. 5. Both a mutant plasmid and a mutant background are required for a L-tyrosine overproduction phenotype. B=background, P=plasmid; Wild-type versions of the background or plasmid are denoted by uppercase. Mutant versions are denoted by lowercase. P$_A$ and P$_D$ represent the wild-type rpoA and rpoD plasmids, respectively. bp* represents the original strains isolated from the mutant libraries.

Surprisingly, no changes were found in the sequence of pHACM-rpoA27. The recovery of a wild-type plasmid in rpoA27 was quite unexpected, particularly since the overexpression of rpoA by itself does not seem to confer additional advantages in the parental background (FIG. 5). It is possible that other mutations within the chromosome may be either partial or full contributors to the observed phenotype.

High L-Tyrosine Titers are Dependent on Both Plasmid and Background

Because a wild-type plasmid was isolated from the rpoA27 mutant, it seems likely that at least one additional background mutation may be needed to adequately boost the strain's capacity for L-tyrosine production. To determine whether similar conditions were required for the other two gTME mutants, rpoA14 and rpoD3, we decided to verify which specific genetic components (or combinations thereof) serve as the main determinants of phenotype.

We began by first testing whether plasmid transfer into the clean genetic background of parental strain P2 would recover the high L-tyrosine titers observed in our mutants. As we might have suspected, P2 containing pHACM-rpoA27 (which has 100% sequence identity as pHACM-rpoA$^{WT}$) exhibited very similar properties as P2 by itself or with the wild-type rpoA control plasmid. Unexpectedly, however, the same trend held true for both pHACM-rpoA14 and pHACM-rpoD3, plainly indicating that all three recovered mutants require more than just their respective plasmids in order to produce large quantities of L-tyrosine (FIG. 5, $2^{nd}$ bar within each set). It is clear then that additional mutations incurred within their chromosome must offer significant contributions to the dramatic shifts in their cellular states.

To determine whether these unknown chromosomal mutations were single-handedly exerting the desired phenotypic effects, we decided to cure the three isolated strains of their plasmids, leaving us with just a mutant background or chromosome. As shown in FIG. 5 (3rd bar within each set), these plasmid-free strains displayed titers that were only slightly higher than the parental. Thus, these strains exhibit a clear deficit in phenotype associated with the loss of its corresponding mutant plasmid.

Taking these results altogether, it becomes readily apparent that the high L-tyrosine titers observed in our isolated mutants are uniquely dependent on both a mutated pHACM-derived plasmid and a mutant background. Indeed, we found that retransforming pHACM-rpoA14 and pHACM-rpoA27 back into the previously cured strains resulted in complete recovery of the desired phenotype (FIG. 5, $4^{th}$ set of bars within each group). Unusually, this pattern did not hold for rpoD3, with the reconstructed strain exhibiting L-tyrosine titers as low as the parental. This discrepancy may have resulted from additional chromosomal mutational events occurring during the plasmid curing step, which required at least three rounds of subculturing in LB. However, this process was repeated several times with similar results (data not shown), suggesting that rpoD3 may be inherently unstable with regards to the transfer of phenotype. The reason for this instability remains unknown.

As a final control for this experiment, we also wanted to verify that the wild-type rpoA/rpoD plasmid could not supplant the role of their mutant counterparts. As expected, strains comprised of a mutant rpoA14 or rpoD3 background with a wild-type plasmid exhibited reduced L-tyrosine production levels (FIG. 5, last bar within each group). The effect was particularly striking for rpoA14 which produced L-tyrosine at less than 100 mg/l, indicating a substantial need for the mutant version of the plasmid. The only exception was seen for rpoA27, a result that was not at all surprising, given that a wild-type sequence was in fact recovered from this strain (FIG. 3).

Overexpression of rpoA/rpoD does not Induce a Mutator Phenotype

Figure 6:
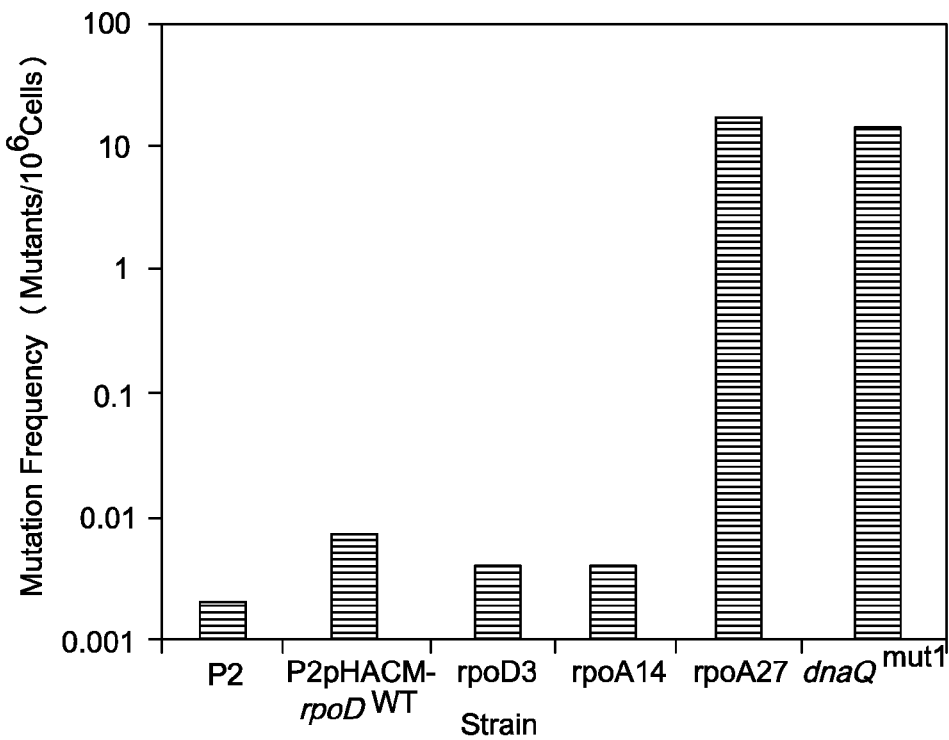
FIG. 6. Mutation frequencies of select strains. Mutation frequencies were measured after 48 hr growth in 5 ml LB. Values for dnaQ$^{mut1}$ were included as a positive control.

Because of the unusually high incidence of chromosomal variation in our strains, we decided to measure mutation frequencies to determine if elevated values could account for the observed discrepancies. To probe this characteristic, we utilized a rifampicin-based mutagenesis assay as described above. However, a longer initial incubation period in LB was incorporated (48 hr) in order to more properly mimic the nutrient-limited conditions that strains would have likely seen during plate selection and screening. For most strains tested, the presence of a wild-type or mutant rpoA/rpoD plasmid did not result in any increases in mutation frequency when compared to parental strain P2. The only exception was seen for the rpoA27 mutant, which had a higher observed frequency of about 16 mutants/$10^6$ cells, a value comparable to that of the dnaQ$^{mut1}$ strain described herein (FIG. 6). These findings clearly indicate the absence of a high mutator phenotype within these isolated strains. We must therefore assume that the high rate of chromosomal variation must have arisen out of a specific requirement for these background mutations in order to generate the desired phenotype. If these mutations are absolutely needed to impart an enhanced capacity for L-tyrosine synthesis, then such mutants, no matter how "rare" an occurrence within the library, would undoubtedly be detected and selected by the high-throughput screen.

Overexpression of rpoA/rpoD does not Induce a Mutator Phenotype

Because of the unusually high incidence of chromosomal variation in our strains, we decided to measure mutation frequencies to determine if elevated values could account for the observed discrepancies. To probe this characteristic, we again utilized a rifampicin-based mutagenesis assay as described above. However, a longer initial incubation period in LB was incorporated (48 hr) in order to more properly mimic the nutrient-limited conditions that strains would have likely seen during plate selection and screening. For most strains tested, the presence of a wild-type or mutant rpoA/rpoD plasmid did not result in any increases in mutation frequency when compared to parental strain P2. The only exception was seen for the rpoA27 mutant, which had a higher observed frequency of about 16 mutants/$10^6$ cells, a value comparable to that of the dnaQ$^{mut1}$ strain described herein (FIG. 6). These findings clearly indicate the absence of a high mutator phenotype within these isolated strains. We must therefore assume that the high rate of chromosomal variation must have arisen out of a specific requirement for these background mutations in order to generate the desired phenotype. If these mutations are absolutely needed to impart an enhanced capacity for L-tyrosine synthesis, then such mutants, no matter how "rare" an occurrence within the library, would undoubtedly be detected and selected by the high-throughput screen.

Saturation Mutagenesis of pHACM-rpoA14 for Improved Productivity

Although significant gains in L-tyrosine titer have already been achieved through both rpoD and rpoA mutagenesis, we were interested in determining whether additional rounds of transcriptional engineering could be further beneficial for this phenotype. However, rather than subjecting the entire locus to error prone PCR as before, we instead restricted our mutagenesis to the two substituted residues found in pHACM-rpoA14. Given their locations within secondary structural components of the αCTD, we hypothesized that these positions may be important determinants of promoter specificity; hence, we were interested in exploring whether other amino acid substitutions within these two sites, V257 and L281, could further enhance L-tyrosine production in these strains.

Figure 7:
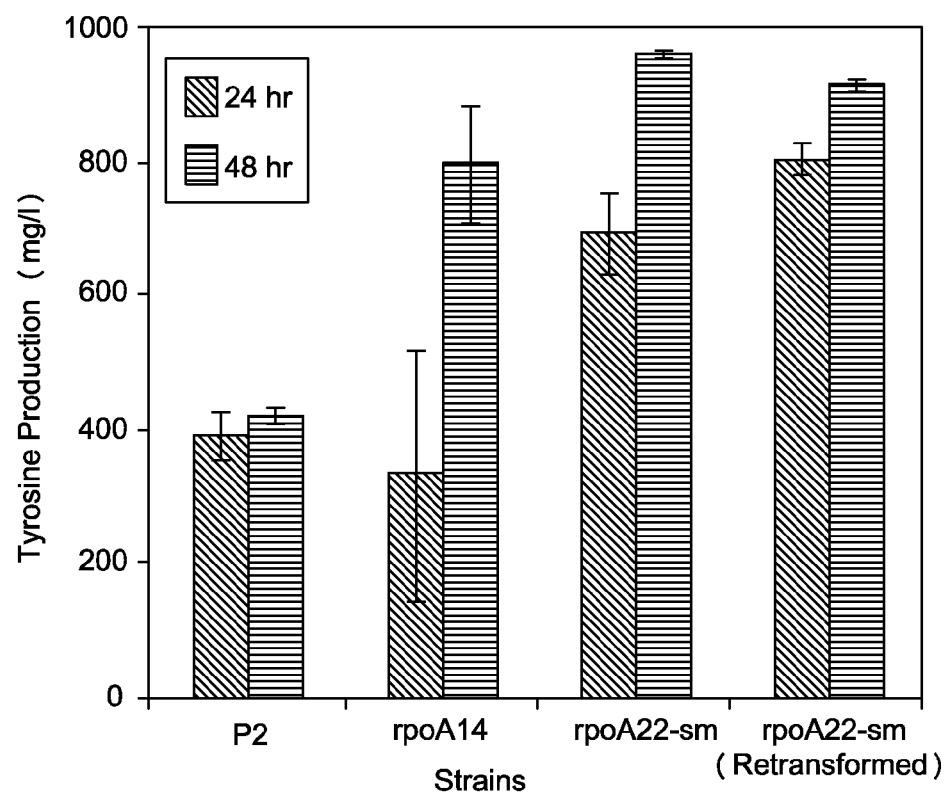
FIG. 7. Performance of strains isolated from a pHACM-rpoA14 saturation mutagenesis library. L-tyrosine titers are shown after 24 hr (left bar in each grouping) and 48 hr (right bar in each grouping). rpoA22-sm-labeled bars represent titers for the original isolate from the saturation mutagenesis library. rpoA22-sm (retransformed) refers to a strain in which the pHACM-rpoA22-sm plasmid was individually isolated and subsequently transformed into a plasmid-free rpoA14 background.

We began this work with the construction of a saturation mutagenesis library for pHACM-rpoA14 which introduced degenerate bases into the codon positions of V257 and L281. The resulting plasmids were then transformed into the cured, plasmid-free version of rpoA14 and screened as before. Our search through a pool of about 5000 viable colonies led to the identification of a mutant strain, denoted rpoA22-sm, that was found to contain a V257R substitution in its α subunit protein sequence. Although this isolate exhibited only a modest increase in L-tyrosine titer compared to mutant rpoA14 (up 20% to 962 mg/l), this was, quite surprisingly, accompanied by a faster rate of L-tyrosine production (FIG. 7). In fact, the recovered mutant was able to produce 72% (~700 mg/l) of the total amount of L-tyrosine after 24 hr of incubation; by comparison, rpoA14 titers during this time point are so low (~330 mg/l) that they remain largely indistinguishable from those of the parental strain P2. The results were even more striking when pHACM-rpoA22-sm was retransformed into a clean rpoA14 background, with this reconstructed strain reaching nearly 90% (~806 mg/l) of its final titer after just 24 hr. These notable differences in productivity are likely a result of a more robust strain constitution, as these strains exhibited a 15% higher growth rate than the library parental, rpoA14 (0.341 hr$^{-1}$ versus 0.296 hr$^{-1}$). Altogether, the enhanced growth and productivity of mutant rpoA22-sm make it a very interesting candidate for developing a continuous process for the production of L-tyrosine.

Mechanistic Insights into rpoA

Although our analysis of the rpoA saturation mutagenesis library focused largely on the characterization of rpoA22-sm, it was interesting to note that almost all mutants subjected to the final round of screening (in 50 ml shake flasks) exhibited titers that were either comparable or higher than the library parental, rpoA14 (data not shown). This unusually high percentage of hits was incongruous with our experiences with previous libraries, suggesting that the specific identities of the amino acid substitutions actually play a limited role in determining phenotype. This then implies that a more general, nonspecific mechanism for rpoA activity may be responsible for the observed gains in L-tyrosine production. One plausible hypothesis is that helical destabilization in αCTD mediated by substitutions at V257 and/or L281 may lead to a misfolding of the C-terminal domain. This generic, partial loss of function in rpoA may be all that is required to impart a L-tyrosine overproduction phenotype.

Figure 8:
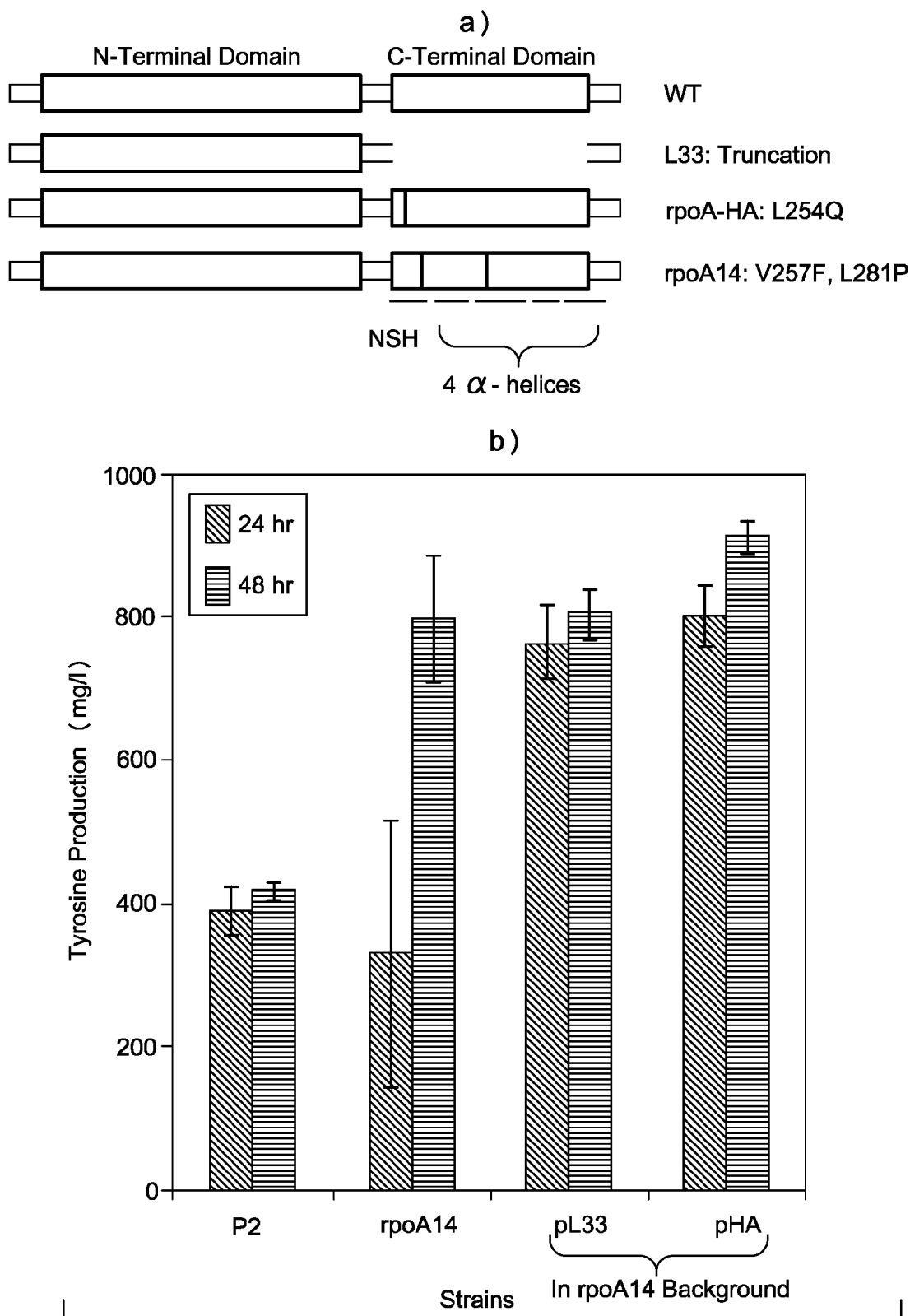
FIG. 8. Performance of cured rpoA14 with αCTD-mutated rpoA variants. a) Schematic of mutant rpoA proteins recovered from strains optimized for three separate phenotypes. L33-butanol tolerance; HA—hyaluronic acid production; rpoA14-L-tyrosine production. b) Plasmids from the mutant strains L33 and rpoA-HA were isolated and transformed into a cured rpoA14 background. L-tyrosine titers were then measured after 24 hr (left bar in each grouping) and 48 hr (right bar in each grouping). Production of L-tyrosine by parental P2 and rpoA14 were also included as a reference.

This notion of rpoA nonspecificity has been recently supported by two other studies that have utilized rpoA transcriptional engineering for optimizing cellular properties (Klein-Marcuschamer, Santos et al. 2009). In the first, an engineered strain capable of high levels of hyaluronic acid production (rpoA-HA) was recovered from a library and shown to possess a L254Q variant of rpoA (FIG. 8a). As with rpoA14's V257F, this amino acid substitution was mapped to the nonstandard helix of αCTD and likely altered or disrupted the local structure of this domain. An even less subtle mutation was found in an E. coli strain developed and screened for high butanol tolerance (L33). Surprisingly, sequence analysis revealed that this strain had acquired an rpoA variant devoid of almost its entire C-terminal domain (FIG. 8a). This severe protein truncation clearly reinforces the idea that a partial or complete loss of αCTD function may be needed to elicit all of the selected phenotypes.

Given this strong support for a nonspecific rpoA mechanism, we then wondered whether all three recovered rpoA plasmids actually had the same transcriptional and metabolic effects within a cell. If such were the case, these plasmids should prove to be completely interchangeable; that is, a plasmid that was selected for one cellular property should, in the appropriate strain background, also prove to be effective in eliciting a second, unrelated phenotype. We decided to test this interesting possibility by attempting to recover high L-tyrosine titers using plasmids derived from both the butanol-tolerant strain L33 and the hyaluronic acid producer rpoA-HA (denoted pL33 and pHA, respectively). Transformation of these two plasmids into a cured rpoA14 strain led to some intriguing results. As shown in FIG. 8b, both plasmids led to L-tyrosine titers that were either comparable or slightly higher than those seen for rpoA14. More impressively, however, pL33 and pHA were also able to significantly increase the rate of L-tyrosine production in these strains. Their performance was similar to that seen in rpoA22-sm, with almost all L-tyrosine produced after just 24 hr. These results clearly support the notion that functional shifts or deficiencies in αCTD are sufficient for redirecting substrate flow into the L-tyrosine pathway. However, because slight differences were still seen with regards to L-tyrosine productivity, it appears that specific sequence alterations do still play a subtle role in influencing cellular function.

Plasmid and Background Synergisms are Nonspecific

In the previous section, we explored the unexpected interchangeability of rpoA plasmids that had been selected for three distinct cellular phenotypes. Because this initial test was only limited to a cured rpoA14 strain, we decided to broaden our analysis in order to examine the effects of these plasmids in other strain backgrounds. The scope of this next study extended beyond just the rpoA library, as we chose to include both pHACM-rpoD3 and the rpoD3 background in these follow-up experiments. Although we are well aware that rpoA-encoded α and rpoD-encoded $\sigma^{70}$ possess discrete functions within a cell, we were interested in probing whether this plasmid phenomenon would hold not just between phenotypic groupings but across target/library boundaries as well.

Figure 9:
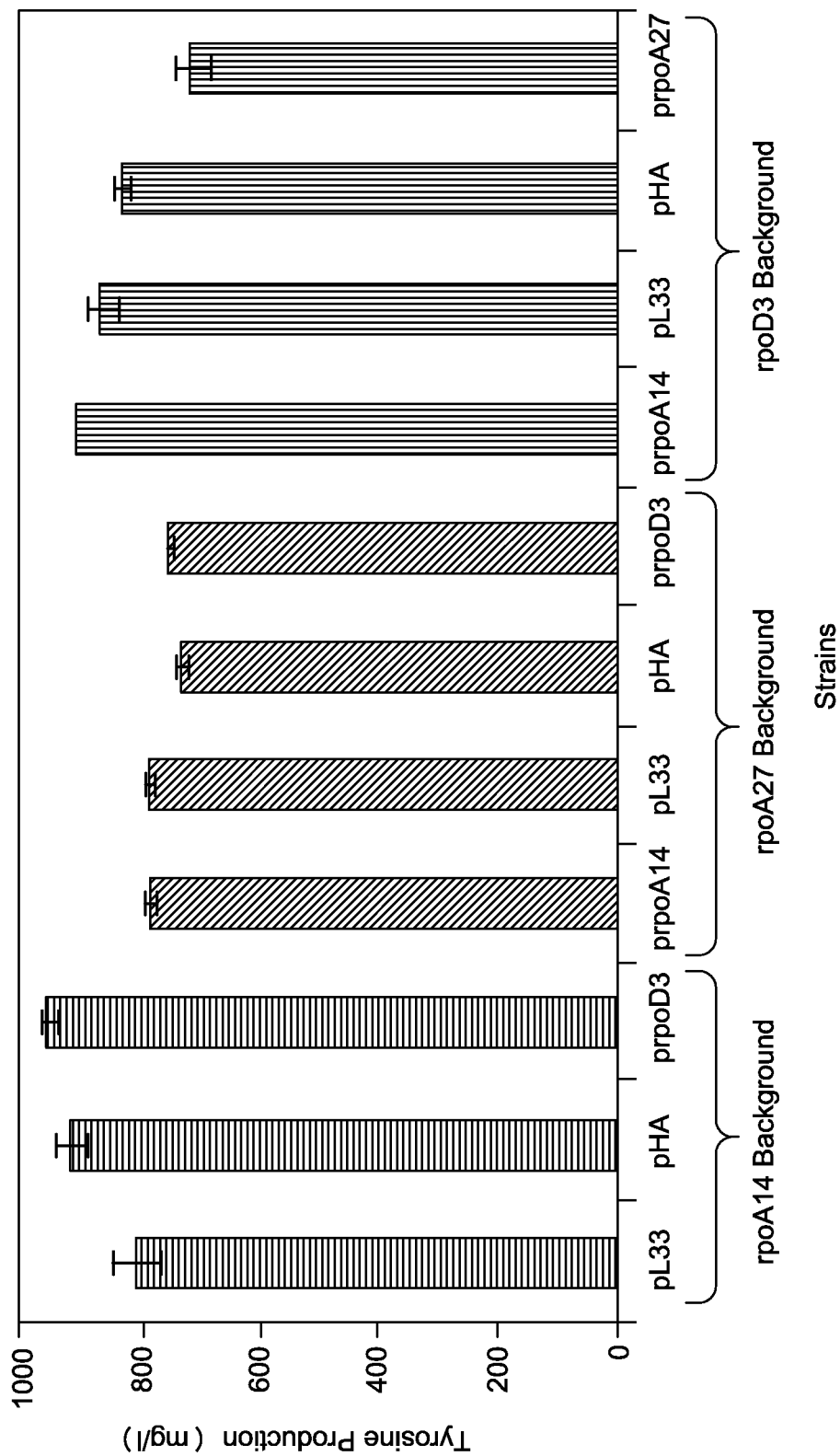
FIG. 9. Interchangeability of backgrounds and plasmids. L-tyrosine production of various background-plasmid combinations were measured after 48 hr. Strains with an rpoA14, rpoA27, or rpoD3 cured background, respectively, are indicated. Labels preceded by a "p" indicate the strain from which the mutant rpoA or rpoD plasmid was isolated. Results for prpoA27 (equivalent to pHACM-rpoA$^{WT}$) in an rpoA14 background were not included, as this has previously been shown to be detrimental to phenotype (FIG. 5).

We began this inquiry by constructing a comprehensive set of strains encompassing all possible combinations of mutant plasmid (pL33, pHA, pHACM-rpoA14, pHACM-rpoA27, pHACM-rpoD3) and cured backgrounds (rpoA14, rpoA27, rpoD3). Strains were then cultivated in MOPS minimal medium and characterized for L-tyrosine production. The results were once again quite startling. As shown in FIG. 9, all rpoA and rpoD plasmids were sufficient for recovering high titers of L-tyrosine regardless of the mutant background in which it was present. Although levels were generally lower in a cured rpoA27 strain, all plasmid-background combinations still yielded titers that either closely approached or even exceeded the values seen for our original isolates. Contrary to our expectations, this experiment also revealed that rpoA and rpoD plasmids possess the property of interchangeability, despite having been selected from completely separate transcriptional libraries.

While the mechanism underlying this phenomenon is presently unknown, one can envision two separate conditions that may contribute to these seemingly unlikely results. The first possibility, as suggested by our analysis of the rpoA αCTD, is that all tested plasmids may be working through a very generic mode of action. If this were in fact the case, it then comes as no surprise that a similar phenotype can be elicited in all three backgrounds. Despite the plausibility of this scenario, however, we are hesitant to fully endorse it, given that interchangeability between the mutated forms of two functionally distinct proteins (α subunit, $\sigma^{70}$) was also observed. In addition, such a theory does not explain why a wild-type rpoA plasmid (pHACM-rpoA27), which contains no deficiencies in its C-terminal domain, could also elicit the same results in an rpoD3 background (FIG. 9). The second possible explanation is a much simpler one which assumes that the same chromosomal aberration occurred in all three backgrounds. However, this scenario seems highly unlikely when one considers the number of possible base pairs substitutions that can occur during any given mutational event (4.6 million). The recovery of the exact same mutation in three distinct strains isolated from two separate libraries then becomes virtually impossible. Given the serious flaws in both conjectures, it is clear that a more in-depth characterization of these strains is needed to elucidate this complex interplay between mutant plasmid and background.

Success Through Transcriptional Engineering

In this example, we have demonstrated the clear potential of using a transcriptional engineering approach for optimizing cellular phenotype. The screening of two libraries constructed through the mutagenesis of rpoA and rpoD led to significant increases in L-tyrosine production in three strains, which exhibited final titers of 798-893 mg/l L-tyrosine. Remarkably, this more than doubles the previous levels observed in the parental P2, and, to our knowledge, is the highest titer reported for 50 ml *E. coli* cultivations in minimal media. These titers correspond to an overall yield of 0.16-0.18 g L-tyrosine/g glucose, a value that exceeds the best previously reported strain by 44% (Lütke-Eversloh and Stephanopoulos 2007).

It is important to note that the capabilities of these gTME-derived strains far surpass those of rationally engineered organisms. Through this demonstrated ability to reach previously inaccessible phenotypes, we see then that gTME is able to properly distinguish itself, even from other promising and more established combinatorial engineering methods. These advantages likely stem from its unique ability to reprogram the transcriptome, alter the entire cellular milieu, and as a result, generate an enormous amount of phenotypic diversity. As seen through these experiments, this ability to span such a wide range of phenotypic space greatly increased our chances of recovering desirable transcriptional mutants.

Limitations of gTME

Despite these unexpected successes, however, we do believe that this gTME technique is not without limitations. For example, when we attempted to recover improved mutants through a second round of transcriptional engineering, we found that although productivity was heightened, fewer gains were seen with respect to overall yields and titers. While the absence of a significantly enhanced mutant may have been influenced by our site-restricted saturation mutagenesis approach, we also cannot discount the possibility that we may have already reached the upper limit of this technique. The best performing mutant from this second round exhibited a titer of 962 mg/l L-tyrosine and a yield of 0.19 g L-tyrosine/g glucose, which represents only 35% of the maximum theoretical value (or 73% when accounting for biomass formation). Because there still seems to be additional room for improvement, it may then be worthwhile to explore the use of complementary, orthogonal methods for further improving L-tyrosine production in these strains. In addition, proper scale-up and process optimization may also be sufficient for enhancing strain performance as has been recently demonstrated in other studies (Lütke-Eversloh and Stephanopoulos 2007; Patnaik, Zolandz et al. 2008).

Complications with Inverse Metabolic Engineering

Unfortunately, transcriptional modification by gTME, while certainly a boon for recovering desirable mutants, becomes somewhat of a disadvantage when it comes time to apply an inverse metabolic engineering paradigm. Because so many modifications have transpired within the cell, it becomes almost impossible to pinpoint which specific changes are responsible for the desired phenotype. This complexity ultimately limits our ability to understand the underlying genotype to phenotype biochemistry, and therefore provides no additional insights for formulating directed strategies for engineering future cells.

Our inability to probe these causal mechanisms does not necessarily limit transferability of the desired phenotype into a novel strain. Indeed, when recipient and donor strains are sufficiently similar, this task can be easily accomplished simply by transforming the plasmid-encoded transcriptional unit into the new background. Unfortunately for us, however, the unusual existence of chromosomal mutations that appear to be causally linked to L-tyrosine production makes this a much more difficult endeavor. Indeed, this peculiar requirement forces us to conduct a full characterization of the isolated strains in order to identify a suitable method for imparting this desired cellular property. In the next example, we will discuss several approaches for investigating the cellular changes in these strains and, ambitiously, attempt to utilize this information to generate novel strains capable of L-tyrosine overproduction.

Example 3

Analysis of Transcriptional Engineering Mutants

As discussed above, transcriptional engineering of both $\sigma^{70}$ and the σ subunit of RNA polymerase led to the isolation of several strains possessing an enhanced capacity for L-tyrosine production. Unfortunately, however, we discovered early on that this desirable property could not be imparted simply through plasmid transfer but rather, required the contributions of an unidentified chromosomal mutation within the strain. In this example, we discuss our attempts to fully characterize both the genetics and the underlying biochemistry responsible for these mutants' phenotypes. In doing so, we hope to a) gain a better understanding of the factors that influence L-tyrosine production and b) use this information to formulate novel strategies for engineering these properties into future production strains.

Materials and Methods
Transcriptional Analysis

Strains P2, rpoA14, rpoA27, and rpoD3 were grown in 50 ml MOPS minimal medium (Teknova) (Neidhardt, Bloch et al. 1974) to an $OD_{600}$ of approximately 0.4. Triplicates samples of RNA (on three separate days) were then extracted using the QIAGEN RNeasy Mini Kit according to the manufacturer's protocol. Microarray services were provided by the David Koch Institute for Integrative Cancer Research Microarray Technologies Core Facility using the GeneChip E. coli Genome 2.0 Arrays (Affymetrix). Arrays were run in triplicate with biological replicates to allow for statistical confidence in differential gene expression. Microarray data was deposited in the Gene Expression Omnibus database under accession number GSE21652. Expression profile deviations between mutants and parental were identified by a Significance Analysis of Microarrays (SAM) analysis using SAM 3.0 (Tusher, Tibshirani et al. 2001).

Creation of pZE Overexpression Plasmids

E. coli K12 genomic DNA was prepared using the Wizard Genomic DNA Purification Kit (Promega) and used as a template for the synthesis of genes gadE, ydeO, evgA, and relA with Phusion DNA polymerase (New England Biolabs). All PCR fragments were digested with KpnI and BsaI or MluI and subsequently ligated to similarly digested pZE-gfp plasmids. To enable testing of both low- (II, AA, Y) and high- ($P_L$) level expression, two promoters from a synthetic library were used in the creation of each gene construct (Table 3.1) (Alper, Fischer et al. 2005). Following transformation into chemically competent E. coli DH5α (Invitrogen), plasmids were isolated and verified by both PCR and sequencing. All enzymes used in the cloning procedure were purchased from New England Biolabs. Primer names and sequences used for gene amplification are listed in Table 3.2.

TABLE 3.1

Relative strengths of four synthetic promoters

| Promoter | Average promoter strength metric (0 to 1)[a] |
|---|---|
| II | 0.04 |
| AA | 0.22 |
| Y | 0.31 |
| $P_L$ | 0.87 |

[a]data provided by C. Fischer

TABLE 3.2

Primers used in this study

| Primer Name | Primer Sequence (5' → 3') |
|---|---|
| CS555 evgA sense KpnI | CTC GGT ACC ATG AAC GCA ATA ATT ATT GAT GAC CAT CC (SEQ ID NO: 11) |
| CS556 evgA anti MluI | CGA CGC GT T TAG CCG ATT TTG TTA CGT TGT GCG (SEQ ID NO: 12) |
| CS557 ydeO sense KpnI | CTC GGT ACC ATG TCG CTC GTT TGT TCT GTT ATA TTT ATT C (SEQ ID NO: 13) |
| CS558 ydeO anti BsaI | GGT CTC TCT TTT CAA ATA GCT AAA GCA TTC ATC GTG TTG C (SEQ ID NO: 14) |
| CS559 gadE sense KpnI | CTC GGT ACC ATG ATT TTT CTC ATG ACG AAA GAT TCT TTT C (SEQ ID NO: 15) |
| CS560 gadE anti MluI | CGA CGC GTC TAA AAA TAA GAT GTG ATA CCC AGG GTG ACG (SEQ ID NO: 16) |
| CS582 relA sense KpnI | CTC GGT ACC ATG GTT GCG GTA AGA AGT GCA CAT ATC A (SEQ ID NO: 17) |
| CS699 purF sense | GCA GCA ATG GCA GCG AAA ATA TTG (SEQ ID NO: 18) |

TABLE 3.2-continued

Primers used in this study

| Primer Name | Primer Sequence (5' → 3') |
|---|---|
| CS700 purF anti | CAG TCT GGT TTA CGG GCT TTG AAG AC (SEQ ID NO: 19) |
| CS701 hisH sense | TCT CAG CAC CGA AAT GAT CGA GCA (SEQ ID NO: 20) |
| CS702 hisH anti | CCG GAA TAA TCA TCA CAT CTC CAG GA (SEQ ID NO: 21) |
| CS707 pKD13 kan-purF sense | TAA CGC ACA TGA CCA ATG CCC ATA TTG CCC TGC AAA CGC TGC ATA TGG CGA GCG TGT AGG CTG GAG CTG CTT C (SEQ ID NO: 22) |
| CS708 pKD13 kan-purF anti | CGG TAC TGT TTA TCG CTA CCC TGA TCG TTG GTG CTA TCG TGA ACT TCG TGA TCC GTC GAC CTG CAG TTC GA (SEQ ID NO: 23) |
| CS709 pKD13 kan-hisH sense | CGT GAC CCG GAC GTC GTG TTG CTG GCC GAT AAA CTG TTT TTA CCC GGC GTT GGC ACT GAT CCG TCG ACC TGC AGT TCG A (SEQ ID NO: 24) |
| CS710 pKD13 kan-hisH anti | CGG CAT TGC GTA GCT GTG AAC AAA GTA AAA GTA CGC GCC GTC TTC AAT CCC CTG TGT AGG CTG GAG CTG CTT C (SEQ ID NO: 25) |

Whole Genome Sequencing and SNP Detection

Whole genome sequencing for strains P2, rpoA14, rpoA27, and rpoD3 was performed using the Illumina/Solexa Genome Analyzer System. Briefly, genomic DNA from all four strains was extracted using the Wizard Genomic DNA Purification Kit (Promega). Samples were then fragmented and prepared for paired-end sequencing using the Paired-End DNA Sample Prep Kit (Illumina). Samples were analyzed and processed at the MIT Biopolymers Laboratory, with duplicate lanes used for each strain. Sequence alignment and analysis, including the detection of insertions, deletions, and SNPs, was performed by the David Koch Institute Bioinformatics Facility. All sequence deviations from P2 were additionally validated by Sanger sequencing.

Raw sequence data for the whole genome scans can be accessed in the form of raw data files are available at the National Center for Biotechnology Information Sequence Read Archive under accession number SRA012672.14.

Reengineering of SNPs into the Bacterial Chromosome

In order to reintroduce verified SNPs back into a P2 background, we utilized a two-step lambda-red recombination based method (Datsenko and Wanner 2000) to delete the relevant locus and subsequently replace it with a SNP-substituted variant. Two knockout cassettes for both the purF and hisH genes were generated by amplification of pKD13's $kan^{FRT}$ region using Taq DNA polymerase. Primers CS707 pKD13 kan-purF sense and CS708 pKD13 kan-purF anti were used for the generation of purF::kan integration cassettes, and CS709 pKD13 kan-hisH sense and CS710 pKD13 kan-hisH anti were used to create the hisH::kan fragment (Table 3.2). All four primers incorporated 50-58 bp of homology with the ends of their respective targets to facilitate integration into the proper locus. Following transformation of into P2 pJM12, colonies were verified by colony PCR and sequencing. Cassettes for the second round of integration were generated through the amplification of SNP-containing purr and hisH using primers CS699 purF sense, CS700 puff anti, CS701 hisH sense, and CS702 hisH anti (Table 3.2), as well as genomic DNA preparations from mutant rpoA14, rpoA27, and rpoD3 as templates. SNP variants were then transformed into either P2 purF::$kan^{FRT}$ pJM112 or P2 hisH:: $kan^{FRT}$ pJM112 and grown overnight in 5 ml M9 minimal medium (Sambrook, Fritsch et al. 1989) with 5 g/l glucose. Correct transformants were selected by this alternate method due to the absence of an antibiotic marker for the second integration event. However, because purF and hisH deletion strains exhibit much slower growth rates in minimal medium than their SNP-containing counterparts, this selection process was easily accomplished after just a single round of overnight growth in minimal media. Individual colonies were then tested for the loss of kanamycin resistance (indicating replacement of $kan^{FRT}$ with mutated purF or hisH and later validated by colony PCR and sequencing.

Analytical Methods

For the quantification of L-tyrosine, cell-free culture supernatants were filtered through 0.2 μm PTFE membrane syringe filters (VWR International) and used for HPLC analysis with a Waters 2690 Separations module connected with a Waters 996 Photodiode Array detector (Waters) set to a wavelength of 278 nm. The samples were separated on a Waters Resolve C18 column with 0.1% (vol/vol) trifluoroacetic acid (TFA) in water (solvent A) and 0.1% (vol/vol) TFA in acetonitrile (solvent B) as the mobile phase. The following gradient was used at a flow rate of 1 ml/min: 0 min, 95% solvent A+5% solvent B; 8 min, 20% solvent A+80% solvent B; 10 min, 80% solvent A+20% solvent B; 11 min, 95% solvent A+5% solvent B. Cell densities of cultures for growth rate calculations were determined by measuring their absorbance at 600 nm with an Ultrospec 2100 pro UV/Visible spectrophotometer (Amersham Biosciences).

Cultivation Conditions

L-tyrosine production experiments were performed at 37° C. with 225 rpm orbital shaking in 50 ml MOPS minimal medium (Teknova) (Neidhardt, Bloch et al. 1974) cultures supplemented with 5 g/l glucose and an additional 4 g/l NH$_4$Cl. All liquid cultivations were conducted in at least triplicates. When appropriate, antibiotics were added in the following concentrations: 34 µg/ml chloramphenicol for maintenance of pHACM-derived plasmids and 20 µg/ml kanamycin for maintenance of pZE-derived plasmids. L-phenylalanine auxotrophic (ΔpheA) cultures were additionally provided with L-phenylalanine (Sigma) at a concentration of 0.35 mM.

Fed-Batch Fermentations of rpoA 14$^R$ rpoA14$^R$ was cultured in 5 ml LB medium until the mid-exponential phase, then transferred into 2-50 ml MOPS minimal or R medium cultures at a starting $OD_{600}$ of 0.1. These were cultivated at 37° C. with 225 rpm orbital shaking until the mid-exponential phase and were subsequently used as the inoculum for a 1.5-1 culture (5% by volume).

Fed-batch fermentations for rpoA14$^R$ were performed in 2-1 glass vessels using the BioFlo110 modular fermentor system (New Brunswick Scientific). MOPS minimal medium and R medium (Riesenberg, Schulz et al. 1991) fermentations were performed at 37° C. with a pH automatically adjusted to 7.0 using 30% solution of ammonium hydroxide. The media was additionally supplemented with 0.5 g/l L-phenylalanine and 68 µg/ml chloramphenicol. Dissolved oxygen (pO2) was maintained at >25% by agitation speed (100-1,000 rpm) and gas mix control (air/oxygen). Foam formation was controlled by the addition of Tego Antifoam KS911 (Evonik Goldschmidt). Operations were controlled and recorded with the BioCommand Lite Data Logging software (New Brunswick Scientific).

Results

Full Transcriptional Analysis of Three gTME Mutants

Mutations introduced during gTME often have global effects within the cell and, as a result, frequently lead to changes in the transcript levels of hundreds if not thousands of genes. The main challenge in strain characterization for inverse metabolic engineering then becomes the identification of the undoubtedly small subset of alterations (out of these hundreds) that possess a causal link to the phenotype. Thus, to approach this problem, it becomes necessary to conduct a full analysis of the observed transcriptional changes between desirable mutants and their corresponding parental strains. By observing differential patterns in gene expression, it may then be possible to identify specific pathways or mechanisms by which a phenotype is influenced and manipulated.

For the specific case of L-tyrosine production, we were fortunate in that three separate mutants were identified to have comparably high capacities for L-tyrosine production. Although such strains may have acquired these traits by disparate mechanisms, it is our hope that sufficient similarities in gene expression may point us to relevant pathways responsible for influencing strain performance. In this section, we assume a full transcriptional analysis of four strains—rpoA14, rpoA27, rpoD3, and P2—using the GeneChip *E. coli* Genome 2.0 Arrays (Affymetrix). Expression profile deviations between mutants and parental were identified by a Significance Analysis of Microarrays (SAM) analysis using SAM 3.0 (Tusher, Tibshirani et al. 2001). Here, we discuss our analysis of this comparative data and describe the process by which we select and subsequently test additional genetic targets for metabolic engineering.

Analysis of Upregulated Genes

Because of the sheer number of differentially expressed loci, we decided to first focus our analysis on the upregulated pathways found in these strains. Quite surprisingly, our transcriptional comparisons returned a very small and manageable number of upregulated genes, with only 17 loci identified for rpoD3, 6 for rpoA27, and none for rpoA14. Curiously, a large percentage of these presumed hits were found to possess functions related to acid stress resistance (Table 3.3).

TABLE 3.3

List of upregulated genes related to acid resistance

| Gene Name | Gene ID | Function | rpoD3 Log Fold Change | rpoD3 q-value[a] (%) | rpoA27 Log Fold Change | rpoA27 q-value[a] (%) |
|---|---|---|---|---|---|---|
| b3517 | gadA | glutamate decarboxylase | 2.236 | 0 | 1.974 | 11.05 |
| b1493 | gadB | glutamate decarboxylase | 2.699 | 0 | 2.515 | 0 |
| b1492 | gadC | glutamate:γ-aminobutyrate antiporter | 2.027 | 0 | — | — |
| b3512 | gadE | transcriptional activator | 2.137 | 0 | 2.160 | 0 |
| b3510 | hdeA | acid stress chaperone | 1.950 | 0 | — | — |
| b3509 | hdeB | acid stress chaperone | 2.115 | 0 | — | — |
| b3511 | hdeD | acid resistance membrane protein | 1.707 | 0 | — | — |
| b3506 | slp | starvation lipoprotein | 1.609 | 10.17 | 1.897 | 5.67 |

[a]q values represent the lowest False Discovery Rate at which that gene is called significant. It is like the well-known p-value, but adapted to multiple-testing situations.

*E. coli* possesses three acid resistance pathways, two of which rely on decarboxylase/antiporter systems that utilize external amino acids to protect cells during extreme acid challenges. The genes gadA, gadB, and gadC encode for the most efficient of the three, the glutamate-dependent acid resistance system (AR2), and were recovered as upregulated targets in both rpoA27 and rpoD3 (Table 3.3). During conditions of acid stress, the GadA and GadB glutamate decarboxylase isozymes actively convert intracellular glutamate and a proton to γ-aminobutyrate. The GadC antiporter then orchestrates the export of this product in exchange for extracellular glutamate. The consumption of internal protons mediated by this system helps the cell maintain a suitable cytosolic pH for survival (Ma, Gong et al. 2003).

The bacterial periplasm is known to be quite vulnerable to acid stress due to its permeability to small molecules less than 600 Da in size. Thus, to prevent the acid-induced aggregation of periplasmic proteins, *E. coli* is known to express the hdeA- and hdeB-encoded acid stress chaperones (Gajiwala and Burley 2000; Kern, Malki et al. 2007). These two proteins, along with the hdeD-encoded acid stress membrane protein, were among the list of upregulated components in rpoD3. Along with hindering the formation of insoluble periplasmic bodies at low pHs, more recent studies have also demonstrated the roles of HdeA and HdeB in assisting with the resolubilization and renaturation of existing protein aggregates (Malki, Le et al. 2008). Although HdeD is known to be part of the acid resistance transcriptional network, few studies have investigated its specific role in the cell's response to acid-induced stress (Masuda and Church 2003).

Figure 10:
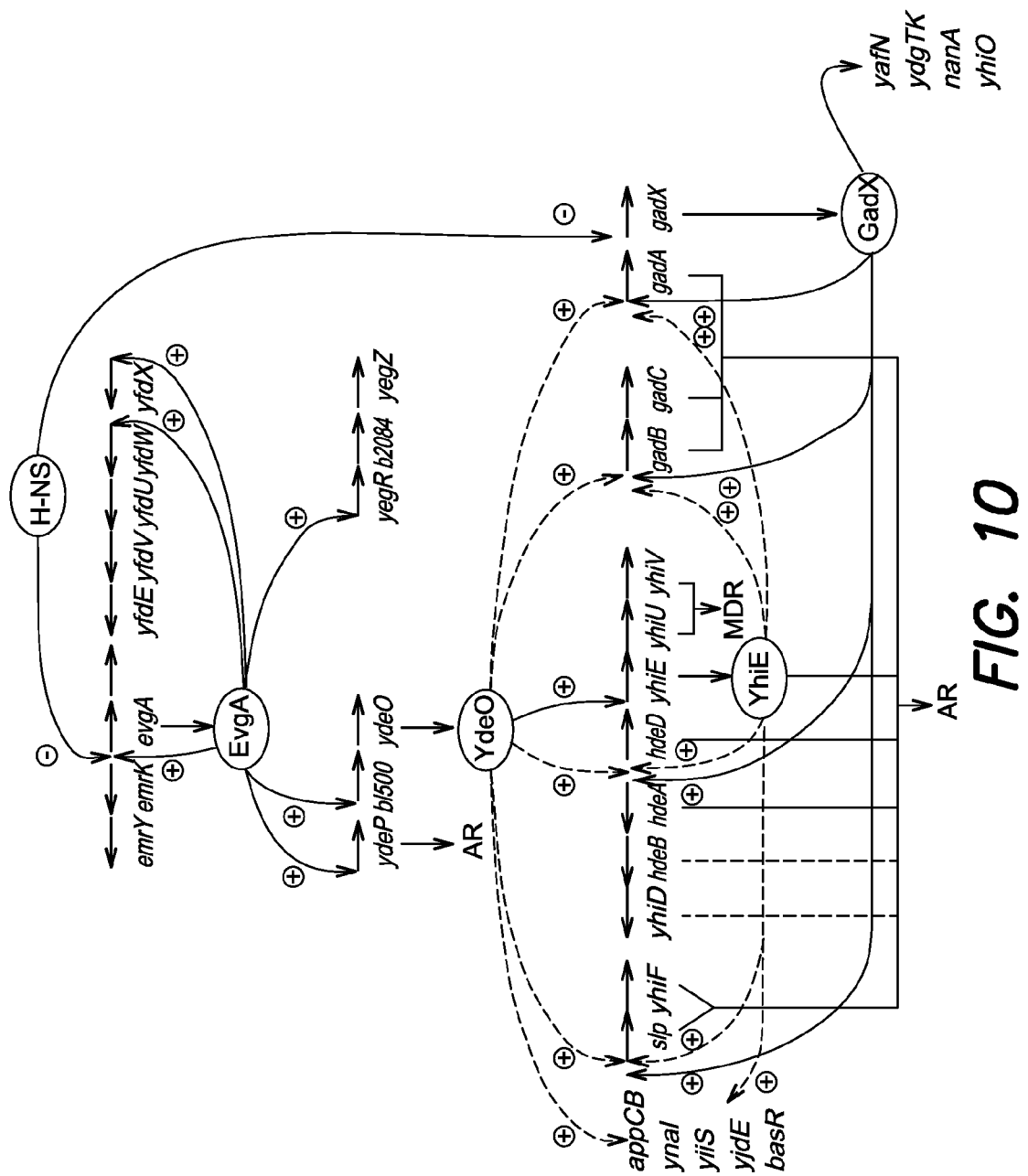
FIG. 10. Regulatory network of acid resistance genes. Figure taken from (Masuda and Church 2003). Encircled protein names represent transcriptional regulators with "+" representing activation and "−" representing repression. Note that YhiE/yhiE and GadE/gadE are equivalent proteins/genes.

Because several genes involved with acid stress resistance were recovered from our analysis, we decided to investigate the specific transcriptional controls that govern these pathways. Fortunately, an in-depth investigation of the acid stress transcriptional network has already been performed by other labs, allowing us to simply compare the recovered loci with existing transcriptional maps (FIG. 10) (Masuda and Church 2003). Interestingly, all genes listed in Table 3.3 were found to lie within the same regulon, with the proteins YdeO and GadE (YhiE) exerting direct transcriptional control over the identified operons. The expression of YdeO is, in turn, influenced by the regulator EvgA which exists one level above in the network. Given this configuration, we hypothesized that both YdeO and GadE could be used as genetic dials for modulating the acid stress response of E. coli. Moreover, if acid stress resistance is indeed related to L-tyrosine production as is hinted by our transcriptional data, then altering the expression of these two proteins may have interesting implications for engineering this particular phenotype.

Figure 11:
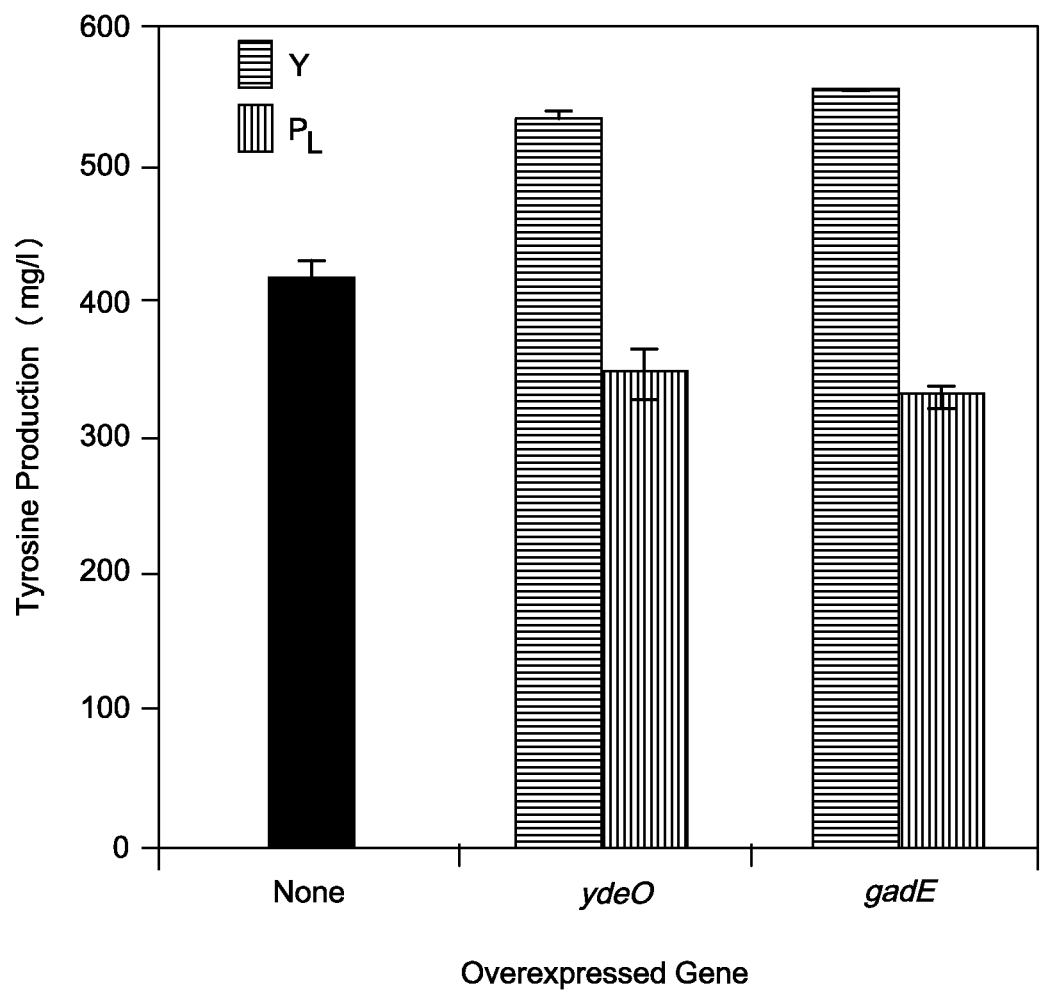
FIG. 11. Overexpression of ydeO and gadE in parental strain P2. Two promoter strengths for each gene were tested: Y (low, left bar in each grouping of two bars) and P$_L$ (high, right bar in each grouping of two bars). Numerical comparison of relative strengths can be found in Table 3.1.

To explore this possibility, we began by constructing overexpression plasmids for both ydeO and gadE using two versions of the pZE vector with a low- (Y) or high-strength ($P_L$) constitutive promoter. These plasmids were then transformed into the background of parental strain P2 to determine if they could be sufficient for imparting a L-tyrosine overproduction phenotype. Contrary to our expectations, plasmid-encoded ydeO and gadE yielded only moderate increases in L-tyrosine production over the parental (up 26-32% to 535-552 mg/l L-tyrosine, respectively) (FIG. 11). It was also interesting to note that such enhancements were seen only with low levels of ydeO and gadE overexpression. As seen in FIG. 11, the use of the stronger $P_L$ promoter actually resulted in a 17-22% drop in overall titer. Because slight gains were made through low ydeO and gadE expression, it is possible that the acid resistance pathway may still contribute to a L-tyrosine production phenotype; however, based on this data, it does not appear to be the sole or even the most important determinant.

Analysis of Downregulated Pathways

In stark contrast to the small number of upregulated genes found in the mutants, several (on the order of hundreds) of downregulated genes were recovered by our analysis. Although this large discrepancy seems unusual at first glance, it may also simply reflect the nature of a transcriptional engineering approach. Because this technique relies on the introduction of mutations into essential components of the transcriptional machinery, it is likely that overall activity along with specificity is altered. Even small decreases in the rate of RNA polymerase function could influence the number of transcripts generated, which would then be reflected as downregulated expression of that particular genetic component.

Regardless of the exact mechanism by which this phenomenon occurs, it is clear that the sheer number of genes recovered by our analysis makes it quite difficult to parse out specific patterns of underexpression. Thus, to convert this into a more manageable problem, we decided to make use of Ecocyc's Pathway Tools Omics Viewer (ecocyc.org/). Taking transcriptional data as its input, this tool is able to overlay over- and under-expression ratios onto a preassembled metabolic network. Simple color mapping then allows one to immediately distinguish pathways that have a significant number of genes exhibiting differential expression. The results of this analysis are summarized in Table 3.4.

TABLE 3.4

List of downregulated pathways in rpoD3, rpoA14, and rpoA27

| Pathway | rpoD3 | rpoA14 | rpoA27 |
|---|---|---|---|
| Arginine synthesis | ✓ | ✓ | ✓ |
| Isoleucine synthesis | ✓ | ✓ | ✓ |
| Leucine/valine synthesis | ✓ | ✓ | |
| Histidine synthesis | ✓ | | ✓ |
| Tryptophan synthesis | ✓ | | ✓ |
| Lysine synthesis | ✓ | ✓ | |
| Glutamate synthesis | ✓ | ✓ | ✓ |
| De novo purine/pyrimidine biosynthesis | ✓ | | |
| DNA replication | ✓ | | ✓ |
| Ribosomal proteins and RNA | ✓ | ✓ | ✓ |
| Fatty acid elongation | | ✓ | |

Figure 12:
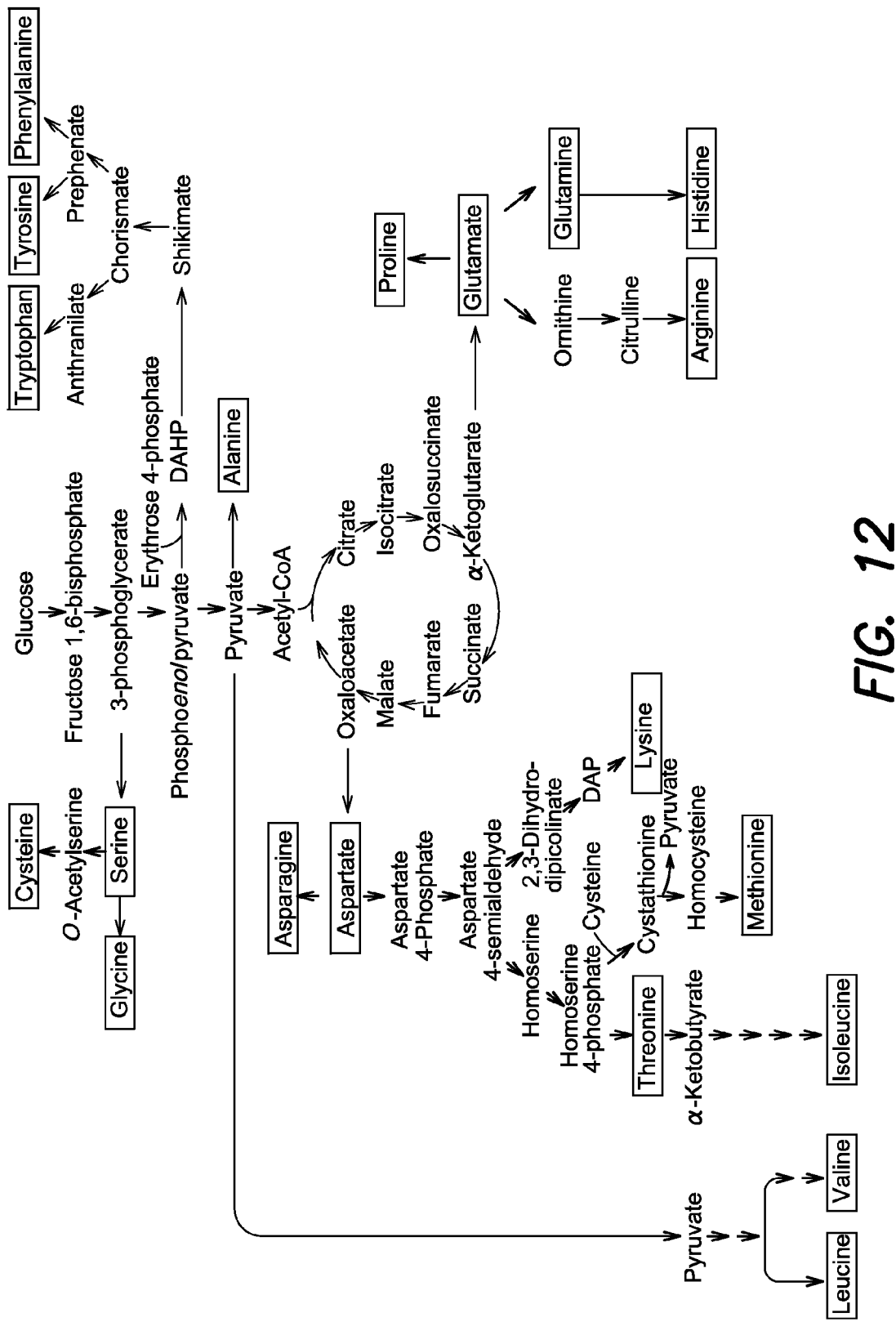
FIG. 12. Pathways and precursors for amino acid biosynthesis.

At first glance, the most conspicuous result from this analysis seems to be the large number of amino acid pathways that were seen to be downregulated in these mutant strains. While we cannot offer any theories as to why or how these specific pathways were targeted, it is interesting to note that some of these findings do fit when evaluated from a biochemical standpoint. Indeed, because many of these amino acids share common precursors with L-tyrosine (and the other aromatic amino acids), it is not unreasonable to assume that reduced synthesis of these competing compounds could lead to higher overall levels of L-tyrosine within the cell (FIG. 12). As an example, leucine and valine, which share both a common pathway and the requirement for the precursor pyruvate, saw reduced expression of its biosynthetic genes in all three gTME-derived strains. Lower levels of leucine and valine production and hence pyruvate consumption could ultimately lead to a larger pool of PEP, one of the limiting precursors for L-tyrosine production. We also see that arginine and histidine biosynthesis is affected, a potentially significant result if the supply of the precursor glutamate became limiting for the final transamination step of L-tyrosine biosynthesis. Finally, it is not surprising that downregulation of tryptophan synthesis could be beneficial, given that it shares much of the aromatic amino acid biosynthetic pathway with L-tyrosine and pulls significantly from the supply of chorismate. Despite these suppositions, however, it remains unclear as to how decreased synthesis of arginine, isoleucine, lysine, and glutamate may impact L-tyrosine production.

Because the downregulation of several amino acid pathways could not offer any additional insights into the underlying strain biochemistry, we decided to focus our attentions on three other identified pathways. In particular, observed decreases in the production of ribosomal subunit protein transcripts were quite intriguing, especially since these changes were found to be common among all three mutants. Indeed, when examined together with reductions in both fatty acid and purine/pyrimidine biosynthesis, a potential role for guanosine tetraphosphate/pentaphosphate (collectively known as (p)ppGpp) and the stringent response began to emerge.

Figure 13:
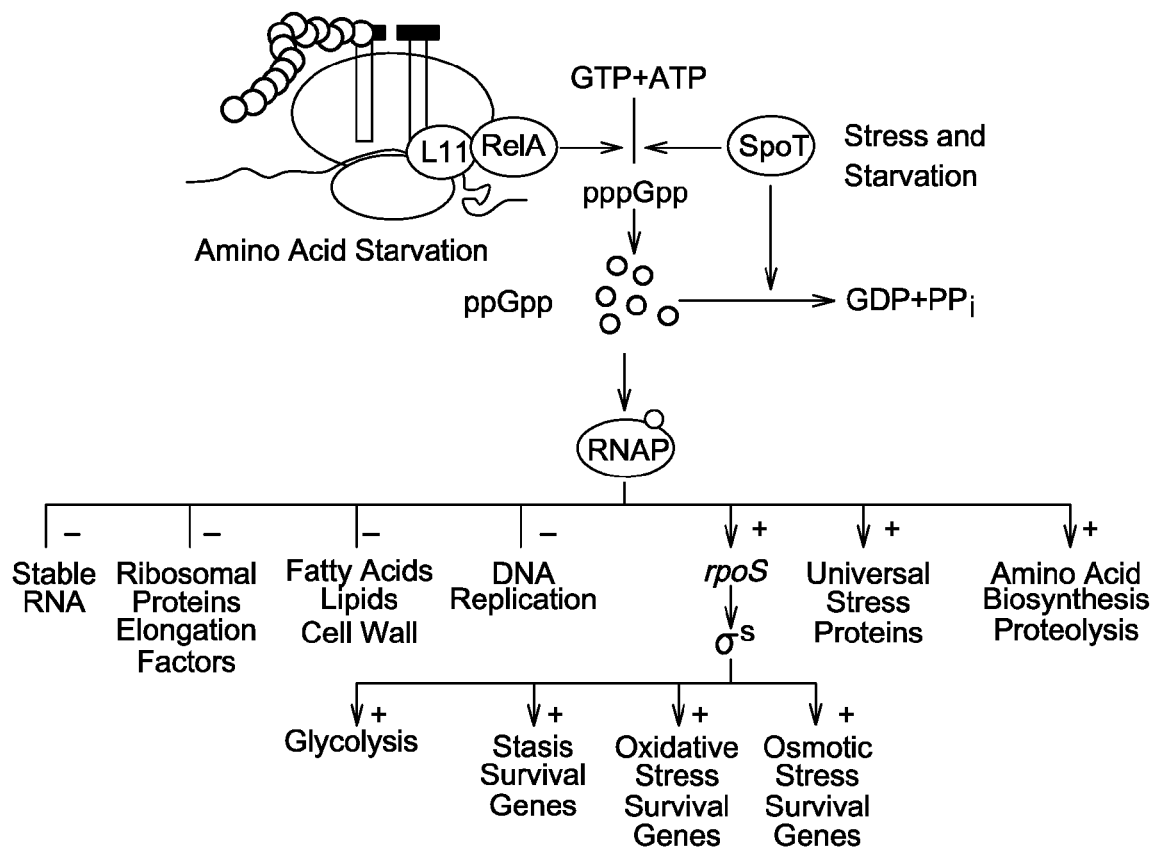
FIG. 13. The stringent response on *E. coli*. This figure, taken from Magnusson et al, highlights the effects usually seen during a stringent response mediated by (p)ppGpp overexpression. Levels of (p)ppGpp are mediated by two enzymes: relA-encoded ppGpp synthase and SpoT, which possesses both synthase and hydrolase activity (Magnusson, Farewell et al. 2005).

(p)ppGpp is a small nucleotide regulator that is rapidly synthesized during conditions of nutritional stress. Two separate enzymes have been shown to be responsible for (p)ppGpp formation within E. coli, each responding to different environmental stressors (FIG. 13). The first ppGpp synthase, encoded by relA, is known to associate with ribosomes and is able to upregulate (p)ppGpp expression during amino acid starvation. Functional characterizations have shown that this reaction is mediated by the binding of uncharged tRNAs to the ribosomal 'A' site, which leads to stalled protein synthesis and subsequently enables this process. Although much less is known about the mechanism for the second spoT-encoded ppGpp synthase, it has been shown to be active during other conditions of stress, including the deprivation of phosphorus, iron, carbon source or fatty acids. Because SpoT also possesses hydrolase activity in addition to its synthase domain, it has the ability to quickly adjust and finely tune the levels of (p)ppGpp in response to changes in the cellular environment (Magnusson, Farewell et al. 2005; Potrykus and Cashel 2008; Srivatsan and Wang 2008).

Although no real scientific consensus has been reached regarding the specific mechanisms for (p)ppGpp action, its upregulation has been proven to have several immediate and widespread effects on cellular function (FIG. 13). On the whole, cellular resources are often redistributed from functions related to proliferation and growth to those needed for cell maintenance and survival. In particular, the downregulation of both ribosomal proteins and stable RNA (tRNA and rRNA) has long been considered the hallmark feature of the stringent response and was, surprisingly, observed in all three mutant strains (Table 3.4). Individual decreases in other proliferation-related activities, including DNA replication and fatty acid synthesis are also in accordance with a (p)ppGpp-related cellular response. While our focus in this section has been on downregulated transcriptional components in these strains, it is noteworthy to mention that several upregulated targets also corroborate our hypothesis. Indeed, stress survival genes, such as those of the acid resistance pathways, are among the first genetic targets influenced by increases in intracellular (p)pGpp levels (Magnusson, Farewell et al. 2005).

The only major discrepancy that can be found among our data set is the widespread downregulation of several amino acid biosynthetic pathways, which seems to be in direct contradiction with past studies evaluating (p)ppGpp-mediated cellular responses. However, it is important to note that these reports stemmed from in vitro experiments that focused on the use of narrow sets of amino acid promoters and/or operons (histidine, arginine, lysine, phenylalanine, threonine) for generating their data (Stephens, Artz et al. 1975; Paul, Berkmen et al. 2005); thus the notion that (p)ppGpp should upregulate the overproduction of all amino acids may be untrue. Indeed, more recent studies have called this general statement into question, with several in vivo transcriptional analyses demonstrating that these biosynthetic pathways are rarely upregulated en masse (Chang, Smalley et al. 2002; Durfee, Hansen et al. 2008; Traxler, Summers et al. 2008). Of particular interest, Durfee et al. observed that while a serine hydroxamate-induced stringent response in E. coli led to activation of seven attenuator-regulated leader sequences, transcript levels of the corresponding structural genes were actually found to be lower in these strains (Durfee, Hansen et al. 2008). Similar results were found with a glucose-lactose diauxie model in which most amino acid biosynthetic pathways (with the exception for histidine and arginine) were downregulated (Chang, Smalley et al. 2002).

All in all, our transcriptional analysis of P2, rpoD3, rpoA14, and rpoA27 certainly points to a potential role for (p)ppGpp in mediating the cellular responses observed in our strains. If this is in fact the case, we then wondered whether direct tuning of (p)ppGpp levels could be used to modulate each strain's individual capacities for L-tyrosine overproduction. To probe this possibility, we decided to overexpress the relA-encoded ppGpp synthase in the background of parental P2 to assess whether increasing (p)ppGpp concentrations could have a positive effect on L-tyrosine synthesis. Of note, this strategy was recently tested for the engineering of both glutamate and lysine production in E. coli and successfully led to 21% and 10% increases in yields, respectively (Imaizumi, Kojima et al. 2006).

Figure 14:
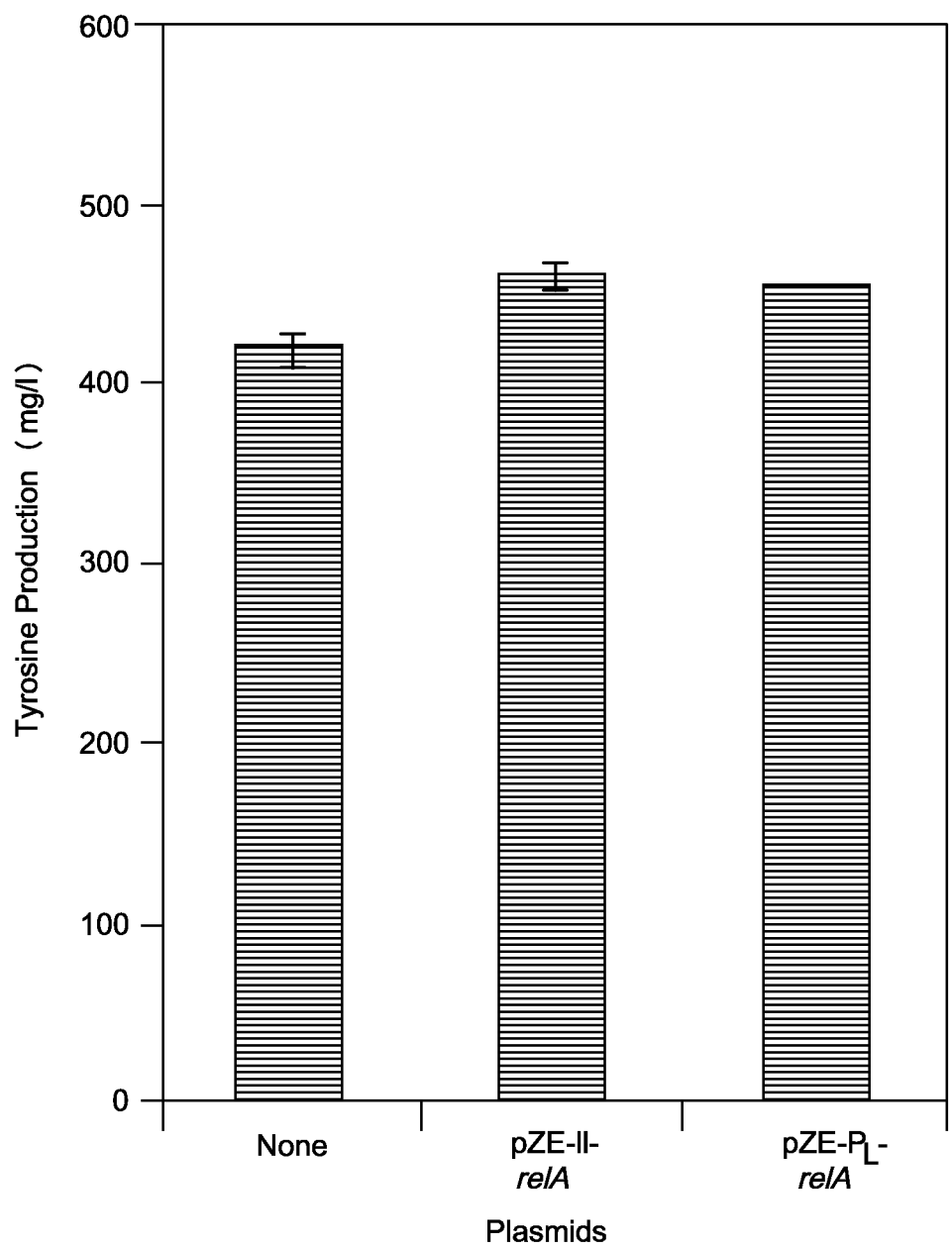
FIG. 14. Overexpression of relA in parental strain P2. Two promoter strengths for relA overexpression were tested: II (low) and PL (high). A numerical comparison of relative promoter strengths can be found in Table 3.1.

Unfortunately, the overexpression of relA in the background of parental P2 led to less than impressive increases in L-tyrosine production, particularly when compared to the titers observed in the original mutant isolates. As seen in FIG. 14, gains were limited to only 10% above the control, regardless of whether a weak (II) or strong ($P_L$) promoter was used. These results therefore introduce serious doubts as to whether a causal role for (p)ppGpp actually exists within these strains.

Overexpression of Transcriptional Regulators in Mutant Backgrounds

In our previous experiments, we focused on overexpressing select regulators and enzymes in the parental P2 to ascertain whether such modifications could recover the high L-tyrosine titers observed in our gTME-derived strains. Unfortunately, the answer was a resounding no, with only limited gains made (10-32%) in L-tyrosine production. Indeed, even the highest final titer (achieved with low-level gadE overexpression) represented a mere 62% of what had been previously shown to be achievable in the isolated mutant rpoD3. Although disappointed with these initial results, we then began to wonder whether the unidentified background mutations within rpoD3, rpoA14, and rpoA27 might be required for L-tyrosine synthesis. As shown above, these chromosomal variants were important for the phenotype, as only minimal increases in L-tyrosine titer were observed if mutated plasmids were provided alone (FIG. 5). It therefore seems feasible that, as with rpoA and rpoD, the benefits of ydeO, gadE, and relA overexpression may only become manifest when supplied in combination with these background mutations.

To investigate this possibility, we decided to transform the ydeO, gadE, and relA overexpression plasmids into the backgrounds of each of the cured mutant strains, rpoD3, rpoA14, rpoA27. In addition, the transcriptional regulator evgA was also provided on a pZE backbone and tested; as it exists one level above ydeO in the acid resistance network (FIG. 10), its expression may also have the capacity to influence strain performance.

Figure 15:
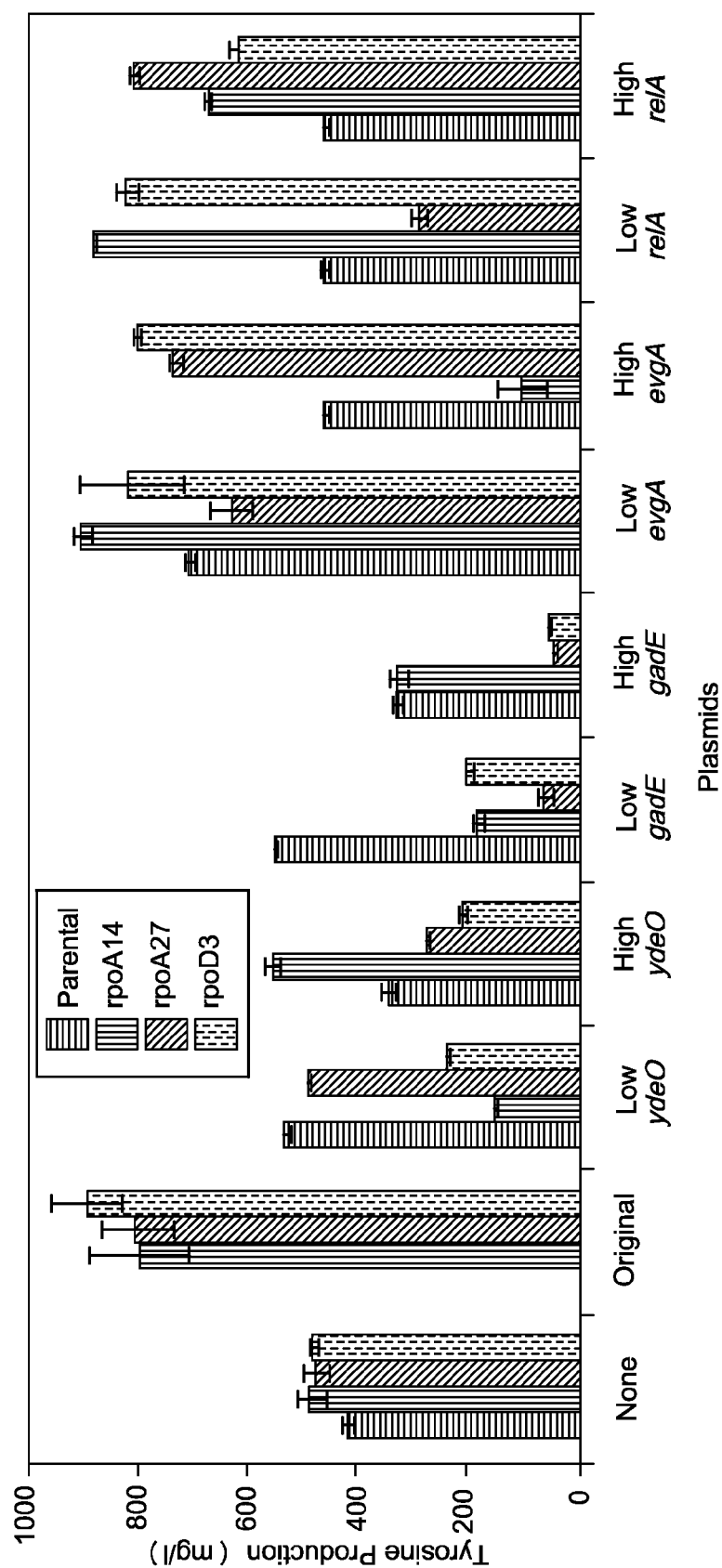
FIG. 15. Overexpression of ydeO, gadE, evgA, and relA in mutant backgrounds. The genes ydeO, gadE, evgA, and relA were individually overexpressed in four different backgrounds—the parental P2 (leftmost bar in each grouping; none in "original" group) and the cured backgrounds of rpoA14 (second from left bar in each grouping), rpoA27 (second from right bar in each grouping), and rpoD3 (rightmost bar in each grouping). Two promoter strengths were tested for each gene in order to ascertain the effects of both low and high level expression on cellular phenotype. All "high" strength promoters were P$_L$. "Low" strength promoters for ydeO, gadE, evgA, and relA were Y, Y, AA, and II, respectively (Table 3.1). L-tyrosine titers were measured after 48 hr cultivation in 50 ml MOPS minimal medium.

The results, as seen in FIG. 15, were wholly unexpected. Although severe decreases in L-tyrosine production were fairly consistent for ydeO and gadE overexpression strains, the transfer of evgA and relA plasmids led to remarkable increases in L-tyrosine production. In fact, the titers seen in the original isolates were not only matched but sometimes even exceeded, as seen prominently for the rpoA14 background. Of note, testing of two different strength promoters shows that the particular level of overexpression does contain an optimum that is both gene- and background-specific. It is quite possible then that fine-tuning the expression of these genes (perhaps through the use of additional synthetic promoters) may lead to even greater titers and yields than those observed here.

It is interesting to note that while evgA was quite successful in eliciting high L-tyrosine titers, overexpression of either ydeO or gadE alone did not have the same cellular effects. One possible explanation for this discrepancy may be some slight inaccuracies in the regulatory scheme mapped out for this complex network. Specifically, recent studies have questioned the proposed linearity of this system (FIG. 10) and have instead postulated a branched regulatory circuit for EvgA-YdeO-GadE control. In this alternate scheme, EvgA plays a direct role in upregulating gadE transcription during exponential growth in glucose-supplemented minimal medium (Ma, Masuda et al. 2004); thus, it is possible that evgA overexpression may actually be required to achieve full activation of these pathways. Another likely conjecture stems from our knowledge that EvgA is capable of mediating other responses besides those related to acid resistance, independent of both YdeO and GadE. If these other activated systems play even a limited role in L-tyrosine production, their specific effects on phenotype would only be elicited by the overexpression of evgA (Nishino and Yamaguchi 2001; Nishino, Inazumi et al. 2003).

Regardless of the precise explanation, the results discussed above clearly have widespread implications on the underlying biochemistry of these strains. Our analysis shows that the mutant rpoA/rpoD plasmids can be replaced by overexpression of either evgA or relA without the loss of phenotype. We therefore maintain that despite the widespread changes induced by these mutant transcriptional components, their L-tyrosine-specific effects can be isolated to the upregulation of these specific pathways. Because chromosomal mutations are still required for this phenotype, the exact mechanisms still remain somewhat of a mystery; however, these results clearly point to the important roles of both acid resistance and/or the stringent response in eliciting L-tyrosine overproduction.

A Whole Genome Sequencing Approach for Identifying Chromosomal Variations

Although we were able to deduce the specific functions of rpoA/rpoD overexpression in our mutant strains, the identities of the essential background mutations still represent a missing piece of the puzzle. Unfortunately, transfer of this phenotype into a novel strain continues to be difficult without this information and, as a result, our engineering work remains restricted to only these specific backgrounds. To overcome such limitations, it is clear that our next efforts must focus on uncovering the precise chromosomal alterations responsible for these strains' unique capacity for L-tyrosine synthesis.

Rapid declines in the costs of whole genome sequencing have made these techniques much more feasible. We therefore decided to take advantage of the growing availability and increasing affordability of these technologies to fully evaluate the altered genetic make-ups of the isolated strains. Specifically, the genomes of mutants rpoD3, rpoA14, and rpoA27 were analyzed and subsequently compared to the sequences of both parental P2 and the reference genome, E. coli K12 (MG1655).

Figure 16:
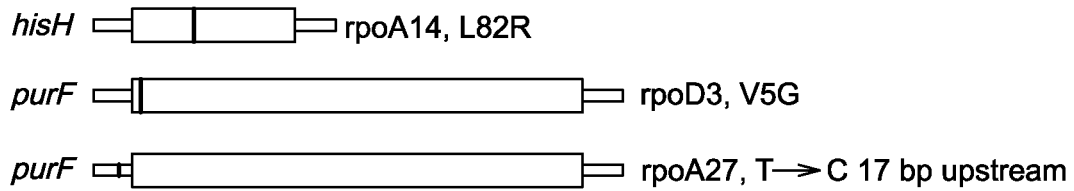
FIG. 16. Locations of validated SNPs within the hisH and purF loci.

As demonstrated in previous studies, the number of changes recovered during whole genome sequencing is sometimes so large that it becomes necessary to focus on mutations within a smaller subset of genes known to be related to phenotype (Ikeda, Ohnishi et al. 2006). In our case, however, we were quite fortunate in that a small and manageable list of possible insertions, deletions, and single nucleotide polymorphisms (SNPs) was recovered during our analysis. Even more auspiciously, validation of these presumed changes by Sanger sequencing revealed that the sequences of rpoA14, rpoA27, and rpoD3 each differed from parental P2 by only a single mutation. A base pair change in rpoA14 resulted in a L82R substitution in the hisH-encoded imidazole glycerol phosphate (IGP) synthase subunit. Mutations in rpoD3 and rpoA27 led to a V5G shift and a T→C nucleotide substitution 17 bp upstream of the purF (amidophosphoribosyl transferase) gene, respectively (Table 3.5, FIG. 16).

TABLE 3.5

Validated SNPs in gTME-derived mutants

| Position | rpoD3 | | rpoA14 | | rpoA27 | | Annotation |
|---|---|---|---|---|---|---|---|
| | R | S | R | S | R | S | |
| 2092803 | | | T | G | | | hisH; imidazole glycerol phosphate synthase subunit, glutamine amidotransferase (histidine biosynthesis) |
| 2428247 | A | C | | | | | purF; amidophosphoribosyl transferase (de novo purine biosynthesis) |
| 2428277 | | | | | T | C | |

R = reference (P2) sequence; S = substituted base pair

Identified SNPs are Necessary for Phenotype

Given that only a single mutation was recovered in each of the three strains, it seems quite likely that these specific modifications represent the previously missing factors needed to impart a L-tyrosine production phenotype. However, to properly validate this conjecture, we decided to reintroduce each SNP into the parental P2 background and test for its specific effects on cellular phenotype. If the identified chromosomal variants are indeed responsible, then strains containing these reconstructed backgrounds and the corresponding rpoA or rpoD plasmids should possess the ability to produce L-tyrosine at the levels seen with the original isolates.

Figure 17:
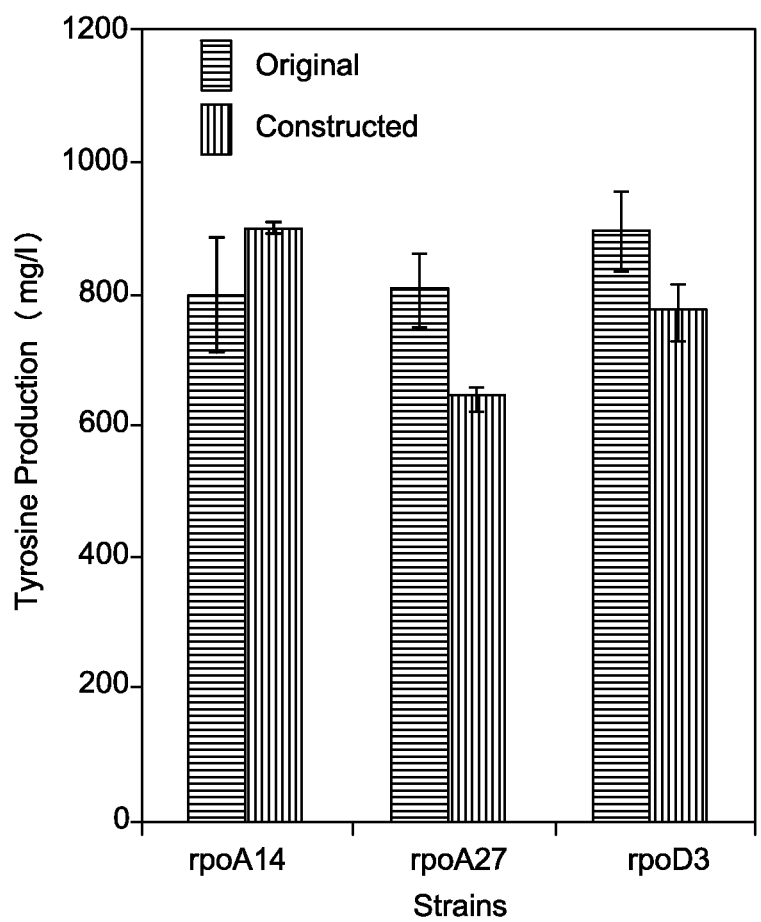
FIG. 17. Comparison of original and reconstructed gTME strains. L-tyrosine titers for the original isolates are shown in left bar in each grouping. The performance of reconstructed strains containing an introduced SNP and their corresponding rpoA or rpoD plasmids is shown in right bar in each grouping. All L-tyrosine concentrations were measured after 48 hr.

Despite slight discrepancies between final titers, we see in FIG. 17 that the chromosomal mutations were in fact able to recover high levels of L-tyrosine production. Interestingly, measurements for the reconstructed rpoA27 and rpoD3 strains (denoted rpoA27$^R$ and rpoD3$^R$) were consistently ~150 mg/l lower than titers of the original isolates, suggesting that additional mutations (such as large-scale insertions or deletions) may have been missed by our sequencing analysis. The opposite was found to be true for rpoA14$^R$, which quite surprisingly exhibited final levels that were over 100 mg/l higher than mutant rpoA14. In spite of these peculiarities, however, these results clearly implicate these specific hisH and purF mutations as being beneficial for L-tyrosine synthesis in these strains. Even more impressively, this analysis has led us to the construction of a completely genetically-defined strain, rpoA14$^R$, which possesses a very respectable titer of 902 mg/l L-tyrosine and a yield of 0.18 g L-tyrosine/g glucose. To put these numbers into perspective, this yield on glucose is more than 150% greater than a classically improved L-phenylalanine auxotroph (DPD4195) that is currently being used for the industrial production of L-tyrosine and, when excluding glucose consumption for biomass formation, represents 85% of the maximum theoretical yield (Olson, Templeton et al. 2007).

Performance of rpoA14$^R$ in Large-Scale Bioreactors

Although the industrial strain DPD4195's yield on glucose was a mere 0.074 g L-tyrosine/g glucose in 50 ml cultures, the transfer of a slightly modified strain into a 200-1 fermentor led to significant improvements in performance with a remarkable yield of 0.28-0.32 g L-tyrosine/g glucose and final titers of 51-57 g/l L-tyrosine (Olson, Templeton et al. 2007; Patnaik, Zolandz et al. 2008). Because such impressive gains were made through simple scale-up and process optimization, we were naturally curious to see how our genetically-defined strain rpoA14$^R$ would perform on the bioreactor scale (2-1 fermentors). Two different minimal medium formulations were tested for this purpose—MOPS minimal medium (Teknova) (Neidhardt, Bloch et al. 1974) and R medium (Riesenberg, Schulz et al. 1991).

Figure 18:
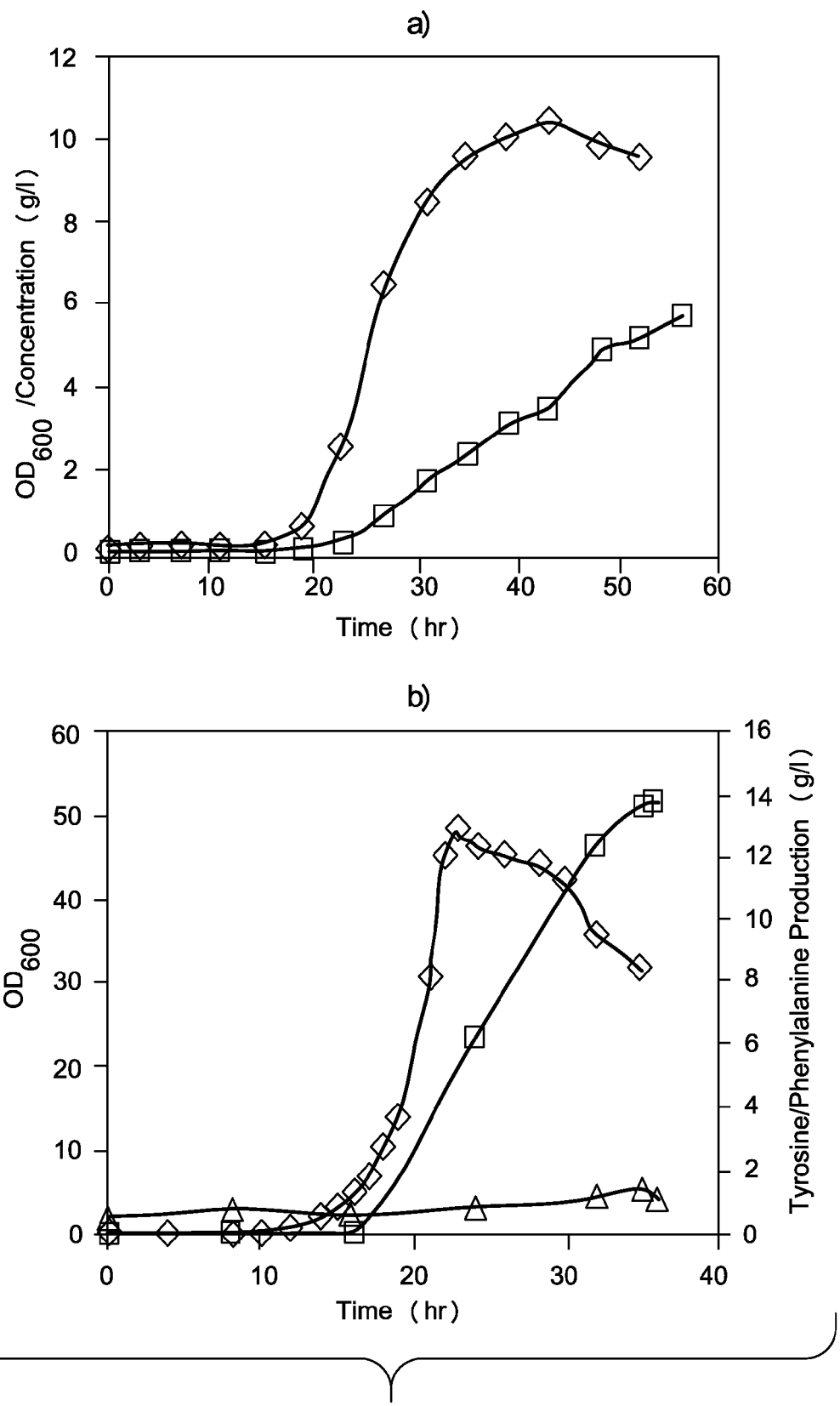
FIG. 18. Performance of rpoA14$^R$ in 2-1 reactors. Two different medium formulations were tested: a) MOPS minimal medium and b) R medium. Measurements for cell density (OD$_{600}$) (◇), L-tyrosine concentrations (□), and L-phenylalanine concentrations (Δ) are reported above.

When cells were cultivated in MOPS minimal medium, strain characteristics appeared to be quite similar to those previously observed in 50 ml shake flask cultures with yields on glucose of 0.204 g L-tyrosine/g glucose and a specific growth rate of 0.275 $hr^{-1}$. Unfortunately, however, cell growth was hampered and peaked at a very low $OD_{600}$ of 10, leading to a titer of just 5.7 g/l L-tyrosine (FIG. 18). The cells behaved quite differently when cultivated in the second medium formulation. Switching to another defined synthetic medium (R medium) led to much higher maximum productivities (2.1 g L-tyrosine/l/hr), titers (13.8 g/l), and growth rates (0.405 $hr^{-1}$) but unfortunately took its toll on overall yield (0.120 g L-tyrosine/g glucose). As has been observed in previous studies, this fermentation also produced ~0.5 g/l L-phenylalanine (in addition to the initial 0.5 g/l supplemented into the medium) during the course of the culture. Other scientists have hypothesized this to be due to the non-enzymatic conversion of prephenate to L-phenylpyruvate, which can then be transaminated to form L-phenylalanine (Young, Gibson et al. 1969; Zamir, Jung et al. 1983; Patnaik, Zolandz et al. 2008).

The results of these two crude experiments make it quite clear that additional process optimization can likely have a significant impact on strain performance in these controlled bioreactor environments. Indeed, identifying limiting nutrients in the MOPS minimal medium formulation may extend the growth and production phase of the cell, and modification of R medium may help to increase the yield to previously observed levels. Ultimately, balancing these two medium formulations and tweaking other important bioreactor parameters should lead to the development of optimal fermentation protocols that maximize the yield, titers, and productivities of these cultures.

In this example, we performed an in-depth analysis of the three gTME-derived strains (rpoD3, rpoA14, and rpoA27) using two common 'omics techniques—microarray analysis and whole genome sequencing. Although widespread problems with data analysis and integration often limit the overall utility of these methods, we remained hopeful that useful information could be extracted from our analyses to guide future metabolic engineering efforts.

Overexpression of Acid Resistance and Stringent Response Regulators can Eliminate the Requirement for a Mutant rpoA or rpoD Although hundreds of genes were recovered by our transcriptional analysis, specific patterns of over- or underexpression led us to investigate the roles of two pathways in E. coli. To our astonishment, we found that the individual overexpression of two regulators/enzymes—evgA and relA—could completely supplant the requirement for either a mutant rpoA or rpoD for recovering a high L-tyrosine production phenotype. Thus, these experiments provide compelling evidence for the specific mechanisms induced by these mutated transcriptional components and clearly implicate both acid resistance and the stringent response in eliciting this desirable phenotype. Although two separate proteins were seen to have the same overall effect on L-tyrosine synthesis, it is important to note that both pathways are actually linked through the actions of the small nucleotide regulator (p)ppGpp. Indeed, because (p)ppGpp levels dictate the onset of both the stringent response and more indirectly, the acid stress pathway, it is possible that these varied cellular responses are, in actuality, linked to a common mode of action. Because (p)ppGpp induction shifts cellular resources from growth to cell maintenance, increased levels of this regulator are often accompanied by proportional decreases in growth rate and increases in acid resistance (higher culture pHs) as were seen in both our knockout and gTME-derived strains (Sarubbi, Rudd et al. 1988).

Owing to the difficulties of analyzing transcriptional data, such success stories are actually quite rare in the literature. We were therefore quite pleased with these results, not only because a feasible mechanism for rpoA/rpoD activity has been established, but also because this example once again demonstrates the enormous benefits of undertaking a combinatorial engineering approach. Because our search for information was not restricted to a predetermined set of genes (as has been required in previous microarray studies) (Wahlbom, Cordero Otero et al. 2003; Bro, Knudsen et al. 2005), we were able to identify seemingly unrelated pathways that, upon further examination, were found to be quite successful in altering cellular phenotype. Indeed, a purely rational approach would not have led us to target a process as global as acid resistance or the stringent response. The ability to recover these unexpected yet exceedingly effective targets is truly an undeniable strength of a combinatorial approach.

Functional Similarities of Recovered SNPs

Because the overexpression of evgA and relA was only effective in the mutant backgrounds, it is clear that unidentified chromosomal variations still play a key role in determining cellular phenotype. To identify such discrepancies, we decided to analyze the sequences of each mutant strain via whole genome sequencing. Although this approach sometimes leads to the identification of more mutations than can be functionally characterized (Ikeda, Ohnishi et al. 2006), we were quite fortunate in that only a single mutation was validated to be present within each mutant. This small number, while initially surprising, does however corroborate previous data showing that the mutational frequencies of these strains have not been significantly altered (FIG. 6). Thus, one would not expect several genomic modifications to emerge within the short time frame required for library generation, screening, and cultivation.

Our analysis revealed that single base pair substitutions occurred within the hisH (IGP synthase subunit, glutamine amidotransferase) and purF (amidophosphoribosyl transferase) loci of E. coli (L82R in hisH for rpoA14 and V5G in purF for rpoD3). HisH and HisF, which together form the heterodimeric enzyme IGP synthase, catalyze a key branch point in histidine biosynthesis. During the fifth step of the pathway, nitrogen from glutamine is used for the formation of IGP with concomitant generation of both glutamate and aminoimidazole carboxamide ribonucleotide (AICAR). Through a similar mechanism, PurF catalyzes the first step of the de novo purine biosynthetic pathway, during which 5-phosphoribosylpyrophosphate (PRPP) and glutamine are enzymatically converted to 5'-phosphoribosylamine (PRA) and glutamate (Mei and Zalkin 1989; Mei and Zalkin 1990; O'Donoghue, Amaro et al. 2001). It is interestingly to note that both altered protein targets reside within biochemically-related systems. Since histidine and purine biosynthesis are actually linked through the intermediate AICAR and the shared precursor PRPP, it is quite possible that both mutations may exert their effects through modulation of a common precursor pathway.

Despite this pathway connectivity, another possible explanation emerged from the interesting observation that HisH and PurF actually possess very similar biochemical functions within the cell. Indeed, both proteins belong to the class of enzymes generally referred to as glutamine amidotransferases (GATases), which utilize glutamine as a source of an amide nitrogen with the concomitant production of glutamate. HisH is classified within the group of type-I GATases, which are distinguished by the presence of a catalytic triad internal to the protein at Cys77, His178, and Glu180 (O'Donoghue, Amaro et al. 2001). Though they possess similar functionalities, type-II GATases, such as PurF are marked by an N-terminal glutamine amidotransferase domain with catalytic residues at Cyst, Asp29, and His 101 (Mei and Zalkin 1989; Mei and Zalkin 1990). Surprisingly, we found that the internal SNPs recovered during our analysis (V5G in rpoD3 and L82R in rpoA14) lie only 4 or 5 amino acids downstream of the catalytic cysteines for both of these enzymes. When compared to a previously constructed hisH structural model, these changes were found to reside within a helical structure directly adjacent to these conserved residues (Mei and Zalkin 1989; Mei and Zalkin 1990; O'Donoghue, Amaro et al. 2001). Because both Cys77 (hisH) and Cyst (purF) possess important roles in glutamine binding, it seems likely that the introduction of these neighboring SNPs may serve to alter the specific substrate affinities of these enzymes. Such a result would then point to a possible role for glutamine/glutamate levels for influencing cellular phenotype, a theory with plausible grounds given that glutamate is consumed during the L-tyrosine pathway's final transamination step. Interestingly, this idea also ties in with previous transcriptional results involving the acid resistance pathway, as glutamate was found to be the main substrate used in that system.

In rpoA27, a T→C mutation was found in the intergenic region between purF and cvpA, which comprise a two-gene polycistronic operon. Although purF transcript levels were found to be downregulated by about two-fold in this strain, it is not clear whether such changes were a result of this mutation, as the promoter/operator region for this operon is actually located upstream of cvpA (Rolfes and Zalkin 1988; Schumacher, Choi et al. 1994).

Performance of Superior Completely Genetically Defined Strain

Results from both microarray studies and whole genome sequencing allowed us to apply an inverse metabolic engineering paradigm for the construction of a completely genetically defined strain for L-tyrosine production. When compared on a 50 ml basis, strain rpoA14$^R$ is capable of significantly outperforming industrial strain DPD4195 with respect to both yields and titers (Olson, Templeton et al. 2007). Early bioreactor experiments point to the potential for process scale-up but also illustrate the need for additional process optimization to achieve maximum titers, yields, and productivities.

In Table 3.6, we provide a quick comparison of two experiments conducted with rpoA14$^R$, as well as fermentation parameters for the fully rationally engineered strain T2 (Lütke-Eversloh and Stephanopoulos 2007) and DuPont's industrial producer DPD4195 (Patnaik, Zolandz et al. 2008). As briefly mentioned earlier, two different fermentation media were tested for rpoA14$^R$ (MOPS minimal and R media), with each showing a unique ability to maximize either yields or maximum productivities, respectively. Cultivation in MOPS minimal medium resulted in a yield of 0.204 g L-tyrosine/g glucose, which was exactly twice the value observed in T2 fermentations. Similarly, maximum productivities in R medium were found to be twofold greater than T2 values as well (188 versus 92.6 mg L-tyrosine/g DCW/hr). Although overall productivities for rpoA14$^R$ seem low compared to both T2 and DPD4195, this parameter was skewed by the long lag time seen in our cultures, a feature that can be either partially or completely eliminated by optimizing our inoculation protocols.

It is interesting to note that scale-up and process optimization of DPD4195 cultures led to significant improvements in strain performance, with more than a quadrupling in yield (0.07 to 0.3 g L-tyrosine/g glucose) and an impressive titer of 55 µl (Young, Gibson et al. 1969; Zamir, Jung et al. 1983; Patnaik, Zolandz et al. 2008). Given this remarkable potential for process-related gains, we are confident that similar improvements can be achieved with our engineered strain in order to transform it into a competitive or superior industrial performer.

TABLE 3.6

Comparison of bioreactor parameters

| | T2 (3-1) | DPD4195 (200-1) | rpoA14$^R$ (MOPS) | rpoA14$^R$ (R) |
|---|---|---|---|---|
| Final L-Tyr Titer (g/l) | 9.7 | 55 | 5.71 | 13.8 |
| Total Glucose consumed (g/l) | 95 | 183 | 28 | 115 |
| Overall yield (g Tyr/g Glc) | 0.102 | 0.3 | 0.204 | 0.120 |
| Maximum Productivity (mg Tyr/g DCW/hr) | 92.6 | — | 88.24 | 188 |
| Maximum Productivity (g Tyr/l/hr) | — | — | 0.280 | 2.06 |
| Overall Productivity (g Tyr/l/hr) | 0.626 | 1.15 | 0.102 | 0.391 |
| Growth rate (hr$^{-1}$) | 0.26 | — | 0.275 | 0.405 |
| Maximum OD$_{600}$ | 120 | 65 | 10.4 | 48.1 |

REFERENCES

Alper, H., C. Fischer, et al. (2005). "Tuning genetic control through promoter engineering." *Proc Natl Acad Sci USA* 102(36): 12678-83.

Alper, H. and G. Stephanopoulos (2007). "Global transcription machinery engineering: a new approach for improving cellular phenotype." *Metab Eng* 9(3): 258-67.

Bro, C., S. Knudsen, et al. (2005). "Improvement of galactose uptake in *Saccharomyces cerevisiae* through overexpression of phosphoglucomutase: example of transcript analysis as a tool in inverse metabolic engineering." *Appl Environ Microbiol* 71(11): 6465-72.

Browning, D. F. and S. J. Busby (2004). "The regulation of bacterial transcription initiation."*Nat Rev Microbiol* 2(1): 57-65.

Chang, D. E., D. J. Smalley, et al. (2002). "Gene expression profiling of *Escherichia coli* growth transitions: an expanded stringent response model." *Mol Microbiol* 45(2): 289-306.

Dangi, B., A. M. Gronenborn, et al. (2004). "Versatility of the carboxy-terminal domain of the alpha subunit of RNA polymerase in transcriptional activation: use of the DNA contact site as a protein contact site for MarA." *Mol Microbiol* 54(1): 45-59.

Datsenko, K. A. and B. L. Wanner (2000). "One-step inactivation of chromosomal genes in *Escherichia coli* K-12 using PCR products." *Proc Natl Acad Sci USA* 97(12): 6640-5.

Durfee, T., A. M. Hansen, et al. (2008). "Transcription profiling of the stringent response in *Escherichia coli*." *J Bacteriol* 190(3): 1084-96.

Fukui, S., S. I. Ikeda, et al. (1975). "Production of L-Tryptophan, L-Tyrosine and Their Analogs by Use of Immobilized Tryptophanase and Immobilized Beta-Tyrosinase." *European Journal of Applied Microbiology* 1(1): 25-39.

Gaal, T., W. Ross, et al. (1996). "DNA-binding determinants of the alpha subunit of RNA polymerase: novel DNA-binding domain architecture." *Genes Dev* 10(1): 16-26.

Gajiwala, K. S, and S. K. Burley (2000). "HDEA, a periplasmic protein that supports acid resistance in pathogenic enteric bacteria." *J Mol Biol* 295(3): 605-12.

Garibyan, L., T. Huang, et al. (2003). "Use of the rpoB gene to determine the specificity of base substitution mutations on the *Escherichia coli* chromosome." *DNA Repair (Amst)* 2(5): 593-608.

Gruber, T. M. and C. A. Gross (2003). "Multiple sigma subunits and the partitioning of bacterial transcription space." *Annu Rev Microbiol* 57: 441-66.

Ikeda, M., J. Ohnishi, et al. (2006). "A genome-based approach to create a minimally mutated *Corynebacterium glutamicum* strain for efficient L-lysine production." *J Ind Microbiol Biotechnol* 33(7): 610-5.

Imaizumi, A., H. Kojima, et al. (2006). "The effect of intracellular ppGpp levels on glutamate and lysine overproduction in *Escherichia coli*." *J Biotechnol* 125(3): 328-37.

Ishihama, A. (2000). "Functional modulation of *Escherichia coli* RNA polymerase." *Annu Rev Microbiol* 54: 499-518.

Jishage, M., K. Kvint, et al. (2002). "Regulation of sigma factor competition by the alarmone ppGpp." *Genes Dev* 16(10): 1260-70.

Kern, R., A. Malki, et al. (2007). "*Escherichia coli* HdeB is an acid stress chaperone." *J Bacteriol* 189(2): 603-10.

Klein-Marcuschamer, D., C. N. Santos, et al. (2009). "Mutagenesis of the bacterial RNA polymerase alpha subunit for improvement of complex phenotypes." *Appl Environ Microbiol* 75(9): 2705-11.

Klein-Marcuschamer, D. and G. Stephanopoulos (2008). "Assessing the potential of mutational strategies to elicit new phenotypes in industrial strains." *Proc Natl Acad Sci USA* 105(7): 2319-24.

Leonard, E., K. H. Lim, et al. (2007). "Engineering central metabolic pathways for high-level flavonoid production in *Escherichia coli*." *Appl Environ Microbiol* 73(12): 3877-86.

Leonard, E., Y. Yan, et al. (2008). "Strain improvement of recombinant *Escherichia coli* for efficient production of plant flavonoids." *Mol Pharm* 5(2): 257-65.

Li, S. C., N. K. Goto, et al. (1996). "Alpha-helical, but not beta-sheet, propensity of proline is determined by peptide environment." *Proc Natl Acad Sci USA* 93(13): 6676-81.

Lutke-Eversloh, T. and G. Stephanopoulos (2007). "L-Tyrosine production by deregulated strains of *Escherichia coli*." *Appl Microbiol Biotechnol* 75(1): 103-10.

Lütke-Eversloh, T. and G. Stephanopoulos (2007). "A semi-quantitative high-throughput screening method for microbial L: -tyrosine production in microtiter plates." *J Ind Microbiol Biotechnol* 34(12): 807-811.

Lütke-Eversloh, T. and G. Stephanopoulos (2008). "Combinatorial pathway analysis for improved L-tyrosine production in *Escherichia coli*: identification of enzymatic bottlenecks by systematic gene overexpression." *Metab Eng* 10(2): 69-77.

Ma, Z., S. Gong, et al. (2003). "GadE (YhiE) activates glutamate decarboxylase-dependent acid resistance in *Escherichia coli* K-12." *Mol Microbiol* 49(5): 1309-20.

Ma, Z., N. Masuda, et al. (2004). "Characterization of EvgAS-YdeO-GadE branched regulatory circuit governing glutamate-dependent acid resistance in *Escherichia coli*." *J Bacteriol* 186(21): 7378-89.

Magnusson, L. U., A. Farewell, et al. (2005). "ppGpp: a global regulator in *Escherichia coli*." *Trends Microbiol* 13(5): 236-42.

Malki, A., H. T. Le, et al. (2008). "Solubilization of protein aggregates by the acid stress chaperones HdeA and HdeB." *J Biol Chem* 283(20): 13679-87.

Masuda, N. and G. M. Church (2003). "Regulatory network of acid resistance genes in *Escherichia coli*." *Mol Microbiol* 48(3): 699-712.

Mei, B. and H. Zalkin (1989). "A cysteine-histidine-aspartate catalytic triad is involved in glutamine amide transfer function in purF-type glutamine amidotransferases." *J Biol Chem* 264(28): 16613-9.

Mei, B. G. and H. Zalkin (1990). "Amino-terminal deletions define a glutamine amide transfer domain in glutamine phosphoribosylpyrophosphate amidotransferase and other PurF-type amidotransferases." *J Bacteriol* 172(6): 3512-4.

Miller, J. H. (1992). *A short course in bacterial genetics: a laboratory manual and handbook for Escherichia coli and related bacteria*. Plainview, N.Y., Cold Spring Harbor Laboratory Press.

Murakami, K., N. Fujita, et al. (1996). "Transcription factor recognition surface on the RNA polymerase alpha subunit is involved in contact with the DNA enhancer element." *Embo J* 15(16): 4358-67.

Neidhardt, F. C., P. L. Bloch, et al. (1974). "Culture medium for enterobacteria." *J Bacteriol* 119(3): 736-47.

Nishino, K., Y. Inazumi, et al. (2003). "Global analysis of genes regulated by EvgA of the two-component regulatory system in *Escherichia coli*." *J Bacteriol* 185(8): 2667-72.

Nishino, K. and A. Yamaguchi (2001). "Overexpression of the response regulator evgA of the two-component signal transduction system modulates multidrug resistance conferred by multidrug resistance transporters." *J Bacteriol* 183(4): 1455-8.

O'Donoghue, P., R. E. Amaro, et al. (2001). "On the structure of hisH: protein structure prediction in the context of structural and functional genomics." *J Struct Biol* 134(2-3): 257-68.

Olson, M. M., L. J. Templeton, et al. (2007). "Production of tyrosine from sucrose or glucose achieved by rapid genetic changes to phenylalanine-producing *Escherichia coli* strains." *Appl Microbiol Biotechnol* 74(5): 1031-40.

Patnaik, R., R. R. Zolandz, et al. (2008). "L-tyrosine production by recombinant *Escherichia coli*: fermentation optimization and recovery." *Biotechnol Bioeng* 99(4): 741-52.

Paul, B. J., M. B. Berkmen, et al. (2005). "DksA potentiates direct activation of amino acid promoters by ppGpp." *Proc Natl Acad Sci USA* 102(22): 7823-8.

Potrykus, K. and M. Cashel (2008). "(p)ppGpp: still magical?" *Annu Rev Microbiol* 62: 35-51.

Qi, W. W., T. Vannelli, et al. (2007). "Functional expression of prokaryotic and eukaryotic genes in *Escherichia coli* for conversion of glucose to p-hydroxystyrene." *Metab Eng* 9(3): 268-76.

Riesenberg, D., V. Schulz, et al. (1991). "High cell density cultivation of *Escherichia coli* at controlled specific growth rate." *J Biotechnol* 20(1): 17-27.

Rolfes, R. J. and H. Zalkin (1988). "Regulation of *Escherichia coli* purF. Mutations that define the promoter, operator, and purine repressor gene." *J Biol Chem* 263(36): 19649-52.

Ross, W., K. K. Gosink, et al. (1993). "A third recognition element in bacterial promoters: DNA binding by the alpha subunit of RNA polymerase." *Science* 262(5138): 1407-13.

Sambrook, J., E. F. Fritsch, et al. (1989). *Molecular cloning: a laboratory manual*. Cold Spring Harbor, N.Y., Cold Spring Harbor Laboratory.

Santos, C. N. and G. Stephanopoulos (2008). "Melanin-based high-throughput screen for L-tyrosine production in *Escherichia coli*." *Appl Environ Microbiol* 74(4): 1190-7.

Sariaslani, F. S. (2007). "Development of a combined biological and chemical process for production of industrial aromatics from renewable resources." *Annu Rev Microbiol* 61: 51-69.

Sarubbi, E., K. E. Rudd, et al. (1988). "Basal ppGpp level adjustment shown by new spoT mutants affect steady state growth rates and rrnA ribosomal promoter regulation in *Escherichia coli*." *Mol Gen Genet*. 213(2-3): 214-22.

Schumacher, M. A., K. Y. Choi, et al. (1994). "Crystal structure of LacI member, PurR, bound to DNA: minor groove binding by alpha helices." *Science* 266(5186): 763-70.

Sharma, U. K. and D. Chatterji (2008). "Differential mechanisms of binding of anti-sigma factors *Escherichia coli* Rsd and bacteriophage T4 AsiA to *E. coli* RNA polymerase lead to diverse physiological consequences." *J Bacteriol* 190(10): 3434-43.

Sharma, U. K., S. Ravishankar, et al. (1999). "Study of the interaction between bacteriophage T4 asiA and *Escherichia coli* sigma(70), using the yeast two-hybrid system: neutralization of asiA toxicity to *E. coli* cells by coexpression of a truncated sigma(70) fragment." *J Bacteriol* 181 (18): 5855-9.

Srivatsan, A. and J. D. Wang (2008). "Control of bacterial transcription, translation and replication by (p)ppGpp." *Curr Opin Microbiol* 11(2): 100-5.

Stephens, J. C., S. W. Artz, et al. (1975). "Guanosine 5'-diphosphate 3'-diphosphate (ppGpp): positive effector for histidine operon transcription and general signal for amino-acid deficiency." *Proc Natl Acad Sci USA* 72(11): 4389-93.

Traxler, M. F., S. M. Summers, et al. (2008). "The global, ppGpp-mediated stringent response to amino acid starvation in *Escherichia coli*." *Mol Microbiol* 68(5): 1128-48.

Vannelli, T., W. Wei Qi, et al. (2007). "Production of p-hydroxycinnamic acid from glucose in *Saccharomyces cerevisiae* and *Escherichia coli* by expression of heterologous genes from plants and fungi." *Metab Eng* 9(2): 142-51.

Wahlbom, C. F., R. R. Cordero Otero, et al. (2003). "Molecular analysis of a *Saccharomyces cerevisiae* mutant with improved ability to utilize xylose shows enhanced expression of proteins involved in transport, initial xylose metabolism, and the pentose phosphate pathway." *Appl Environ Microbiol* 69(2): 740-6.

Young, I. G., F. Gibson, et al. (1969). "Enzymic and nonenzymic transformations of chorismic acid and related cyclohexadienes." *Biochim Biophys Acta* 192(1): 62-72.

Zamir, L. O., E. Jung, et al. (1983). "Co-accumulation of prephenate, L-arogenate, and spiro-arogenate in a mutant of *Neurospora*." *J Biol Chem* 258(10): 6492-6.

Other aspects of the invention will be clear to the skilled artisan and need not be repeated here. Each reference cited herein is incorporated by reference in its entirety for the relevant teaching contained therein.

The terms and expressions that have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. A bacterial cell having improved L-tyrosine production relative to a parental strain, wherein the bacterial cell comprises
   (a) (1) one or more mutations in a rpoA gene or a rpoD gene, and/or
       (2) increased expression, relative to a parental strain, of one or more of evgA, relA, gadA, gadB, gadC, gadE, hdeA, hdeB, hdeD, and/or slp; and
   (b) one or more mutations in hisH and/or purF;
   wherein the bacterial cell is not rpoA14.

2. The bacterial cell of claim 1, wherein the one or more mutations in the rpoA or the rpoD gene comprises one or more mutations that results in a helical destabilization or deletion of the C-terminal domain of the α-subunit of RNA polymerase (αCTD).

3. The bacterial cell of claim 2, wherein the one or more mutations in the rpoA gene comprises one or more mutations of the nucleotide sequence of full-length wild-type E. coli K12 rpoA encoding amino acid residues V257 and/or L281 or equivalent amino acid residues in rpoA genes of E. coli or of other bacterial strains, optionally wherein the one or more mutations of the nucleotide sequence of full-length wild-type E. coli K12 rpoA encoding amino acid residue V257 encodes V257F or V257R or an equivalent amino acid residue in rpoA genes of E. coli or of other bacterial strains, and/or wherein the one or more mutations of the nucleotide sequence of full-length wild-type E. coli K12 rpoA encoding amino acid residue L281 encodes L281P or an equivalent amino acid residue in rpoA genes of E. coli or of other bacterial strains.

4. The bacterial cell of claim 1, wherein the one or more mutations in the rpoD gene comprises truncation of the nucleotide sequence of rpoD, optionally wherein the truncation of the nucleotide sequence of rpoD results in a nucleotide sequence that encodes Region 4 and the end of Region 3 of RpoD protein and/or optionally wherein the truncation is a deletion of the first 1512 base pairs of E. coli K12 rpoD or 756 amino acids of E. coli K12 RpoD protein.

5. The bacterial cell of claim 1, wherein the bacterial cell comprises increased expression, relative to a parental strain, of one or more of evgA, relA, gadA, gadB, gadC, gadE, hdeA, hdeB, hdeD, and/or slp, optionally wherein the expression, relative to a parental strain, of one or more of evgA, relA, gadA, gadB, gadC, gadE, hdeA, hdeB, hdeD, and/or slp is increased by expression from a recombinant plasmid.

6. The bacterial cell of claim 1, wherein the mutation in hisH comprises one or more mutations of the nucleotide sequence of full-length wild-type E. coli K12 hisH encoding amino acid residue L82, or an equivalent amino acid residue in hisH genes of E. coli or of other bacterial strains, optionally wherein the one or more mutations of the nucleotide sequence of full-length wild-type E. coli K12 hisH encoding amino acid residue L82 encodes L82R, or an equivalent amino acid residue in hisH genes of E. coli or of other bacterial strains.

7. The bacterial cell of claim 1, wherein the mutation in purF comprises one or more mutations of the nucleotide sequence of full-length wild-type E. coli K12 purF encoding amino acid residue V5 or an equivalent amino acid residue in purF genes of E. coli or of other bacterial strains, optionally wherein the one or more mutations of the nucleotide sequence of full-length wild-type *E. coli* K12 purF encoding amino acid residue V5 encodes V5G or an equivalent amino acid residue in purF genes of *E. coli* or of other bacterial strains and/or wherein the mutation in full-length wild-type *E. coli* K12 purF comprises a TC nucleotide substitution 17 base pairs upstream of the purF gene or an equivalent nucleotide substitution in purF genes of *E. coli* or of other bacterial strains.

8. The bacterial cell of claim 1, wherein the parental strain is an *E. coli* strain, optionally wherein the parental strain is an *E. coli* K12 strain and optionally wherein the *E. coli* K12 strain is *E. coli* K12 ΔpheAΔtyrR pCL1920:: tyrA$^{fbr}$aroG$^{fbr}$ (P1) or *E. coli* K12 ΔpheA tyrR::tyrA$^{fbr}$aroG$^{fbr}$ lacZ::tyr A$^{fbr}$aroG$^{fbr}$ (P2).

9. The bacterial cell of claim 8, wherein the strain is a completely genetically defined strain, optionally rpoA14$^R$.

10. The bacterial cell of claim 1, wherein upon culturing the cell produces at least 800 milligrams/liter L-tyrosine in the culture medium.

11. A method for producing L-tyrosine comprising
culturing the bacterial cell of claim 1 to produce the L-tyrosine,
optionally further comprising recovering the L-tyrosine from the culture medium or the cells.

12. The method of claim 11, wherein the carbon source is glucose or a glucose polymer.

13. The method of claim 11, wherein the cell produces at least 800 milligrams/liter L-tyrosine or at least 0.280 grams L-tyrosine/liter/hour.

14. The method of claim 11, wherein the cell produces a yield of L-tyrosine on glucose of at least 0.16 grams L-tyrosine/gram glucose.

* * * * *

SEQUENCE LISTING

<160> NUMBER OF SEQ ID NOS: 25

<210> SEQ ID NO 1
<211> LENGTH: 36
<212> TYPE: DNA
<213> ORGANISM: artificial sequence
<220> FEATURE:
<223> OTHER INFORMATION: oligonucleotide primer

<400> SEQUENCE: 1
gctcggtacc atggttgctg aattgaccgc attacg         36

<210> SEQ ID NO 2
<211> LENGTH: 31
<212> TYPE: DNA
<213> ORGANISM: artificial sequence
<220> FEATURE:
<223> OTHER INFORMATION: oligonucleotide primer

<400> SEQUENCE: 2
cgacgcgttt acccgcgacg cgcttttact g              31

<210> SEQ ID NO 3
<211> LENGTH: 33
<212> TYPE: DNA
<213> ORGANISM: artificial sequence
<220> FEATURE:
<223> OTHER INFORMATION: oligonucleotide primer

<400> SEQUENCE: 3
tccgagctct tgtgtaggct ggagctgctt cga            33

<210> SEQ ID NO 4

```
<211> LENGTH: 40
<212> TYPE: DNA
<213> ORGANISM: artificial sequence
<220> FEATURE:
<223> OTHER INFORMATION: oligonucleotide primer

<400> SEQUENCE: 4
tcttagacgt cggaattgat ccgtcgacct gcagttcgaa                    40

<210> SEQ ID NO 5
<211> LENGTH: 88
<212> TYPE: DNA
<213> ORGANISM: artificial sequence
<220> FEATURE:
<223> OTHER INFORMATION: oligonucleotide primer

<400> SEQUENCE: 5
ttccggcacc agaagcggtg ccggaaagct ggctggagtg cgatcttcct gaggccgata    60
ctgtcgtcgt cccctttacc cgcgacgc                                      88

<210> SEQ ID NO 6
<211> LENGTH: 97
<212> TYPE: DNA
<213> ORGANISM: artificial sequence
<220> FEATURE:
<223> OTHER INFORMATION: oligonucleotide primer

<400> SEQUENCE: 6
cgcgtgcagc agatggcgat ggctggtttc catcagttgc tgttgactgt agcggctgat    60
gttgaactgg aagtcgtgta ggctggagct gcttcga                            97

<210> SEQ ID NO 7
<211> LENGTH: 100
<212> TYPE: DNA
<213> ORGANISM: artificial sequence
<220> FEATURE:
<223> OTHER INFORMATION: oligonucleotide primer

<400> SEQUENCE: 7
tgcaatatcg ggtgctgacc ggatatcttt acgccgaagt gcccgttttt ccgtctttgt    60
gtcaatgatt gttgacaggt gtaggctgga gctgcttcga                        100

<210> SEQ ID NO 8
<211> LENGTH: 100
<212> TYPE: DNA
<213> ORGANISM: artificial sequence
<220> FEATURE:
<223> OTHER INFORMATION: oligonucleotide primer

<400> SEQUENCE: 8
taatttaata tgcctgatgg tgttgcacca tcaggcatat tcgcgcttac tcttcgttct    60
tcttctgact cagaccatta cccgcgacgc gcttttactg                        100

<210> SEQ ID NO 9
<211> LENGTH: 73
<212> TYPE: DNA
<213> ORGANISM: artificial sequence
<220> FEATURE:
<223> OTHER INFORMATION: oligonucleotide primer

<400> SEQUENCE: 9
agttacgcgt tgtttttgcg acagatgaag agattgcagc tcatgaagcc taagtgtagg    60
ctggagctgc ttc                                                      73
```

```
<210> SEQ ID NO 10
<211> LENGTH: 71
<212> TYPE: DNA
<213> ORGANISM: artificial sequence
<220> FEATURE:
<223> OTHER INFORMATION: oligonucleotide primer

<400> SEQUENCE: 10
gcaaaaatcg cccaagtcgc tattttagc gcctttcaca ggtatttatg atccgtcgac      60
ctgcagttcg a                                                          71

<210> SEQ ID NO 11
<211> LENGTH: 38
<212> TYPE: DNA
<213> ORGANISM: artificial sequence
<220> FEATURE:
<223> OTHER INFORMATION: oligonucleotide primer

<400> SEQUENCE: 11
ctcggtacca tgaacgcaat aattattgat gaccatcc                             38

<210> SEQ ID NO 12
<211> LENGTH: 33
<212> TYPE: DNA
<213> ORGANISM: artificial sequence
<220> FEATURE:
<223> OTHER INFORMATION: oligonucleotide primer

<400> SEQUENCE: 12
cgacgcgttt agccgatttt gttacgttgt gcg                                  33

<210> SEQ ID NO 13
<211> LENGTH: 40
<212> TYPE: DNA
<213> ORGANISM: artificial sequence
<220> FEATURE:
<223> OTHER INFORMATION: oligonucleotide primer

<400> SEQUENCE: 13
ctcggtacca tgtcgctcgt ttgttctgtt atatttattc                           40

<210> SEQ ID NO 14
<211> LENGTH: 40
<212> TYPE: DNA
<213> ORGANISM: artificial sequence
<220> FEATURE:
<223> OTHER INFORMATION: oligonucleotide primer

<400> SEQUENCE: 14
ggtctctctt ttcaaatagc taaagcattc atcgtgttgc                           40

<210> SEQ ID NO 15
<211> LENGTH: 40
<212> TYPE: DNA
<213> ORGANISM: artificial sequence
<220> FEATURE:
<223> OTHER INFORMATION: oligonucleotide primer

<400> SEQUENCE: 15
ctcggtacca tgattttct catgacgaaa gattcttttc                            40

<210> SEQ ID NO 16
<211> LENGTH: 39
<212> TYPE: DNA
<213> ORGANISM: artificial sequence
<220> FEATURE:
```

<223> OTHER INFORMATION: oligonucleotide primer

<400> SEQUENCE: 16
cgacgcgtct aaaaataaga tgtgataccc agggtgacg        39

<210> SEQ ID NO 17
<211> LENGTH: 37
<212> TYPE: DNA
<213> ORGANISM: artificial sequence
<220> FEATURE:
<223> OTHER INFORMATION: oligonucleotide primer

<400> SEQUENCE: 17
ctcggtacca tggttgcggt aagaagtgca catatca        37

<210> SEQ ID NO 18
<211> LENGTH: 24
<212> TYPE: DNA
<213> ORGANISM: artificial sequence
<220> FEATURE:
<223> OTHER INFORMATION: oligonucleotide primer

<400> SEQUENCE: 18
gcagcaatgg cagcgaaaat attg        24

<210> SEQ ID NO 19
<211> LENGTH: 26
<212> TYPE: DNA
<213> ORGANISM: artificial sequence
<220> FEATURE:
<223> OTHER INFORMATION: oligonucleotide primer

<400> SEQUENCE: 19
cagtctggtt tacgggcttt gaagac        26

<210> SEQ ID NO 20
<211> LENGTH: 24
<212> TYPE: DNA
<213> ORGANISM: artificial sequence
<220> FEATURE:
<223> OTHER INFORMATION: oligonucleotide primer

<400> SEQUENCE: 20
tctcagcacc gaaatgatcg agca        24

<210> SEQ ID NO 21
<211> LENGTH: 26
<212> TYPE: DNA
<213> ORGANISM: artificial sequence
<220> FEATURE:
<223> OTHER INFORMATION: oligonucleotide primer

<400> SEQUENCE: 21
ccggaataat catcacatct ccagga        26

<210> SEQ ID NO 22
<211> LENGTH: 73
<212> TYPE: DNA
<213> ORGANISM: artificial sequence
<220> FEATURE:
<223> OTHER INFORMATION: oligonucleotide primer

<400> SEQUENCE: 22
taacgcacat gaccaatgcc catattgccc tgcaaacgct gcatatggcg agcgtgtagg        60
ctggagctgc ttc        73

```
<210> SEQ ID NO 23
<211> LENGTH: 71
<212> TYPE: DNA
<213> ORGANISM: artificial sequence
<220> FEATURE:
<223> OTHER INFORMATION: oligonucleotide primer

<400> SEQUENCE: 23
cggtactgtt tatcgctacc ctgatcgttg gtgctatcgt gaacttcgtg atccgtcgac        60
ctgcagttcg a                                                             71

<210> SEQ ID NO 24
<211> LENGTH: 79
<212> TYPE: DNA
<213> ORGANISM: artificial sequence
<220> FEATURE:
<223> OTHER INFORMATION: oligonucleotide primer

<400> SEQUENCE: 24
cgtgacccgg acgtcgtgtt gctggccgat aaactgtttt tacccggcgt tggcactgat        60
ccgtcgacct gcagttcga                                                     79

<210> SEQ ID NO 25
<211> LENGTH: 73
<212> TYPE: DNA
<213> ORGANISM: artificial sequence
<220> FEATURE:
<223> OTHER INFORMATION: oligonucleotide primer

<400> SEQUENCE: 25
cggcattgcg tagctgtgaa caaagtaaaa gtacgcgccg tcttcaatcc cctgtgtagg        60
ctggagctgc ttc                                                           73
```